(12) United States Patent
Daniell

(10) Patent No.: US 10,676,751 B2
(45) Date of Patent: Jun. 9, 2020

(54) PRODUCTION AND USE OF PLANT DEGRADING MATERIALS

(75) Inventor: Henry Daniell, Winter Park, FL (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1402 days.

(21) Appl. No.: 12/396,382

(22) Filed: Mar. 2, 2009

(65) Prior Publication Data

US 2009/0325240 A1 Dec. 31, 2009

Related U.S. Application Data

(60) Provisional application No. 61/032,536, filed on Feb. 29, 2008.

(51) Int. Cl.
| | |
|---|---|
| C12N 15/82 | (2006.01) |
| C12P 7/12 | (2006.01) |
| C12N 9/42 | (2006.01) |
| C12N 9/24 | (2006.01) |

(52) U.S. Cl.
CPC ....... *C12N 15/8214* (2013.01); *C12N 9/2437* (2013.01); *C12N 9/2445* (2013.01); *C12N 9/2482* (2013.01); *C12N 15/8242* (2013.01); *C12N 15/8257* (2013.01); *C12P 7/12* (2013.01); *C12Y 302/01004* (2013.01); *C12Y 302/01008* (2013.01); *C12Y 302/01021* (2013.01); *C12Y 302/01091* (2013.01)

(58) Field of Classification Search
CPC ................................................ C12N 15/8214
See application file for complete search history.

(56) References Cited

U.S. PATENT DOCUMENTS

| | | | | |
|---|---|---|---|---|
| 6,326,470 B1 * | 12/2001 | Cosgrove | ............. | C07K 14/415 435/183 |
| 6,458,928 B1 * | 10/2002 | Swanson | ................ | C07K 14/37 435/262 |
| 6,818,803 B1 * | 11/2004 | Austin-Phillips | ........................... | C12N 15/8242 435/410 |
| 7,923,236 B2 * | 4/2011 | Gusakov | ............ | C11D 3/38645 162/174 |
| 8,481,810 B2 * | 7/2013 | Lebel et al. | ................... | 800/284 |
| 2002/0062502 A1 * | 5/2002 | Lebel | ................. | C12N 15/8214 800/298 |
| 2002/0138878 A1 * | 9/2002 | Sticklen | ............. | C12N 15/8207 800/288 |
| 2005/0106699 A1 * | 5/2005 | Reddy et al. | ................. | 435/200 |
| 2005/0233423 A1 | 10/2005 | Berka et al. | | |
| 2007/0192900 A1 | 8/2007 | Sticklen | | |
| 2008/0022425 A1 | 1/2008 | Lebel et al. | | |

FOREIGN PATENT DOCUMENTS

| | | | | |
|---|---|---|---|---|
| WO | WO 9811235 A2 * | 3/1998 | ......... | C12N 15/8214 |
| WO | WO 00/05381 A2 | 2/2000 | | |
| WO | WO 2007/1157263 | * 10/2007 | | |
| WO | WO 2007115723 A3 * | 11/2007 | ........... | A23L 1/3055 |

OTHER PUBLICATIONS

Xu et al (Journal of Biotechnology 131 (2007) 362-369—cited in Applicant's IDS filed on Jan. 28, 2013).*
Gramauf et al. "Degradation of Plant Cell Wall Polymers by Fungi" The Mycota,vol. IV: environmental and Microbial Relationships, p. 325-340,2007.*
Malburg et al (Applied and Environmental Microbiology, Mar. 1996, p. 898-906).*
Gamauf et al (The Mycota, vol. IV: (2007) Environmental and Microbial Relationships, pp. 325-340).*
Zverlov et al (Microbiology (2002), 148, 247-255).*
Roy et al (Journal of Bacteriology, Jun. 1999, p. 3705-3709).*
Han et al (Enzyme and Microbial Technology, 2007).*
Han et al (Enzyme and Microbial Technology, 2007) (Year: 2007).*
Yu et al (Journal of Biotechnology 131 (2007) 362-369) (Year: 2007).*
Gamauf et al (The Mycota, vol. IV: (2007) Environmental and Microbial Relationships, pp. 325-340) (Year: 2007).*
Zverlov et al (Microbiology (2002), 148, 247-255) (Year: 2002).*
Roy et al (Journal of Bacteriology, Jun. 1999, p. 3705-3709) (Year: 1999).*
Degani et al (Applied Biochemistry and Biotechnology (2002) vol. 102, 277-289). (Year: 2002).*
Ladanyia et al (Citrus Fruit : Biology, Technology and Evaluation, Elsevier Science & Technology (2008) 127-178—Published Feb. 6, 2008 (Year: 2008).*
Carvalhoet al (Electronic Journal of Biotechnology, North America, 115 12 1998) (Year: 1998).*
Queiroz, Lídia N., et al. "Evaluation of lettuce chloroplast and soybean cotyledon as platforms for production of functional bone morphogenetic protein 2." Transgenic research 28.2 (2019): 213-224. (Year: 2019).*
Stewart "Fuel Ethanol Production From Citrus Waste Biomass" citrus Energy LLC, Bioenergy Projects grant application Mar. 8, 2007 [online] downloaded from: http://www.floridaep.org/energy/energyact/files/grant/2006%20award%20winners/Original%20Proposals/citrus.pdf: downloaded on Aug. 9, 2009; p. 1 para 4 and p. 2 para 2/.

(Continued)

*Primary Examiner* — Lee A Visone
(74) *Attorney, Agent, or Firm* — Kathleen D. Rigaut; Howson & Howson LLP

(57) ABSTRACT

Disclosed herein are materials useful for degrading plant biomass material. In exemplary embodiments, the plant material comprises one or more enzymes that are expressed in plants and/or bacteria. Specifically exemplified herein are plant degrading enzymes expressed in chloroplasts. The chloroplast expressed enzymes may be provided as cocktails for use in conjunction with conventional methods of converting biomass into biofuels, such as cellulosic ethanol.

15 Claims, 7 Drawing Sheets
Specification includes a Sequence Listing.

(56) References Cited

OTHER PUBLICATIONS

Gramauf et al. "Degradation of Plant Cell Wall Polymers by Fungi" The Mycota, vol. IV: environmental and Microbial Relationships, p. 325-340, 2007, p. 329 col. 1 para 3 to col. 2 para 1.
Sorensen, H.R. et al., "Efficiencies of designed enzyme combinations in releasing arabinose and xylose from wheat arabinoxylan in an industrial ethanol fermentation residue" Enzyme and Microbial Technology, vol. 36, No. 5-6, Apr. 1, 2005, pp. 773-784.
Yu, Long-Xi et al, "Expression of thermostable microbial cellulases in the chloroplasts of nicotine-free tobacco", Journal of Biotechnology, vol. 131, No. 3, Sep. 2007, pp. 362-369.
Leelavathi, Sadhu et al., "Overproduction of an alkali- and thermostable xylanase in tobacco chloroplasts and efficient recovery of the enzyme", Molecular Breeding, vol. 11, No. 1, Jan. 2003, pp. 59-67.
Verma, Dheeraj et al., "Chloroplast-derived enzyme cocktails hydrolyse lignocellulosic biomass and release fermentable sugars", Plant Biotechnology Journal, vol. 8, No. 3, Apr. 2010, pp. 332-350.
Dan, Siegel et al., "Cloning, Expression, Characterization, and Nucleophile Identification of Family 3, Aspergillus niger B-Glucosidase", The Journal of Biological Chemistry; Feb. 2000, vol. 275, No. 7, pp. 4973-4980.
McKenzie, Belinda, "Heterologous expression of cellulase enzymes in transplastidic Nicotiana tabacum cv. Petit Havana", Doctor of Philosophy Thesis, School of Applied Sciences, RMIT University, Jan. 2008.

* cited by examiner

Figure 2
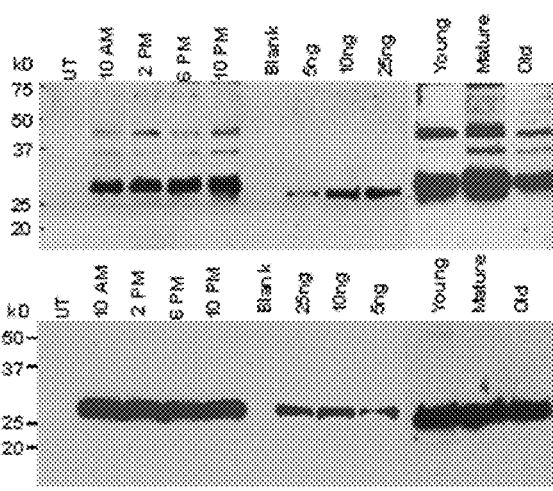
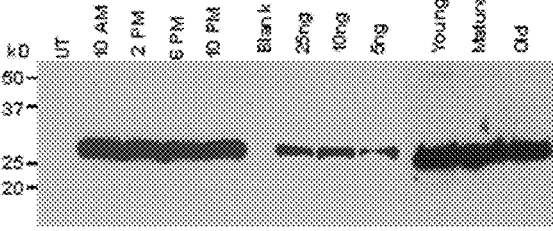
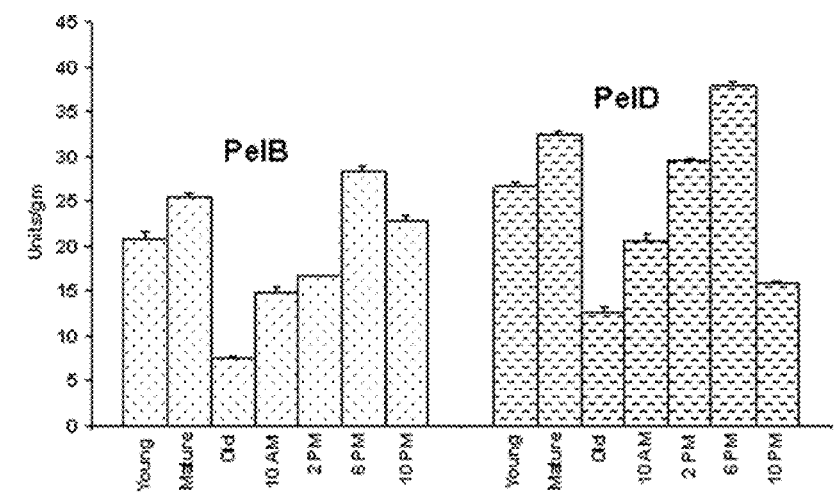
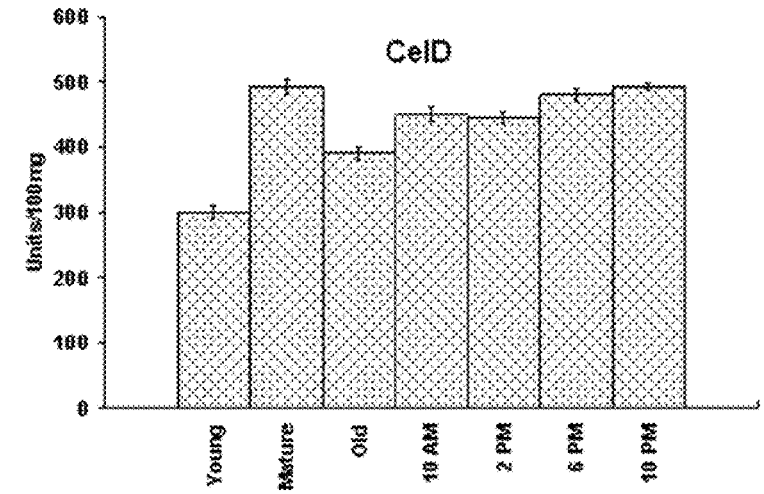

Figure 4
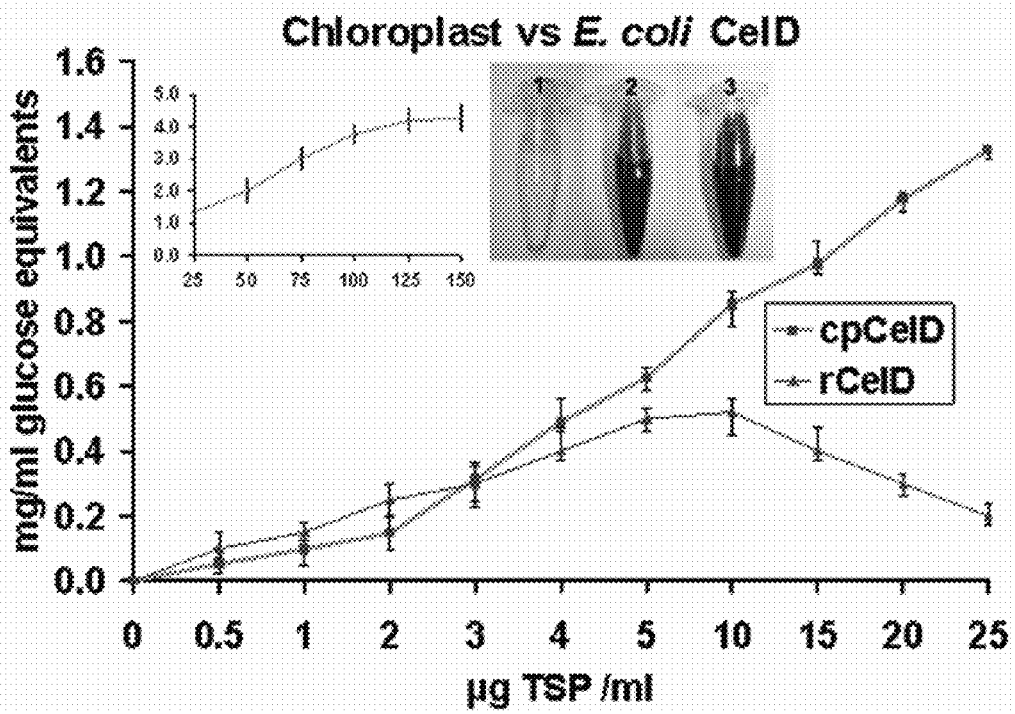
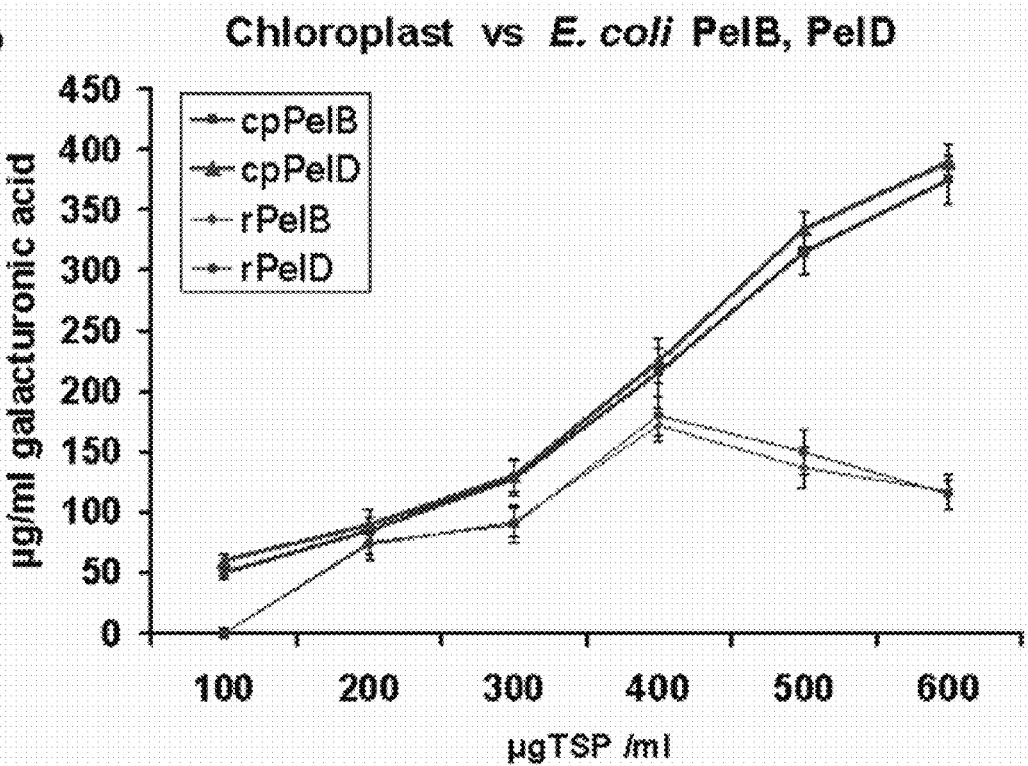

PRODUCTION AND USE OF PLANT DEGRADING MATERIALS

CROSS-REFERENCE TO RELATED APPLICATIONS

This application is related to U.S. Provisional Patent Application No. 61/032,536 filed Feb. 29, 2008 to which priority is claimed under 35 USC 119 and is incorporated by reference.

GOVERNMENT RIGHTS

This invention was made with government support under grant no. 2009-39200-19972 awarded by the United States Department of Agriculture/National Institute of Food and Agriculture; under grant no. GM063879 awarded by the National Institute of Health; and under grant no. 58-3611-7-610 awarded by the United States Department of Agriculture/Agricultural Research Service. The government has certain rights in the invention.

BACKGROUND

The composition and diversity of biomass for producing cellulosic ethanol requires multiple enzyme systems, in very high concentrations, to release constituent sugars from which cellulosic ethanol is made. All currently available enzymes for cellulosic ethanol are produced in expensive fermentation systems and are purified in a process very similar to biopharmaceuticals like insulin. Therefore, reagent grade enzymes for ethanol production are extremely expensive. For example, B-glucosidase, pectolyase and cellulase are currently sold by Novozyme through the Sigma catalog for $124,000, $412,000 and $40,490 per kg, respectively. These enzymes are sold as formulations to biorefineries without disclosing the actual enzyme components. Therefore, the actual cost for each enzyme, sold in bulk quantities, is not publicly available. Most industrial estimates for enzymes to produce cellulosic ethanol are in the $2 to $3 per gallon range, making large scale use cost prohibitive. Current capacity of fermentation systems will also be a major limitation. With increase in demand for enzymes and limited production capacity, the enzyme cost is likely to increase further.

A major limitation for the conversion of this biomass to ethanol is the high cost and large quantities of enzymes required for hydrolysis. B-glucosidase, pectolyase and cellulase are currently sold by Novozyme or other industries through the Sigma catalog for $124,000, $412,000 and $40,490 per kg, respectively. Therefore, the US DOE has long identified the cost of enzymes and their high loading levels required for most lingo-cellulosic feedstocks as one of the major barriers to cellulosic ethanol production. Currently, all commercially-available enzymes are produced through a fermentation process. Unfortunately, the building and maintenance of the fermentation production process is very expensive, costing $500M-$900M in upfront investment. No viable alternative to fermentation technology has yet emerged for mass-producing critical, yet prohibitively expensive industrial enzymes. This void in the marketplace for an alternative process is addressed directly by this proposal.

BRIEF DESCRIPTION OF DRAWINGS

FIG. 2 Western blot analysis and quantitation of transplastomic lines. Western blot of transplastomic lines expressing (a) PelB or (b) PelD. UT: untransformed, mature leaves harvested at 10 AM, 2 PM, 6 PM and 10 PM; 5 ng, 10 ng and 25 ng: PelA purified protein, young, mature and old leaves. (c) Enzyme units of PelB and PelD (c) or CelD (d) from one g or 100 mg leaf of different age or harvesting time.

FIG. 4 E. coli vs chloroplast derived enzymes at different protein concentrations of crude extracts. (a) Enzyme kinetics of cpCelD and rCelD using carboxymethyl cellulose (2%) substrate. The reaction mixture contained increasing concentration of cpCelD and rCelD TSP (μg/ml) with 10 mM $CaCl_2$ and 50 mM sodium acetate buffer, pH 6.0. Enzyme hydrolysis was carried out for 30 minutes at 60° C. Figure inset shows enzyme kinetics saturation point for cpCelD TSP amount (μg/ml) towards CMC (2%). Eppendorf tubes with reaction mixture shown in inset represents, 1 untransformed plant, 2 and 3 rCelD and cpCelD 10 μg TSP. (b) Effect of cpPelB, cpPelD, rPelB, and rPelD on hydrolysis of 5.0 mg/ml sodium polygalacturonate substrate. The reaction mixture contained increasing concentration of cpPelB, cpPelD, rPelB, and rPelD (μg/ml) in 20 mM Tris-HCl buffer (pH 8.0). Sodium polygalacturonate (Sigma) was measured using DNS method and measured from the D-galacturonic acid standard graph. Enzyme hydrolysis was carried out for 2 hour at 40° C. on rotary shaker at 150 rpm.

GENERAL DESCRIPTION

Figure 1:
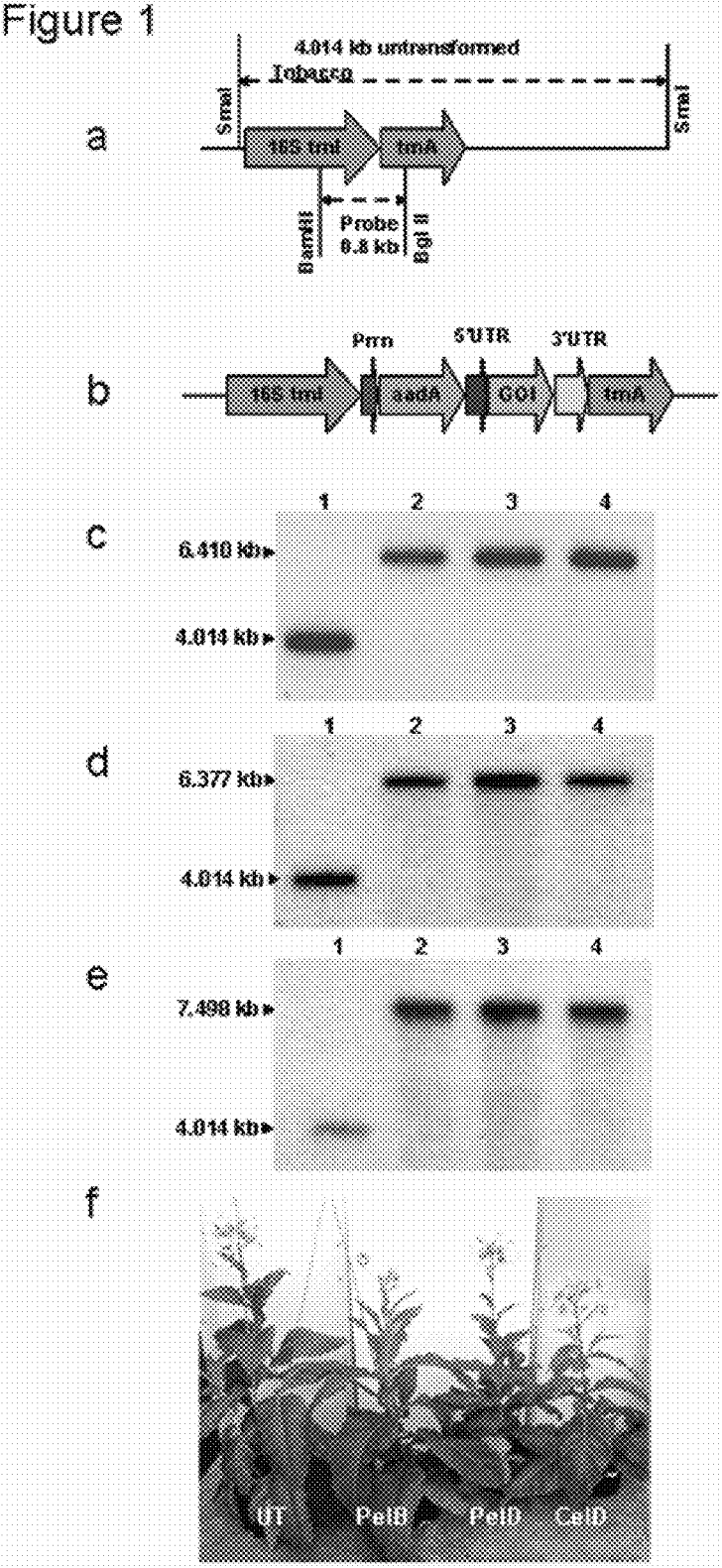
FIG. 1 (a) Schematic representation of the chloroplast 16S trnI/trnA region. Transgenes were inserted at the trnI/trnA spacer region in the tobacco chloroplast genome. (b) Schematic representation of the chloroplast transformation vectors. The gene of interest (GOI) is celD, celO, pelA, pelB, pelD, cutinase, lipY, egl1, egl, swo1, xyn2, axe1 or bgl1. Prrn, rRNA operon promoter; aadA, aminoglycoside 3'-adenylytransferase gene confers resistance to spectinomycin; 5' UTR, promoter and 5' untranslated region of psbA gene; 3' UTR, 3' untranslated region of psbA gene. (c) Evaluation of transgene integration and homoplasmy by Southern blot of pelB, (d) pelD and (e) celD transplastomic lines hybridized with the flanking sequence probe (1, untransformed; 2 to 4, transplastomic lines). (f) Phenotypes of untransformed (UT) and transplastomic lines grown in green house showing normal growth.

Certain embodiments of the invention address the major problems discussed above by producing all required enzymes in plants or bacteria or a combination of both, thereby dramatically alleviating the cost of fermentation and purification. According to one embodiment, the invention pertains to a method of degrading a plant biomass sample so as to release fermentable sugars therein. The method involves obtaining a plant degrading cocktail comprising at least two cell extracts, each cell extract having an active plant degrading compound that was recombinantly expressed in cells from which each said cell extract is derived. The at least two cell extracts are either plant extracts or bacterial extracts, or a combination of both. The plant degrading cocktail is admixed with the biomass sample to release fermentable sugars. In a more specific embodiment, the plant degrading cocktail includes cell extracts that include plant degrading enzymes such as cellulase, ligninase, beta-glucosidase, hemicellulase, xylanase, alpha amylase, amyloglucosidase, pectate lyase, lipase, maltogenic alpha-amylase, pectolyase, or compounds that facilitate access of such enzymes, or so called, accessory plant degrading compounds, including but not limited to cutinase or expansin (e.g. swollenin). The inventors have found that such accessory plant degrading compounds serve to facilitate the action of plant degrading enzymes which synergistically elevates the amount of fermentable sugars produced for any given biomass sample.

Plant cell extracts will in most cases include an amount of ribulose-1,5-bisphosphate carboxylase_oxygenase (rubisco) from the plant cells from the plant cell extracts are derived. Rubisco is the most prevalent enzyme on this planet, accounting for 30-50% of total soluble protein in the chloroplast; it fixes carbon dioxide, but oxygenase activity severely limits photosynthesis and crop productivity (Ogren, W. L. (2003) *Photosynth. Res.* 76, 53-63, 2. Spreitzer, R. J. & Salvucci, M. E. (2002) *Annu. Rev. Plant Biol.* 53, 449-475). Rubisco consists of eight large subunits (LSUs) and eight small subunits (SSUs). The SSU is imported from the cytosol, and both subunits undergo several posttranslational modifications before assembly into functional holoenzyme (Houtz, R. L. & Portis, A. R. (2003) *Arch. Biochem. Biophys.* 414, 150-158.).

The use of genetic transformation of plants is generally not considered a viable alternative to the conventional fermentation processes for producing plant degrading enzymes in light of the fact that the expressed proteins would be deleterious to plant life and growth. The inventors have endeavored to devise a method of expressing plant degrading enzymes in such a way that does not disrupt the plant cell. It is the inventors' belief that the present invention is the first demonstration of viable plant degrading enzyme expression in plants. The inventors have realized that the expression of many plant degrading enzymes can be expressed in chloroplasts without adverse effects on the plant. The chloroplasts appear to insulate the plant cell from damage from the enzymes. Though expression in chloroplasts is exemplified herein, unless specifically stated, embodiments of the present invention should not be construed to be limited to chloroplast expression of plant degrading enzymes. Certain embodiments related to a combination of plant and bacterial extracts from cells engineered to recombinantly express plant degrading compound(s).

The term "recombinantly expressed" as used herein refers to production of a polypeptide from a polynucleotide that is heterologous to the cell in which the polynucleotide has been transfected. Recombinant expression may result from heterologous polynucleotides that are stably transformed in the genome of the cell, or genome of the cell organelle, or which are merely present in the cell via a transfection event.

The term chloroplast is interpreted broadly to cover all plastids, including proplastids, etioplasts, mature chloroplasts, and chromoplasts.

A comprehensive cellulase system consists of endoglucanases, cellobiohydrolases and beta glucosidases. The cellobiohydrolases and endoglucanases work synergistically to degrade the cellulose into cellobiose, which is then hydrolysed to glucose by the beta glucosidases. Cellobiase, or beta-glucosidase, activity is responsible for the formation of glucose from cellobiose and plays an important role in cellulose degradation by relieving the end product (cellobiose) inhibition. Gene sequences for most of these enzymes, from different microorganisms, have been deposited in public data bases.

Pectins, or pectic substances, are collective names for a mixture of heterogeneous, branched and highly hydrated polysaccharides present as one of the major components in plant cell walls. These polysaccharides comprise mostly neutral sugars, such as arabinan, galactan, and arabino galactan. Activepectolytic enzyme preparations have the following enzymes: Two alpha-L-rhamnohydrolases, polygalacturonase, pectin methylesterase, endo-pectate lyase (pectintranseliminase), pectin lyase and small percent of xylanase. Nucleotide sequence for pectin degrading enzymes, xylanases, cellulases are available in public data bases. See Example 9 herein for discussion on sequences.

The inventor has realized that enzyme requirements are very different for each type of biomass used in cellulosic ethanol production. Accordingly, certain embodiments of the present invention relate to cocktails of enzymes obtained from plant expression and/or bacteria expression that the inventors have developed to be particularly effective for the targeted biomass material.

Biomass sources that can be degraded for ethanol production in accordance with the teachings herein, include, but are not limited to, grains such as corn, wheat, rye, barley and the grain residues obtained therefrom (primarily leftover material such as stalks, leaves and husks), sugar beet, sugar cane, grasses such as switchgrass and *Miscanthus*, woods such as poplar trees, eucalyptus, willow, sweetgum and black locust, among others, and forestry wastes (such as chips and sawdust from lumber mills). Other biomasses may include, but are not limited to, fruits including citrus, and the waste residues therefrom, such as citrus peel.

Throughout this document, tobacco is referred to as an exemplary plant for expressing plant degrading enzymes. However, unless specifically stated, embodiments of the invention should not be construed to be limited to expression in tobacco. The teachings of gene expression taught herein can be applied to a wide variety of plants, including but not limited to tobacco; lettuce, spinach; sunflower; leguminous crops such as soybean, beans, peas, and alfalfa; tomato; potato; carrot; sugarbeet; cruciferous crops; fibre crops such as cotton; horticultural crops such as gerbera and chrysanthemum; oilseed rape; and linseed.

In one embodiment, genes from *Aspergillusniger, Aspergillus aculeatus, Trichodermareesei* andor *Clostridium thermocellum* encoding different classes of enzymes are isolated using gene specific primers. In order to express different classes of genes in a chloroplast of interest, the following strategies are used. The chloroplast vector contains flanking sequences from the chloroplast genome to facilitate homologous recombination. In one embodiment, foreign genes are integrated individually into the spacer region of chloroplast genome. The coding sequence of different enzymes can be regulated by appropriate regulatory sequences. Recombinant plasmids will be bombarded into tobacco to obtain transplastomic plants.

In a specific embodiment, powdered tobacco leaves are used as enzyme sources for commercial evaluation of ethanol production from a biomass source. In a more specific embodiment, the biomass source is a grain such as corn, a grass, or is citrus waste.

For chloroplasts that are transformed, it has been realized that obtaining homplasmy with respect to the transgenic chloroplasts is desired. The transgene integration and homoplasmy is confirmed by PCR and Southern blot analysis, respectively. Expression of the transgenes is confirmed by western blot analysis and quantified by ELISA. The protein extract from transplastomic tobacco plants is tested for its ability to degrade citrus waste biomass. Based on the results, more enzyme classes are added to increase the breakdown of plant biomass to sugars for fermentation to ethanol. Each tobacco plant, engineered to produce an enzyme, will be able produce a million seeds, to facilitate scale up to 100 acres, if needed. Homogenized plant material, such as powdered tobacco leaves or plant extracts, or purified enzymes from plant material are used as the enzyme source for commercial evaluation of ethanol production from citrus waste.

While current methods involve placing a foreign gene in the plant cell nucleus, CT transforms the genome of the approximately 100 chloroplasts that are within each tobacco plant cell. Each tobacco plant chloroplast contains about 100 copies of the chloroplast's genetic material, so the amount of protein (in this case, enzyme proteins used to break down biomass into sugar for ethanol production) is increased exponentially. This is the primary reason why massive volume production of cell wall degrading enzymes for cellulosic ethanol production is so cost effective. Secondly, tobacco has large volume biomass (40 metric tons of leaves per acre) and it can be harvested multiple times during a given growing season in Florida. And, as previously mentioned, it is easy to plant 100 acres from a single tobacco plant. Lastly, because chloroplasts are inherited maternal, they are not functional in the tobacco plant's pollen.

According to one embodiment, the invention pertains to a method of degrading a plant biomass sample to release fermentable sugars. The method includes obtaining a plant degrading cocktail having at least one chloroplast genome or genome segment having a heterologous gene that encodes cellulase, ligninase, beta-glucosidase, hemicellulase, xylanase, alpha amylase, amyloglucosidase, pectate lyase, cutinase, lipase or pectolyase, or a combination thereof, and wherein said plant material has cellulase, ligninase, beta-glucosidase, hemicellulase, xylanase, alpha amylase, amyloglucosidase, pectate lyase, cutinase, lipase, maltogenic alpha-amylase, pectolyase or expansin, or a combination thereof, that has been expressed in a plant from which said plant material is derived; and admixing said plant degrading material with said biomass sample. In a more specific embodiment, the enzyme or combination of enzymes pertains to more than 0.1 percent of the total protein in the plant material.

According to another embodiment, the invention pertains to a method of producing a plant biomass degrading material sufficient to release fermentable sugars, the method including producing at least one plant comprising chloroplasts that express cellulase, ligninase, beta-glucosidase, hemicellulase, xylanase, alpha amylase, amyloglucosidase, pectate lyase, cutinase, lipase, maltogenic alpha-amylase, pectolyase, or expansin, or a combination thereof; harvesting said plant; and processing said plant to produce an enzyme source suitable for mixing with and degrading a biomass sample. In a specific embodiment the plant is tobacco; lettuce, spinach; sunflower; fibre crops such as cotton; horticultural crops such as gerbera and chrysanthemum; leguminous crops such as soybean, beans, peas, and alfalfa; tomato; potato; sugarbeet; cruciferous crops, including oilseed rape; and linseed. In a more specific embodiment, plant is tobacco.

One aspect of the invention is to provide an abundant inexpensive source of enzyme for degrading biomass. Accordingly, the plant or bacterial material in which plant degrading compounds have been expressed may be processed by drying and powderizing the plant or a portion thereof. In another embodiment, crude liquid extracts are produced from the plant and/or bacterial material. In alternative embodiments, the plant degrading material may be enzymes that have been purified fully or partially from the plant and/or bacteria in which they are expressed. However, providing the plant degrading material as a dry form or as crude extract of the plant and/or bacterial material avoids the need for time-consuming and potentially expensive purification steps. In this way, the plant material has a longer shelf life and may easily be mixed with the plant biomass sample according to conventional plant degrading and fermenting processes.

In one specific embodiment, the method of producing a plant entails producing a first plant with chloroplasts transformed to express a first enzyme and a second plant with chloroplasts transformed to express a second enzyme. Plant material from both first and second plants may be combined to produce a plant degrading sample that includes more than one plant degrading enzyme. In a more specific embodiment, the invention pertains to a method of producing a plant that entails at least two of the following: producing a first plant comprising chloroplasts that express cellulase, producing a second plant comprising chloroplasts that express lignanse, producing a third plant comprising chloroplasts that express beta-glucosidase; producing a fourth plant comprising chloroplasts that express hemicellulase; producing a fifth plant comprising chloroplasts that express xylanase; producing a sixth plant comprising chloroplasts that express alpha-amylase; producing a seventh plant comprising chloroplasts that express amyloglucosidase; producing an eighth plant comprising chloroplasts that express pectate lyase; producing a ninth plant comprising chloroplasts that express cutinase; producing a tenth plant comprising chloroplasts that express lipase; producing an eleventh plant comprising chloroplasts that express maltogenic alpha amylase, producing a twelfth plant comprising chloroplasts that express pectolyase and/or a thirteenth plant comprising chloroplasts that express expansin (e.g. swollenin).

As alluded to above, the inventors have recognized that according to certain embodiments, plant derived enzymes are augmented with plant degrading enzymes recombinantly expressed in bacteria. Thus, a plant degrading cocktail may include enzymes recombinantly expressed in plants and enzymes that are recombinantly expressed in bacteria, such as but not limited to E. coli.

According to a further embodiment, the invention pertains to a plant material useful for degrading a plant biomass, the material including at least one chloroplast genome or genome segment having a heterologous gene that encodes cellulase, ligninase, beta-glucosidase, hemicellulase, xylanase, alpha amylase, amyloglucosidase, pectate lyase, cutinase, lipase, maltogenic alpha-amylase, pectolyase, or expansin, or a combination thereof; and wherein said plant material comprises cellulase, ligninase, beta-glucosidase, hemicellulase, xylanase, alpha amylase, amyloglucosidase, pectate lyase, cutinase, lipase, maltogenic alpha-amylase, pectolyase, or expansin, or a combination thereof. In a more specific embodiment, the plant material includes at least two of the following: a first chloroplast genome or genome segment having a heterologous gene that encodes cellulase, a second chloroplast genome or genome segment having a heterologous gene that encodes lignanse, a third chloroplast genome or genome segment having a heterologous gene that encodes beta-glucosidase; a fourth chloroplast genome or genome segment having a heterologous gene that encodes hemicellulase; a fifth chloroplast genome or genome segment having a heterologous gene that encodes xylanase; a sixth chloroplast genome or genome segment having a heterologous gene that encodes alpha-amylase; a seventh chloroplast genome or genome segment having a heterologous gene that encodes amyloglucosidase; an eighth chloroplast genome or genome segment having a heterologous gene that encodes pectate lyase; a ninth plant chloroplast genome or genome segment having a heterologous gene that encodes cutinase; a tenth chloroplast genome or genome segment having a heterologous gene that encodes lipase; an eleventh chloroplast genome or genome segment that encodes maltogenic alpha-amylase, a twelfth chloroplast genome or genome segment having a heterologous gene that encodes pectolyase and a thirteenth chloroplast genome or genome segment having a heterologouse gene that encodes expansin (e.g. swollenin).

According to another embodiment, the invention pertains to a plant having a plant cell having a more than natural amount of cellulase, ligninase, beta-glucosidase, hemicellulase, xylanase, alpha amylase, amyloglucosidase, pectate lyase, cutinase, lipase pectolyase or expansin, or a combination thereof, and wherein said plant material comprises cellulase, ligninase, beta-glucosidase, hemicellulase, xylanase, alpha amylase, amyloglucosidase, pectate lyase, cutinase, lipase, pectolyase, or expansin, or a combination thereof, active enzyme therein. In a more specific embodiment, the enzyme or combination of enzymes represents is more than 0.1 percent of the total protein of the cell. In an even more specific embodiment the enzyme or combination of enzymes represent more than 1.0 percent of the total protein in the cell.

In a further embodiment, the invention pertains to a plant derived composition comprising cellulase, ligninase, beta-glucosidase, hemicellulase, xylanase, alpha amylase, amyloglucosidase, pectate lyase, cutinase, lipase, maltogenic alpha-amylase, pectolyase and/or swollenin, and an amount of rubisco. In a specific embodiment, the rubisco to enzyme ratio ranges from 99:1 to 1:99.

In an additional embodiment, the invention pertains to commercial cultivars that recombinantly express one or more plant degrading compounds. Commercial cultivars of tobacco, such as, but not limited to, LAMD and TN90, produce substantially more leaf material than experimental cultivars. However, commercial cultivars are more sensitive to introduction of foreign genes. Surprisingly, the inventor, through significant trial and error, has been able to successfully transfect cells and induce expression of plant degrading compounds in commercial cultivars.

EXAMPLES

Example 1: Assembly of Chloroplast Expression Constructs

For the integration of transgenes, transcriptionally active spacer region between the trnI and trnA genes was used (FIG. 1a). PCR resulted in the amplification of various genes of interest (GOI) including endoglucanase (celD), exoglucanase (celO) from *Clostridium thermocellum* genomic DNA, lipase (lipY) from *Mycobacterium tuberculosis* genomic DNA, pectate lyases (pelA, pelB, pelD) and cutinase from *Fusarium solani*. Using a novel PCR based method, coding sequences of GOI including endoglucanases (egl1 and egI), swollenin (swo1 similar to expansins), xylanase (xyn2), acetyl xylan esterase (axe1) and beta glucosidase (bgl1) were cloned without introns (ranging from 1-5) from *Trichoderma ressei* genomic DNA. Tobacco chloroplast transformation vectors were made with each GOI (FIG. 1b). All chloroplast vectors included the 16S trnI/trnA flanking sequences for homologous recombination into the inverted repeat regions of the chloroplast genome and the aadA gene conferring resistance to spectinomycin. The aadA gene was driven by the constitutive rRNA operon promoter with GGAGG ribosome binding site. The GOI was driven by the psbA promoter and 5' UTR in order to achieve high levels of expression. The 3' UTR located at the 3' end of the GOI conferred transcript stability.

Example 2: Generation and Characterization of Transplastomic Tobacco Expressing Pectate Lyases (PelB & PelD) and Endoglucanase (CelD)

Transplastomic tobacco plants were obtained as described previously[28, 29]. Southern blot analysis was performed to confirm site specific integration of the pLD-pelB, pLD-pelD and pLD-celD cassettes into the chloroplast genome and to determine homoplasmy. Digestion of total plant DNA with SmaI from untransformed and transplastomic lines generated a 4.014 kb fragment untransformed (UT) or 6.410 kb in pelB, 6.377 kb in pelD or 7.498 kb fragment in celD when hybridized with the [$^{32}$P]-labeled trnI-trnA probe, confirming site specific integration of the transgenes into the spacer region between the trnI and trnA genes (FIG. 1c-e). Furthermore, the absence of a 4.014 kb fragment in the transplastomic lines confirmed that homoplasmy was achieved (within the levels of detection). The phenotypes of transplastomic lines appeared to be normal when compared to untransformed plants and were fertile (produced flowers, seeds FIG. 1f).

Immunoblots with antibodies raised against PelA showed that PelB and PelD are immunologically related to PelA[30]. Therefore, PelA antibody was used to detect the expression of PelB and PelD, although their affinity was variable in transplastomic lines. All transplastomic lines showed expression of PelB or PelD protein. Expression levels did not change significantly corresponding to their enzyme activity depending on the time of harvest even though the PelB and PelD are regulated by light (FIG. 2a,b). This may be because of variable affinity between antigen epitopes of PelB, PelD and PelA antibody. Enzyme concentration slightly changed with leaf age and decreased in older leaves (FIG. 2a,b).

Example 3: Quantification of Pectate Lyases (PelB, PelD), and Endoglucanase (CelD) at Different Harvesting Time and Leaf Age The activity of the enzyme varied significantly depending on the developmental stages and time of leaf harvest. Maximum enzyme activity was observed in mature leaves of PelB, PelD and CelD, with reduced activity in older leaves (FIG. 2c,d). Mature leaves harvested at 6 PM showed maximum activity in both PelB and PelD whereas CelD showed maximum activity at 10 PM (FIG. 2c,d). This may be due to increased stability of endoglucanase against proteases in plant extracts. Activity of cpCelD did not significantly decrease in plant crude extracts stored at room temperature, for more than thirty days (data not shown).

CelD enzyme activity was calculated using DNS reagent[31] according to the IUPAC protocol[32]. The specific activity of cpCelD using 2% CMC substrate was 493 units/mg total soluble protein (TSP) or 100 mg leaf tissue, in crude extracts prepared from mature leaves harvested at 10 PM. Using the glucose hexokinase assay, which is highly specific for glucose, the specific activity was 4.5 units/mg TSP and 6.28 units/mg TSP, when 5% avicel and sigmacell solution respectively was used as substrate (at pH 6.0, 60° C.). Commercial cellulase enzyme (*Trichoderma reesei*, EC 3.2.1.4, Sigma) gave 4.2 units/mg and 3.43 units/mg solid for the same substrate. FIGS. 2c and 2d show that approximately 26 units, 32 units and 4,930 units of PelB, PelD and CelD were obtained per gram fresh weight of mature leaves harvested at 6 PM or 10 PM. Thus, 2,048, 2,679 and 447,938 units of PelB, PelD and CelD can be harvested from each tobacco plant (experimental cultivar, Petit Havana). With 8,000 tobacco plants grown in one acre of land, 16, 21 and 3,584 million units of PelB, PelD or CelD can be obtained per single cutting (Table 1). Based on three cuttings of tobacco in one year, up to 49, 64 and 10,751 million units of PelB, PelD or CelD can be harvested each year. The commercial cultivar yields 40 metric tons biomass of fresh leaves as opposed to 2.2 tons in experimental cultivar Petit Havana. Therefore, the commercial cultivar is expected to give 18 fold higher yields than the experimental cultivar.

Figure 3:
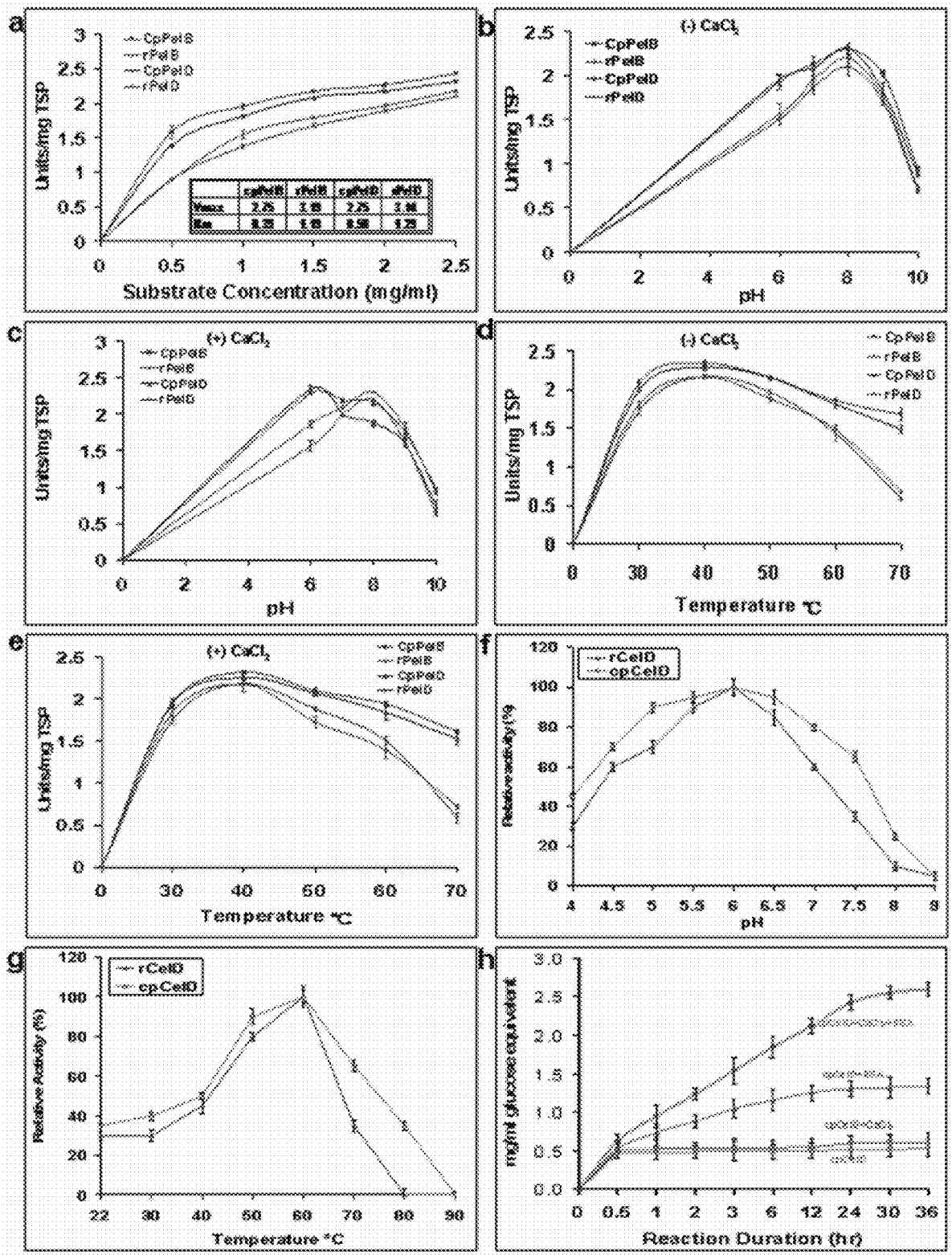
FIG. 3 Effect of substrate, pH, temperature and cofactors on cpPelB, rPelB, cpPelD, rPelD, rCelD and cpCelD enzyme activity. (a) Effect of increasing PGA concentration on pectate lyases activity. (b) Effect of pH on pectate lyases activity in the absence of $CaCl_2$ and (c) in the presence of $CaCl_2$. The buffers used were following: 50 mM phosphate buffer (pH 6-7), Tris-HCl buffer (pH 8), glycine/NaOH buffer (pH 9) and CAPS buffer (pH 10.0) with 4 μg of TSP of PelB and PelD from both plant and E. coli. The optimal pH was determined at 40° C. using 2.5 mg/ml PGA as a substrate. (d) Effect of temperature (30-70° C.) on enzyme activity at pH 8.0 in the absence of $CaCl_2$ and (e) in the presence of $CaCl_2$. (f) Optimization of pH for cpCelD and rCelD activity using CMC (2%) at 60° C. for 30 minutes. Relative activity (%) was measured with reference to maximum activity obtained with 25 μg/ml for cpCelD and 10 μg/ml for rCelD (g) Effect of increasing temperature on relative activity of cpCelD and rCelD using CMC (2%) for 30 minutes at pH 6.0. Relative activity (%) was measured with reference to maximum activity obtained with 25 μg/ml for cpCelD and 10 μg/ml for rCelD (h) Enhancement of cpCelD (25 μg TSP/ml reaction) activity using 10 mM $CaCl_2$ and 20 μg/ml BSA individually or in combination with 50 mM sodium acetate during the prolonged enzymatic hydrolysis. The hydrolysis was carried out up to 36 hours at 60° C., pH 6.0 in the presence of CMC (2%)

Example 4: Effect of pH & Temperature on Pectate Lyases (PelB & PelD) and Endoglucanase (CelD) Enzyme Activity Both plant and *E. coli* extracts showed optimal activity at 2.5 mg/ml PGA (FIG. 3a). Therefore, all enzyme characterization studies were performed at this substrate concentration. Kinetic studies carried out by using 4 µg of TSP, with increasing concentration of PGA (0-2.5 mg), under standard assay conditions gave Km values of 0.39 and 1.19 µg/ml in chloroplast (cp) and *E. coli* (r) PelB respectively, whereas values for chloroplast and *E. coli* PelD were 0.50 and 1.29 µg/ml respectively. The Vmax values obtained were 2.75, 3.19, 2.75 and 3.14 units/mg for cpPelB, rPelB, cpPelD and rPelD, respectively (FIG. 3a).

The crude extract (4-5 µg TSP) from plant or *E. coli* was used to study the effect of pH and temperature on the activity of enzymes. The optimal temperature for the *E. coli* and chloroplast derived pectate lyase under the standard assay conditions was 40° C. and the optimal pH was 8.0. Plant derived pectate lyases showed a pH optimum of 6.0 in the presence of 1 mM CaCl$_2$. The *E. coli* crude extracts showed an optimal pH of 8.0 irrespective of presence or absence of CaCl$_2$ in the reaction (FIG. 3b,c). The temperature increase had minimal effect on the activity of plant derived pectate lyases, whereas the *E. coli* enzyme showed comparatively lower activity at higher temperatures (FIG. 3d,e). These differences in enzyme properties from two different hosts may be due to their folding. This possibility was supported by the observation that it was possible to detect the *E. coli* enzyme with HIS-tag antibody but not the chloroplast enzyme (data not shown). It is well known that foreign proteins form disulfide bonds in chloroplasts[33-35] but not in *E. coli* when expressed in the cytoplasm. Both PelB and PelD enzymes have even number (12 or 14) cysteines that could form disulfide bonds[30].

CpCelD activity with 2% CMC was measured at different pH and temperature. The cpCelD showed pH optima between pH 5.0 to pH 7.0 (FIG. 3f) whereas E. coli enzyme had a pH optimum of 6.5. Temperature optima was between 50-60° C. for E. coli and 50-70° C. for plant enzyme (FIG. 3g). Clostridium thermocellum CelD is structurally known to have affinity for $CaCl_2$ ions and it also provided thermostability[36]. Even though 10 mM $CaCl_2$ increased CelD activity in 2% CMC to 2 fold in E. coli crude extract, this was not apparent in chloroplast CelD crude extract during initial period of incubation. This may be due to optimum concentration of calcium ion present in plant cells. However, $CaCl_2$ with 20 µg BSA yielded 5 fold increased activity at the end of 24 hour incubation for cpCelD crude extract (FIG. 3h).

Example 5: E. coli vs Chloroplast CelD, PelB & PelD

E. coli crude extract containing CelD enzyme showed decrease in enzyme activity when the reaction mixture contained more than 10 µg TSP, where as plant crude extract containing CelD released more reducing sugar with increasing protein concentration (FIG. 4a). Chloroplast expressed CelD activity was saturated (in 2% CMC) at 150 µg TSP (FIG. 4a inset) and there was no decrease in chloroplast CelD enzyme activity even up to 500 µg TSP as determined by end point assay. These results show that crude plant extracts containing cpCelD can be directly used for biomass degradation without any need for purification whereas E. coli extracts probably contain endoglucanase inhibitors. Similarly, at higher protein concentrations, E. coli expressed rPelB and rPelD showed reduced pectate lyase activity whereas cpPelB or cpPelD continued to increase activity even up to 600 µg TSP (FIG. 4b). There may be inhibitors of pectate lyase in E. coli extracts, which are not present in plant crude extracts. This finding is potentially of high practical significance because use of crude extracts eliminates the need for purification of enzymes. Large amounts of crude plant enzyme can be utilized in the cocktail as shown below without causing detrimental effect on enzyme activity, hydrolysis or yield of end products.

Example 6: Enzyme Cocktail for Hydrolysis of Filter Paper

Figure 5:
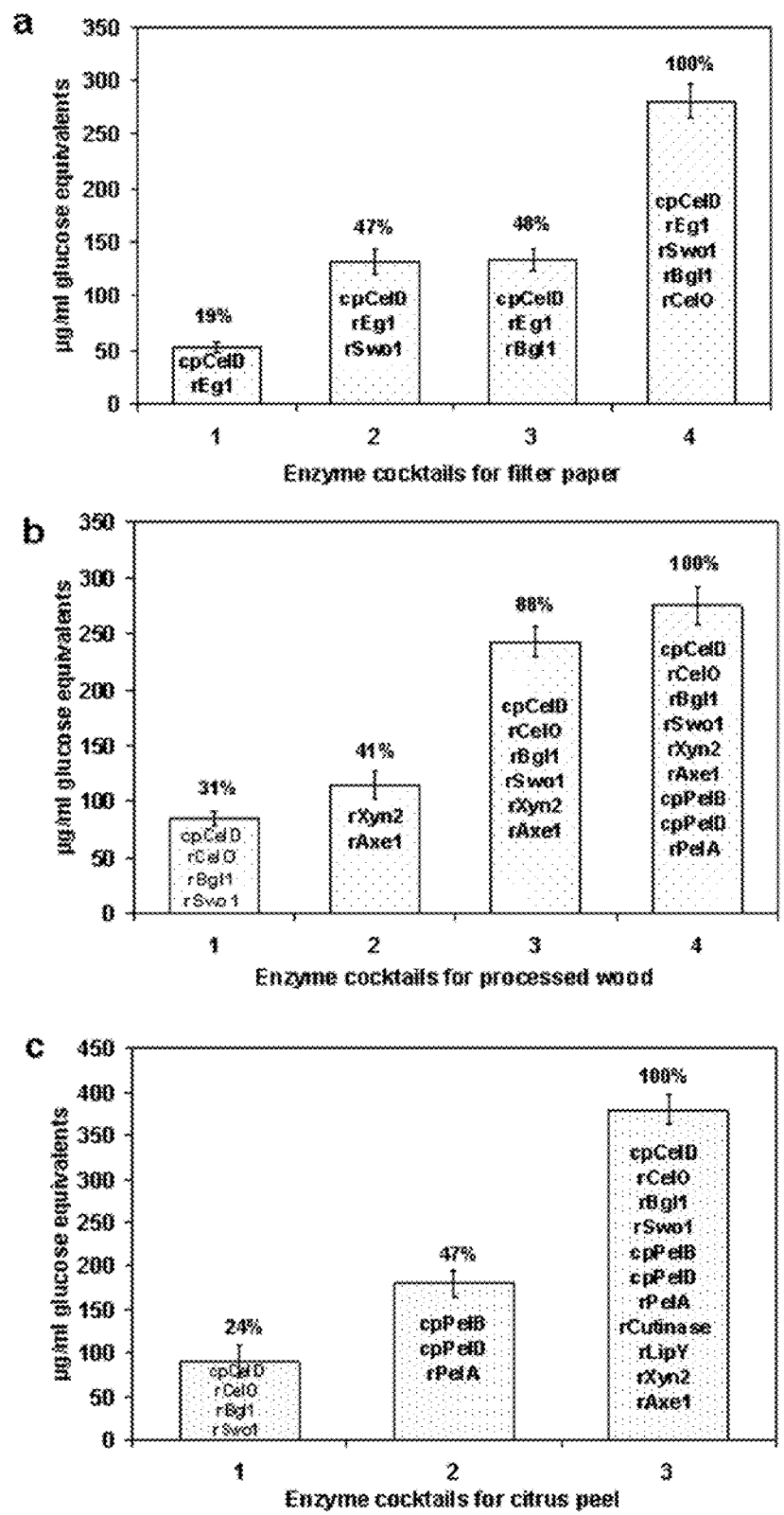
FIG. 5 Enzyme cocktails for filter paper, processed wood and citrus peel. (a) Filter paper activity was determined using Whatman No. 1 filter paper strip (50 mg/ml assay) at pH 5.5 and 50° C. Different combinations of crude extracts containing rEg1 (100 μg/ml), rBgl1 (200 μg/ml), rSwo1 (120 μg/ml), rCelO (100 μg/ml) and cpCelD (100 μg/ml) were used in the cocktail. The samples were incubated with 10 mM $CaCl_2$, 20 μg BSA in a rotary shaker at 150 rpm for 24 hours. (b) Hydrolysis of processed wood sample (200 mg/5 ml reaction) was done by using a cocktail of crude extracts of cpPelB (250 μg/ml), cpPelD (250 μg/ml) (at pH 8.0), cpCelD (200 μg/ml), cpXyn2 (200 μg/ml), rEg1 (100 μg/ml), rBgl1 (200 μg/ml), rSwo1 (120 μg/ml), rCelO (100 μg/ml), rAxe1 (100 μg/ml), rPelA (200 μg/ml), rCutinase (50 μg/ml), rLipY (100 μg/ml). The reaction mixture containing 10 mM $CaCl_2$, 20 μg/ml BSA was incubated for 36 hours in a rotary shaker at 150 rpm; pH (5.5-8.0) and temperature (40° C.-50° C.) were adjusted based on optimal conditions. Endpoint analysis of release of glucose equivalents was determined using DNS method. (c) Hydrolysis of Valencia orange peel (200 mg/5 ml reaction) was done using a cocktail of crude extracts of cpPelB (250 μg/ml), cpPelD (250 μg/ml) cpCelD (100 μg/ml) and cpXyn2 (100 μg/ml), reg1 (100 μg/ml), rBgl1 (200 μg/ml), rSwo1 (120 μg/ml), rCelO (100 μg/ml) and cpCelD (100 μg/ml), rAxe2 (100 μg/ml), rCutinase (50 μg/ml), rLipY (100 μg/ml), rPelA (200 μg/ml). End product analysis of reducing sugar was determined using DNS reagent[31] and D-glucose and D-galacturonic acid as standards. Ampicillin and kanamycin 100 μg/ml was added to prevent any microbial growth during hydrolysis. The samples were incubated with 10 mM $CaCl_2$, 20 μg/ml BSA in a rotary shaker at 150 rpm for 24 hours; pH (5.5-8.0) and temperature (40° C.-50° C.) were adjusted based on optimal conditions. In all experiments control assays contained substrate without enzyme or enzyme without substrate. All experiments and assays were carried out in triplicate.

Before evaluation of enzyme cocktails, activity of each enzyme was tested independently with an appropriate substrate. Chloroplast or E. coli expressed endoglucanase (cpCelD or rEg1) alone did not release any detectable glucose from filter paper but when mixed together up to 19% of total hydrolysis was observed (FIG. 5a, bar1). This could be due to different carbohydrate binding domains of endoglucanases towards filter paper. The synergistic activity was further enhanced up to 47 or 48% when the endoglucanases (cpCelD and rEg1) were mixed with swollenin (rSwo1) or beta-glucosidase (rBgl1, FIG. 5a, bar2&3). Addition of cellobiohydrolase (rCelO) to this cocktail doubled the hydrolysis of filter paper, releasing maximum amount of reducing sugar (FIG. 5a, bar4). This synergism observed was probably due to the exo-mode of action of cellobiohydrolase[37] from reducing ends that were formed by random cuts in cellulose chains through endoglucanases (cpCelD and rEg1), along with the action of expansin and beta-glucosidase.

Example 7: Enzyme Cocktail for Hydrolysis of Processed Wood Sample

The enzyme cocktail that released highest glucose equivalents with filter paper (except rEg1) was tested on processed wood substrate. After 24 hour hydrolysis, 31% of total hydrolysis was observed with this cocktail (FIG. 5b, bar1). An enzyme cocktail of endoxylanase and acetyl xylan esterase showed 41% of total hydrolysis (FIG. 5b, bar2). When these two cocktails were combined together, the hydrolysis increased up to 88% (FIG. 5b, bar3). When processed wood substrate was first treated with pectate lyases, followed by the addition of the enzyme cocktail in bar 3, the overall hydrolysis was further enhanced, with release of up to 275 µg of glucose after 36 hour incubation (FIG. 5b, bar4). Addition of cutinase and lipase enzyme extracts (both with lipase activity) did not have significant effect on the release of fermentable sugars (data not shown). Novozyme 188 enzyme cocktail did not yield any detectable glucose equivalents from processed wood, whereas Celluclast 1.5 L yielded 10% more than the crude extract cocktail, with equivalent enzyme units based on CMC hydrolysis.

According to one embodiment, the invention pertains to a method for digesting a wood-based biomass sample comprising obtaining a plant material comprising endoxylanase or acetyl xylan esterase, or a combination thereof, that has been expressed in a plant from which all or a portion of said plant material is derived; and admixing said plant material with said wood based biomass sample. The method of this embodiment may further include admixing with the wood-based biomass sample, either prior to or contemporaneous to, admixture with the endoxylanase and/or acetyl xylan esterase plant material, a plant material comprising a pectate lyase that has been expressed in a plant from which all or a portion of said plant material is derived. The plant material may comprise rubisco.

Another embodiment pertains to a plant degrading enzyme cocktail useful in digesting a wood-based biomass sample comprising cellulase, beta-glucosidase, xylanase, alpha amylase, amyloglucosidase, pectin lyase, swollenin or pectate lyase, or a combination thereof expressed in a plant, optionally with an amount of rubisco.

Example 8: Enzyme Cocktail for Hydrolysis of Citrus Waste

The enzyme cocktail of endoglucanase (cpCelD), exoglucanase, swollenin and beta-glucosidase released up to 24% of total hydrolysis with citrus peel (FIG. 5c, bar1). When citrus peel was treated with pectate lyases (cpPelB, cpPelD and rPelA), hydrolysis was doubled (FIG. 5c, bar2). Pectate lyases contributed to 47% of total hydrolysis in this cocktail because of high pectin content (23%) in citrus peel[41]. Addition of endoxylanase, acetyl xylan esterase, cutinase and lipase to the both these cocktails released up to 360 µg/ml glucose equivalents from 100 mg ground citrus peel after 24 hour incubation period (FIG. 5c, bar3). Enzymes like cutinase and lipase may have hydrolyzed oil bodies present in the citrus peel, providing greater access to endoglucanase, endoxylanase and pectate lyases for efficient hydrolysis of citrus peel. Novozyme 188 enzyme cocktail yielded 11% more glucose equivalents with citrus peel, whereas Celluclast 1.5 L yielded 137% more than the crude extract cocktail with equivalent enzyme units based on CMC hydrolysis.

According to one embodiment, the invention pertains to a method for digesting a citrus biomass sample comprising obtaining a plant material comprising cellulase, beta-glucosidase, xylanase, alpha amylase, amyloglucosidase, pectin lyase or pectate lyase, or a combination thereof, that has been expressed in a plant from which all or a portion of said plant material is derived; and admixing said plant material with said citrus biomass sample.

Another embodiment pertains to a plant degrading enzyme cocktail useful in digesting a citrus biomass sample comprising cellulase, beta-glucosidase, xylanase, alpha amylase, amyloglucosidase, pectin lyase, swollenin or pectate lyase, or a combination thereof expressed in a plant, optionally with an amount of rubisco.

Methods Related to Examples 1-8

Isolation of Genes and Construction of Plastid Transformation Vectors

Genomic DNA of *Clostridium thermocellum* and *Trichoderma reesei* was obtained from ATCC and used as template for the amplification of different genes. Gene specific primers using a forward primer containing a NdeI site and a reverse primer containing a XbaI site for cloning in the pLD vector were designed for celD, celO and lipY genes. The mature region of cellulose genes celD (X04584) and celO (AJ275975) were amplified from genomic DNA of *Clostridium thermocellum*. LipY (NC_000962) was amplified from genomic DNA of *Mycobacterium tuberculosis*. Overlapping primers were designed for the amplification of various exons of egl1 (M15665), egI (AB003694), swoI (AJ245918), axe1 (Z69256), xyn2 (X69574) and bgl1 (U09580) from genomic DNA of *Trichoderma reesei* using a novel method. Full length cDNA of these genes was amplified from different exons by a novel PCR based method using the forward of first exon and reverse of last exon containing a NdeI site and XbaI site respectively. Pectate lyase genes pelA, pelB & pelD from *Fusarium solani* with similar restriction sites were amplified using gene specific primers from pHILD2A, pHILD2B[30] and pHILD2D[45] respectively. A similar strategy was used to amplify cutinase gene[46] from recombinant clone of *Fusarium solani*. All the full length amplified products were ligated to pCR Blunt II Topo vector (Invitrogen) and were subjected to DNA sequencing (Genewiz). Each gene cloned in Topo vector was digested with NdeI/XbaI and inserted into the pLD vector[17, 47] to make the tobacco chloroplast expression vector.

Regeneration of Transplastomic Plants and Evaluation of Transgene Integration by PCR and Southern Blot

*Nicotiana tabacum* var. Petite Havana was grown aseptically on hormone-free Murashige and Skoog (MS) agar medium containing 30 g/l sucrose. Sterile young leaves from plants at the 4-6 leaf stages were bombarded using gold particles coated with vector pLD-PelB, pLD-PelD and pLD-CelD and transplastomic plants were regenerated as described previously[28, 29]. Plant genomic DNA was isolated using Qiagen DNeasy plant mini kit from leaves. PCR analysis was performed to confirm transgene integration into the inverted repeat regions of the chloroplast genome using two sets of primers 3P/3M and 5P/2M, respectively[17]. The PCR reaction was performed as described previously[17, 29]. Leaf from the PCR positive shoots were again cut into small pieces and transferred on RMOP (regeneration medium of plants) medium containing 500 mg/l spectinomycin for another round of selection and subsequently moved to MSO (MS salts without vitamins and growth hormones) medium containing 500 mg/l spectinomycin for another round of selection to generate homoplasmic lines. Southern blot analysis was performed to confirm homoplasmy according to lab protocol[48]. In brief, total plant genomic DNA (1-2 μg) isolated from leaves was digested with SmaI and hybridized with $^{32}P$ α[dCTP] labeled chloroplast flanking sequence probe (0.81 kb) containing the trnI-trnA genes. Hybridization was performed by using Stratagene QUICK-HYB hybridization solution and protocol.

Immunoblot Analysis

Approximately 100 mg of leaf was ground in liquid nitrogen and used for immunoblot analysis as described previously[48]. Protein concentration was determined by Bradford protein assay reagent kit (Bio-Rad). Equal amounts of total soluble protein were separated by SDS-PAGE and transferred to nitrocellulose membrane. The transgenic protein expression was detected using polyclonal serum raised against PelA in rabbit.

*E. coli* Enzyme (Crude) Preparation

*E. coli* strain (XL-10 gold) harboring chloroplast expression vectors expressing rCelD, rEg1 (EC 3.2.1.4), rCelO (EC 3.2.1.91), rXyn2 (EC 3.2.1.8), rAxe1 (EC 3.1.1.72), rBgl1 (EC 3.2.1.21), rCutinase (EC 3.1.1.74), rLipY (lipase, EC 3.1.1.3), rPelA, rPelB, rPelD (EC 4.2.2.2) or rSwo1 was grown overnight at 37° C. Cells were harvested at 4° C. and sonicated four times with 30 s pulse in appropriate buffer (50 mM sodium acetate buffer with pH 5.5 for CelD, Eg1, CelO, Swo1, Xyn2, Axe1, Bgl1, 100 mM Tris-Cl with pH 7.0 for cutinase, lipase, PelA, PelB and PelD) containing protease inhibitor cocktail (Roche) and sodium azide (0.02%). Supernatant was collected after centrifugation at 16,000×g for 10 minutes and protein concentration was determined.

Enzyme Preparation from Tobacco Transplastomic Leaf Material

Fresh green leaves were collected and ground in liquid nitrogen. Total soluble protein was extracted in 50 mM sodium acetate buffer, pH 5.5 for cpCelD, cpXyn2 or 100 mM Tris-Cl buffer, pH 7.0 for PelD and PelB. All buffers contained protease inhibitor cocktail (Roche) and sodium azide (0.02%). Total soluble protein was filtered using 0.22 μm syringe filter, Protein concentration (mg/ml) in TSP was determined using Bradford method.

Enzyme Assays for Pectate Lyase B and Pectate Lyase D

Pectate lyases B and D were assayed spectrophotometrically by measuring the increase in $A_{235}$[30, 49, 50]. Kinetics of the pectate lyase B and D were studied to optimize substrate concentration (0.0-2.5 mg) under identical protein and cofactor concentration. The reaction mixtures contained 1 ml of 50 mM Tris-HCl buffer (pH 8.0) with 1 mM $CaCl_2$ (freshly prepared), 1 ml of 0.0-2.5 mg/ml sodium polygalacturonate (Sigma) and 0.5 ml of suitably diluted enzyme solution. Measurements were carried out at 40° C. One unit of enzyme was defined as the amount of enzyme which forms 1 μmol of product per min with a molar extinction coefficient of 4,600 $\mu mol^{-1}$ $cm^{-1}$. Kinetic studies were carried out in 50 mM Tris-HCl buffer, pH 8.0 at 40° C. Kinetic parameters (Km & Vmax) were calculated using non linear regression using Graphpad Prism 5.0. The initial slopes of each substrate concentration were calculated, where as the velocity (units/mg/min) was defined through the release of unsaturated galacturonic acid. The temperature optimization for pectate lyase B and D activity was carried out in 50 mM Tris-HCl buffer, pH 8.0 at different temperatures ranging from 30° C. to 70° C. In each case, the substrate was pre-incubated at the desired temperature for 5 min. In order to study the thermal stability of the enzyme, buffered enzyme samples were incubated for fixed time period at different temperatures.

The pH optimum of the pectate lyase B and D was measured at 40° C. using different buffers ranging from pH 6 to 10, with the same ionic strength. The stability of the crude extract of the enzyme was optimized by incubating the enzyme at the different pH. The influence of the cofactor CaCl$_2$ on pectate lyase activity was studied by conducting the reactions in its presence and absence at different pH and temperature.

Enzyme Assay for CelD and Commercial Cocktail (Celluclast 1.5 L and Novozyme 188)

Cellulase enzyme activity of cpCelD was determined by incubating crude extract in 2% carboxylmethylcellulose, avicel and sigmacell (Sigma) as substrate according to IUPAC recommendations[32] in 50 mM sodium acetate buffer pH 6.0 and incubated at 60° C. for 30 minutes for CMC and 2 hours for avicel and sigmacell. Enzyme units of commercial cocktails Celluclast 1.5 L and Novozyme 188 were determined using 2% CMC, under identical assay conditions. Reducing sugar amount was determined using 3,5-dinitrosalicylic acid[31]. D-glucose and D-galacturonic acid were used as standard to measure release of glucose equivalents and unsaturated galacturonic acid molecules. CMC (2%) was used in determining the pH and temperature activity profile of cpCelD. One unit of enzyme was defined as the amount of enzyme that released 1 µmole glucose equivalents per minute/ml. Cellulase unit calculation for avicel and sigmacell was based on glucose hexokinase method according to the manufacturer's protocol (Sigma).

Enzymatic Hydrolysis of Filter Paper, Processed Wood and Citrus Peel

Enzyme assays were carried out either with one enzyme component or as cocktail on filter paper, processed wood and orange peel and released reducing sugar was determined using DNS method. Orange peel prepared from Valencia orange (*Citrus sinensis* cv Valencia) fruit was air dried overnight and ground in liquid nitrogen. Ground Valencia orange peel and pretreated wood biomass were washed several times in distilled water until no reducing sugar was detected by DNS reagent as well as by glucose hexokinase method.

For enzymatic digestion, 50-200 mg of processed wood sample or ground orange peel was used. Crude extracts containing enzymes from *E. coli* and plants were used in the cocktail for hydrolysis. End product reducing sugar was determined using DNS reagent[31] and D-glucose as standard. Ampicillin and kanamycin 100 µg/ml was added to prevent any microbial growth during the long durations of enzyme hydrolysis. Commercial enzyme cocktails Celluclast 1.5 L and Novozyme 188 were tested for hydrolysis of citrus peel and processed wood in the same assay conditions used for enzyme cocktails from crude extracts. Enzyme units of Celluclast 1.5 L and Novozyme 188 used for hydrolysis assays were equivalent to cpCelD enzyme units (based on CMC hydrolysis) present in cocktails of crude extracts. In all experiments control assays contained substrate without enzyme or enzyme without substrate. All experiments and assays were carried out in triplicate.

The inventors have used coding sequences from bacterial or fungal genomes to create chloroplast vectors. A novel PCR based method was used to clone ORFs without introns from fungal genomic DNA. *E. coli* expression system was used to evaluate functionality of each enzyme independently or their efficacy in enzyme cocktails before creating transgenic lines; enzymes of fungal origin were active without any need for post-translational modifications (disulfide bonds or glycosylation). The phenotypes of homoplasmic transplastomic lines were normal and produced flowers & seeds. Based on three cuttings of tobacco in one year, 49, 64 and 10,751 million units of pectate lyase and endoglucanase activity can be obtained each year in an experimental cultivar. This yield could be increased 18-fold when these enzymes are produced in commercial cultivars. Based on USDA Economic Research Service, the cost of production of Burley tobacco in 2004 was $3,981 per acre. Because most enzymes for hydrolysis of plant biomass are active at higher temperatures, it is feasible to harvest leaves and sun dry them, as reported previously for chloroplast derived xylanase[25]. Based on enzyme activity observed in plant crude extracts in this study, there is no need for purification. Therefore, excluding processing cost, enzymes could be produced as low as 0.008 cents for PelB, 0.006 cents for PelD per enzyme unit (as defined in the commercial source Megazyme). This is 925-1,233 fold less expensive for pectate lyase B & D, when compared with current commercial cost (Megazyme produced from *C. japonicus*). While this cost or yield comparison may not be the same for all chloroplast-derived enzymes, this concept provides a promising new platform for inexpensive enzyme cocktails to produce fermentable sugars from lignocellulosic biomass.

To the best of our knowledge, this is the first study using enzyme cocktails expressed in plants for hydrolysis of lignocellulosic biomass to produce fermentable sugars and direct comparison of enzyme properties produced via fermentation or in planta, using identical genes and regulatory sequences. Majority of enzyme hydrolysis studies on natural substrates like pretreated wood, corn stover or wheat straw have used commercially available enzymes[3, 42] or purified recombinant enzymes spiked with purified commercial enzymes[40, 43]. Accurate comparison of crude extract enzyme cocktails with commercial cocktails is not possible because of their unknown enzyme compositions. Therefore, equivalent enzyme units based on CMC hydrolysis was used as a basis for general comparison. ACCELLERASE™ 1000 (Genencor) was not available for this study because of required institutional agreements. Novozyme 188 purified enzyme cocktail did not yield any detectable glucose equivalents from processed wood and 11% more glucose equivalents with citrus peel, whereas Celluclast 1.5 L yielded 10% and 137% more with both biomass substrates than the crude extract cocktail, with equivalent enzyme units based on CMC hydrolysis. It is not surprising that crude extract cocktails performed equal to or better than purified enzyme cocktails because the later are produced by submerged fermentation from selected fungal strains that secerete several enzymes, simultaneously. According to Novozymes, a careful design of a combination of single component enzymes is necessary for rational utilization of these enzyme cocktails[44].

Example 9: Expression of Plant Degrading Enzymes

The teachings set forth in Examples 1-8 may be adapted for preparing expression cassettes of the heterologous gene, constructing transformation vectors; transforming chloroplasts and chloroplast expression any of a numerous list of enzymes that the inventors have identified will be helpful in degrading plant biomass sources. Also, Applicants refer to U.S. Patent Pubs 20070124830 and 20060117412 for techniques of chloroplast transformation and expression of proteins.

A non-limiting list of exemplary enzymes includes the following in Table I:

TABLE I

GOI (Genes of Interest)

1. Endoglucanases
   a) celD (*Clostridium thermocellum*)
   b) egI (*Trichoderma reesei*)
   c) egl1 (*Trichoderma reesei*)
2. Exoglucanase
   a) celO (*Clostridium thermocellum*)
3. Lipase
   a) lipY (*Mycobacterium tuberculosis*)
4. Pectate lyases
   a) pelA (*Fusarium solani*)
   b) pelB (*Fusarium solani*)
   c) pelD (*Fusarium solani*)
5. Cutinase
   a) cut (*Fusarium solani*)
6. Swollenin similar to expansins
   a) swo1 (*Trichoderma reesei*)
7. Xylanase
   a) xyn2 (*Trichoderma reesei*)
8. Acetyl xylan esterase
   a) axe1 (*Trichoderma reesei*)
9. Beta glucosidase
   a) bgl1 (*Trichoderma reesei*)
10. Mannanase
    a) man1 (*Trichoderma reesei*)
11. Arabinofuranosidase
    a) abf1 (*Trichoderma reesei*)
12. Lignin peroxidase
    a) lipJ (*Mycobacterium tuberculosis*)

In addition to the above list, attached table II-VII set forth a list of different enzymes that may be used in conjunction with embodiments of the invention. The EC nos. are recognized designations found on the world wide web at chem.qmul.ac.uk and NV-IUBMB) defining each of the cross references to relevant polypeptide sequences and encoding polynucleotide sequences. Accession Nos. pertain to identifications sequences in either Genbank (one letter followed by five digits, e.g. M12345) or the RefSeq format (two letters followed by an underscore and six digits, e.g., NT_123456). Each of the sequences and related accession nos. are stored in the Corenucleotide division of the GenBank database system. An accession no. listed on table II-VII for a specific gene can be easily found by inputting the accession number in the search field of the Entrez system found at ncbi.nlm.nih.gov.on the world wide web In a specific embodiment, the sequences of the accession nos. specifically listed in tables II-VI include those in their original state or as revised/updated in the Genbank system as of Feb. 28, 2008. In other embodiments, it is contemplated that sequences may be revised/updated after Feb. 28, 2008 but otherwise recognized by the art as the more accurate sequence of the accession no. compared to the sequence stored prior to Feb. 28, 2008. In these other embodiments, sequences as revised but recognized as the true sequence and having at least a 95% sequence identity to the sequence as stored in database prior to Feb. 28, 2008 shall be considered as the sequence for the relevant accession no.

Applicants also incorporate by reference the ASCII text file entitled 10669-034 seqid filed with the present application. This text file contains sequence information of the accessions nos listed in Tables II-VII.

In addition, nucleotides and peptides having substantial identity to the nucleotide and amino acid sequences relating plant degrading enzymes (such as those provided in tables II-VII) used in conjunction with present invention can also be employed in preferred embodiments. Here "substantial identity" means that two sequences, when optimally aligned such as by the programs GAP or BESTFIT (peptides) using default gap weights, or as measured by computer algorithms BLASTX or BLASTP, share at least 50%, preferably 75%, and most preferably 95% sequence identity. Preferably, residue positions which are not identical differ by conservative amino acid substitutions. For example, the substitution of amino acids having similar chemical properties such as charge or polarity are not likely to effect the properties of a protein. Non-limiting examples include glutamine for asparagine or glutamic acid for aspartic acid.

The term "variant" as used herein refers to nucleotide and polypeptide sequences wherein the nucleotide or amino acid sequence exhibits substantial identity with the nucleotide or amino acid sequence of Attachment B, preferably 75% sequence identity and most preferably 90-95% sequence identity to the sequences of the present invention: provided said variant has a biological activity as defined herein. The variant may be arrived at by modification of the native nucleotide or amino acid sequence by such modifications as insertion, substitution or deletion of one or more nucleotides or amino acids or it may be a naturally occurring variant. The term "variant" also includes homologous sequences which hybridise to the sequences of the invention under standard or preferably stringent hybridisation conditions familiar to those skilled in the art. Examples of the in situ hybridisation procedure typically used are described in (Tisdall et al., 1999); (Juengel et al., 2000). Where such a variant is desired, the nucleotide sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed, using techniques standard in the art.

In specific embodiments, a variant of a polypeptide is one having at least about 80% amino acid sequence identity with the amino acid sequence of a native sequence full length sequence of the plant degrading enzymes provided on the attached 10669-034SEDID ASCII file. Such variant polypeptides include, for instance, polypeptides wherein one or more amino acid residues are added, or deleted, at the N- and/or C-terminus, as well as within one or more internal domains, of the full-length amino acid sequence. Fragments of the peptides are also contemplated. Ordinarily, a variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with a polypeptide encoded by a nucleic acid molecule shown in Attachment B or a specified fragment thereof. Ordinarily, variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, or more.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by those that: (1) employ low ionic strength and high temperature for washing, 0.015 M sodium chloride/0.0015 M sodium citrate/0.1% sodium dodecyl sulfate at 50° C.; (2) employ during hybridization a denaturing agent, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 degrees C.; or (3) employ 50% formamide, 5×SSC (0.75 M NaCl, 0.075 M sodium citrate), 50 mM sodium phosphate (pH 6.8), 0.1% sodium pyrophosphate, 5.times. Denhardt's solution, sonicated salmon sperm DNA (50 μg/ml), 0.1% SDS, and 10% dextran sulfate at 42 degrees C., with washes at 42 degrees C. in 0.2×SSC (sodium chloride/sodium citrate) and 50% formamide at 55 degrees C., followed by a high-stringency wash consisting of 0.1×SSC containing EDTA at 55 degrees C.

"Moderately stringent conditions" are identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50 degrees C. The skilled artisan will recognize how to adjust the temperature, ionic strength, etc. as necessary to accommodate factors such as probe length and the like.

Typically, for stringent hybridization conditions a combination of temperature and salt concentration should be chosen that is approximately 12-20° C. below the calculated $T_m$ of the hybrid under study. The $T_m$ of a hybrid between an polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.50° C. - 16.6(\log_{10}[Na^+]) + 0.41(\% G+C) - 0.63(\% \text{ formamide}) - 600/l),$$

where l=the length of the hybrid in basepairs.
In a specific embodiment, stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Example 10: Optimization of Recombinant Expressed Enzyme Cocktails

Having demonstrated by several examples that plant-degrading enzymes can be expressed in plants and bacteria, cocktails of enzymes can be produced that are especially adapted for degrading a targeted class of biomass. The inventors have discovered that certain combinations of selected enzymes are capable of hydrolyzing biomass materials in a synergistic fashion. For example, it has been discovered that two or more enzymes from a particular class work synergistically to degrade targeted material in biomass to increase the yield of fermentable sugars achieved. Based on the known composition of a target biomass sample, more than one enzyme in a particular class is included in the plant degrading cocktail. Furthermore, the amount of enzyme of a specific enzyme class known to degrade a specific compound in a biomass sample is increased relative to other enzyme in the cocktail as a function of the ratio of the specific compound/mass of biomass sample. General information concerning exemplary classes of enzymes are discussed below in relationship to the type of substrates on which they act. Equipped with the teachings and techniques discussed herein, one skilled in the art is able to determine cocktails suitable for a given biomass, and methods by which synergy of the enzymes in the cocktails can be determined.

Enzyme Assays

Most enzyme assays were determined spectrophotometrically by measuring the increase in $A_{235}$[30, 47, 48]. Enzyme kinetics were studied to optimize substrate concentration (0-2.5 mg) under identical protein and cofactor concentrations. The reaction mixtures contained appropriate buffers, substrates and standard enzymes when commercially available. Measurements are made at different temperatures and pH. One unit of enzyme is defined as the amount of enzyme which forms 1 μmol of product per min with appropriate molar extinction coefficient. Kinetic parameters (Km & Vmax) are calculated using non linear regression using Graphpad Prism 5.0. The initial slopes of each substrate concentration are calculated where as the velocity (units/mg/min) is defined through the release of appropriate product. The temperature optimization is determined in proper buffers with required co-factors, substrates at optimal pH. In order to study the thermal stability of each enzyme, buffered enzyme samples are incubated for fixed time periods at different temperatures. Similarly, the pH optimum of each enzyme are measured at optimal temperatures using different buffers ranging from pH 6 to 10, with the same ionic strength. The stability of the crude extract of the enzyme is optimized by incubating the enzyme at the different pH. The influence of various cofactors for optimal enzyme activity is studied by conducting the reactions in the presence or absence of each cofactor, at different pH and temperature.

Endoglucanase, Cellobiohydralase and Beta-Glucosidase:

Cellulose is the most abundant renewable bioresource produced in the biosphere through photosynthetic process (~100 billion dry tons/year)[49-51]. Cellulose biodegradation by cellulases and cellulosomes, produced by numerous microorganisms, represents a major carbon flow from fixed carbon sinks to atmospheric CO2 and studies have shown that the use of biobased products and bioenergy can achieve zero net carbon dioxide emission[52, 53]% Cellulose is a linear condensation polymer consisting of D-anhydroglucopyranose joined together by β-1,4-glycosidic bonds with a degree of polymerization (DP) from 100 to 20,000. Approximately 30 individual cellulose molecules are assembled into larger units known as elementary fibrils (protofibrils), which are packed into larger units called microfibrils, and these are in turn assembled into large cellulose fibers[54, 55]. The breakdown of biomass involves the release of long-chain polysaccharides, specifically cellulose and hemicellulose, and the subsequent hydrolysis of these polysaccharides into their component 5- and 6-carbon chain sugars[15]. One of the most important and difficult technological challenges is to overcome the recalcitrance of natural lignocellulosic materials, which must be enzymatically hydrolyzed to produce fermentable sugars[2, 7, 8, 56, 57].

The mechanism of cellulose degradation involves three enzyme classes of cellulase. These include endoglucanases or 1,4-β-D-glucan-4-glucanohydrolases (EC 3.2.1.4) exoglucanase or 1,4-β-D-glucan cellobiohydrolases (E.C. 3.2.1.91), and β-glucosidase or β-glucoside glucohydrolases (E.C. 3.2.1.21)[55, 58, 59]. The combined actions of endoglucanases and exoglucanases modify the crystalline nature of cellulose surface over time, resulting in rapid changes in hydrolysis rates.[60] The inventor has realized that the simultaneous action of these enzyme class on cellulose substrate completely breaks down the intramolecular β-1,4-glucosidic bonds of cellulose chains. This results in release of large amount of fermentable glucose molecules.

Endoglucanases (e.g CelD, Eg1): Endoglucanases cut at random at internal amorphous sites in the cellulose polysaccharide chain, generating oligosaccharides of various lengths and consequently expose new chain ends. Exoglucanases (e.g. CelO, Cbh2): Exoglucanases or cellobiohydrolases acts processively on the reducing or nonreducing ends of cellulose polysaccharide chains, liberating either glucose (glucanohydrolases) or cellobiose (cellobiohydrolase) as major products. Cellobiohydralases can also act on amorphous and microcrystalline cellulose structure having exposed cellulose chain ends. β-Glucosidases (e.g., BglA, Bgl1): It hydrolyze soluble cellobiose as well as longer cellodextrins molecules to glucose.

CelD, Egl1, EG1 (endo-glucanases) and CelO (cellobiohydrolase): Substrate: Carboxylmethylcellulose (2%) beta D-glucan (10 mg/ml), microcrystalline cellulose, Avicel, Sigma cellulose (all 50 mg/ml). At least two dilutions are made for each enzyme sample investigated in 50 mM sodium acetate buffer containing 10 mM $CaCl_2$ and 20 µg BSA. In the assay, one dilution should release slightly more and one slightly less than 0.5 mg (absolute amount) of glucose. The sample is incubated at appropriate temperature for 30 minutes after adding 0.5 ml of substrate solution. After incubation, 0.5 ml of DNS is added to 0.5 ml of the reaction mixture followed by boiling for exactly 5 minutes in a boiling water bath along with enzyme blanks and glucose standards. Following boiling, 166 µl of 40% Rochelle salt is added and transferred immediately to a cold water bath not more than 30 minutes. The tube is mixed by inverting several times so that the solution separates from the bottom of the tube at each inversion. The mixture is measured at 575 nm in a spectrometer. The absorbance is translated (corrected if necessary by subtracting of the blank) into glucose production during the reaction using a glucose standard curve graph. Enzyme unit is defined as the amount of enzyme required to liberate 1.0 µmol per minute.[32]

Bgl1 (*Trichoderma reesei*): Beta-Glucosidase Assays: Substrate: Cellobiose, 2-15 Mm in Sodium Acetate Buffer pH 4.8

At least two dilutions are made of each enzyme sample investigated. One dilution should release slightly more and one slightly less than 1.0 mg (absolute amount) of glucose in the reaction conditions. Add 1.0 ml of enzyme dilution in sodium acetate buffer pH 4.8 to 1.0 ml of cellobiose substrate. Incubate at 50° C. for 30-120 minutes. Stop assay by boiling in water bath for 5 minutes. Determine liberated glucose using glucose hexokinase (Sigma) method. One unit of enzyme is defined as 1.0 µmol of glucose released per minute from cellobiose. Substrate: 2-15 mM para-nitrophenyl D-glucoside in sodium acetate buffer pH 4.8. Add 0.3 ml of diluted enzyme solution to 0.6 ml 50 mM sodium acetate buffer and 0.3 ml para-nitrophenyl D-glucoside. Carry out the reaction at 50° C. for 10 minutes. Stop the reaction with 1M Na2CO3. Spectrophometrically measure the liberated p-nitrophenol at 410 nm using p-nitrophenol as standard. Construct the calibration curve for p-nitrophenol in the concentration range of 0.02-0.1 mM. Enzyme unit is defined as the amount of enzyme required to liberate 1.0 µmol of p-nitrophenol per min from pNPG.

Xylanase

Endo-xylanses: Xylan is one of the major components of the hemicellulose fraction of plant cell walls and accounts for 20-30% of their total dry mass. Unlike cellulose, xylan is a complex polymer consisting of a β-1,4-linked xylose monomers substituted with side chains. Hydrolysis of the xylan backbone is catalyzed by endob-1,4-xylanases (EC 3.2.1.8) and β-D-xylosidases (EC 3.2.1.37).[61] Endoxylanases are capable of hydrolyzing the internal 1,4-β-bonds of the xylan backbone and thereby produce several xylooligomers of varying length. Complete hydrolysis of xylan involves endo-β-1,4-xylanase, β-xylosidase, and several accessory enzymes, such as a-L-arabinofuranosidase, α-glucuronidase, acetylxylan esterase and ferulic acid esterase.[62, 63] For the biofuel industry, the inventor has realized that xylanases can be used to aid in the conversion of lignocellulose to fermentable sugars (e.g., xylose). Furthermore, hydrolysis of xylan molecules is very important step in the enzymatic hydrolysis hemicellulose and lignocellulosic materials because this gives larger accessibility for cellulases to act on exposed cellulose.

Xylanase Assay[64] (Baily 1989):

Xyn2 (*Trichoderma reesei*)

Substrate: Oat spelt xylan (1%); Birch wood xylan (1%, boil for 5 minutes until dissolved) D-xylose (0.01 to 1 mg/ml xylose) standard graph will be prepared by using DNS method. Assay: The enzyme sample is diluted in 1% xylan suspension with a total volume reaction up to 2 ml. Then the mixture is incubated for 30-120 minutes at 50° C. After incubation, 2 ml of DNS reagent is added to the reaction mixture followed by boiling for 5 minutes. The release of xylose concentration is measured spectrophotometrically at 540 nm. The enzyme unit is calculated by using standard formula[64].

Cutinase:

Cutinase from the phytopathogenic fungus *Fusarium solani* pisi is an example of a small carboxylic ester hydrolase that bridges functional properties between lipases and esterases. Cutin, a polyester composed of hydroxy and hydroxy epoxy fatty acids containing 16 and 18 carbon atoms, is the major structural component of the protective barrier covering the surface of the aerial parts of plants[65, 66]. Cutinases not only degrade cutin polymers but also a large variety of short and long chain triacylglycerols are rapidly hydrolyzed. The enzyme belongs to the family of serine hydrolases containing the so called α/β hydrolase fold.[67, 68] Hydrolyses of cutin, lipase and triacylglycerols molecules that present in large amount in citrus peel waste gives tremendous accessibility for enzymes like pectinases, cellulases and xylanases. Therefore cutinase is important enzyme component in the enzyme hydrolyses of citrus peel for biofuel production.

Cutinase assay[67, 69]: Substrate: p-nitrophenyl butyrate and p-nitrophenyl palmitate (0.01% or 10 mM). The enzyme is extracted from transplastomic plants in 100 mM Tris-HCl buffer (pH7.0) and 0.03% Triton X-100 will be added at the time of initiating enzyme assay. Reactions are performed by incubating for 10-15 min at 30° C. in a tube containing 1 ml of substrate (100 mM Tris-HCl, pH 7, 0.03% Triton X-100, and 0.01% p-nitrophenol butyrate and various amount of enzyme sample (ice cold). Release of p-nitrophenol is measured at 405 nm using p-nitrophenol as standard. Background activity is subtracted from the absorption reading if necessary. One unit of enzyme activity was defined as the amount that degrades 1 μmol of substrate per minute under standard conditions.

Mannanase:

Mannanase is used in the paper and pulp industry, for the enzymatic bleaching of softwood pulp, in the detergent industry as a stain removal booster, in the coffee industry for hydrolysis of coffee mannan to reduce the viscosity of coffee extracts, in oil drilling industry to enhance the flow of oil or gas, in oil extraction from coconut meat, in the textile industry for processing cellulosic fibers and in the poultry industry to improve the nutritional value of poultry feeds.[70]

Cell-wall polysaccharides can be converted into fermentable sugars through enzymatic hydrolysis using enzymes such as cellulases and hemicellulases and the fermentable sugars thus obtained can be used to produce lignocellulosic ethanol. Mannanase is a hemicellulase. Hemicellulose is a complex group of heterogeneous polymers and represents one of the major sources of renewable organic matter. Mannans are one of the major constituent groups of hemicellulose and are widely distributed in hardwoods and softwoods, seeds of leguminous plants and in beans. Hemicelluloses make up 25-30% of total wood dry weight. Hemicelluloses in softwoods are mainly galactoglucomannan, containing mannose/glucose/galactose residues in a ratio of 3:1:1 and glucomannan with mannose/glucose residues in the ratio of 3:1[71]. Mannanases are endohydrolases that cleave randomly within the 1,4-β-D mannan main chain of galactomannan, glucomannan, galactoglucomannan, and mannan. Mannanases hydrolyzes the β-D-1,4 mannopyranoside linkages in β-1, 4 mannans. The main products obtained during the hydrolysis of mannans by β-mannanases are mannobiose and mannotriose. Additional enzymes, such as β-glucosidases and α-galactosidases are required to remove side chain sugars that are attached at various points on mannans. A vast variety of bacteria, actinomycetes, yeasts and fungi are known to produce mannanase. Among bacteria, mostly gram-positive, including various *Bacillus* species and *Clostridia* species and few strains of gram negative bacteria, viz. *Vibrio* and *Bacteroides* have also been reported. The most prominent mannan degrading group among fungi belongs to genera *Aspergillus, Agaricus, Trichoderma* and *Sclerotium*.[70]

The assay procedure for determination of the activity of Mannanase involves the incubation of the crude enzyme extract with the substrate (Galactomannan from Locust bean gum as a substrate). After the enzyme reaction the reducing sugars liberated are quantified and the enzyme activity is measured. Locust bean gum (0.5%) will be dissolved in citrate buffer (pH 5.3) and heated until boiled; this mixture is used as the substrate. The crude enzyme extract is incubated with the substrate at 50° C. for 5 minutes. The reducing sugars liberated in the enzyme reaction is assayed by adding Dinitro salicylic acid-reagent boiling for 5 min, cooling and measuring the absorbance at 540 nm[72].

Another assay method involves carob galactomannan (0.2%) as substrate in sodium acetate buffer (pH 5). Crude enzyme extract is incubated with the substrate at 40° C. for 10 minutes. The reducing sugars liberated are measured by Nelson-Somogyi method and the enzyme activity is quantified[73]. In gel diffusion assay, gel plates are prepared by dissolving 0.05% (w/v) locust bean gum in citrate phosphate buffer (pH 5.0) along with Phytagar. Crude enzyme extract is transferred to the gel plates and incubated for 24 hours. Gels will be stained by using Congo red. Cleared zones (halos) on the plates indicated endo-beta-mannanase activity[74].

Arabinofuranosidase 1 (ABF1)

ABF1 has been shown to have numerous potential uses. L-arabinose is found throughout many different plant tissues in small amounts but strategically placed as side groups. ABF1 facilitates the breakdown of these side chains and cross-linking within the cell wall to work synergistically with other enzymes such as hemicellulases. This can increase the availability of fermentable sugars for biofuel production from biomass or pulp and paper production. This enzyme can increase the digestibility of livestock feed, has been used in the clarification of fruit juices and can aid in the aromatization of wines. Finally, ABF1 has possibilities as a food additive for diabetics due to the sweet taste and inhibitory effect on the digestion of sucrose[75].

ABF1 was isolated from the fungus *T. reesei* and expressed in *Escherichia coli* in the pLD plasmid. The activity of this enzyme is assayed through the use of p-nitrophenyl-α-L-arabinofuranoside substrate in a 0.05M citrate buffer incubated at 50° C. for 10 minutes with enzyme crude extracts from plants or *E. coli*. The reaction is stopped with 1M $Na_2CO_3$ and the resultant p-nitrophenol is measured by spectrophotometer at 400 nm and compared to the positive standard (either p-nitrophenol or ABF, both of which are available commercially) to determine quantity. The pH and temperature optima studies are performed with the same substrate and measured in the same fashion 76. The activity of this enzyme has been known to be inhibited certain metal ions such as $Cu^{2+}$, $Hg^{2+}$, detergents and many chelating and reducing agents.[75]

Lignin Peroxidase (LipJ)

The enzyme Lignin peroxidase, commonly known as LipJ, remains novel and desirable for advancing the production of biofuel enzymes by means of transplastomic tobacco. Expression of LipJ should expand the spectra of exploitable biomass sources by hydrolysis of the inedible lignin and cellulose rich portions of biomass such as corn, sugarcane and wheat. Sources previously occluded as sources for biofuel due their high lignin content e.g. waste lumber, wood chips, peels from commercially prepared fruit and vegetables, could be hydrolyzed with LipJ. LipJ also advances biofuels production by ablating the intricate lignin structures within plant materials from inhibiting access to more valuable biomass substrates that provide valuable commercial, chemical and pharmaceutical products. These products are as of yet, limited in yield because of the protective nature of lignin surrounding them within biomass sources.

LipJ, was isolated from genomic DNA of *Mycobacterium tuberculosis*, expressed in a plasmid functional in both chloroplasts and *E. coli*. Three cultivars of transplastomic tobacco are expressing this vector in the primary selection round and await confirmation of chloroplast expression. Protein assays in *E. coli* have been designed for qualitative & quantitative analysis of LipJ expression, which is optimized for chloroplast derived LipJ.

Lipase (Lip Y)

Lipase Y (LipY), from *Mycobacterium Tuberculosis*, is a water soluble enzyme that catalyzes the hydrolysis of ester bonds and long-chain triacylglycerols, making it an ideal candidate for biofuel production. LipY is a membrane protein for *Mycobacterium Tuberculosis* and studies have already shown a humoral response will occur when LipY is combined with the serum of tuberculosis patients; therefore, LipY has the added benefit of being a potential vaccine for tuberculosis 77.

One simple assay for determining the activity of the cloned gene is a plate assay involving the fluorescent dye rhodamine B and a crude extract of lyses cells. If the gene was properly integrated and the protein folded correctly the assay will display an orange color when illuminated under a specific wavelength of light 80. Another assay measures the release of p-nitrophenol when p-nitrophenylstearate is incubated in various concentrations of *E. coli* or plant cell extract[81].

Example 11: Expression of Plant Degrading Enzymes in Commercial Cultivars

Tobacco chloroplasts were transformed by microprojectile bombardment (biolistic transformation) as described before. Transgene integration was confirmed by PCR analysis using primers used in previous studies. Southern blot analysis was conducted to confirm homoplasmy. Tobacco (*Nicotiana tabacum* var. Petit Havana/LAMD/TN90) seeds were aseptically germinated on MSO medium in Petri dishes. Germinated seedlings were transferred to magenta boxes containing MSO medium. Leaves at 3-7 leaf stage of plant growth were cut and placed abaxial side up on a Whatman filter paper laying on RMOP medium in Petri plates (100×15 mm) for bombardment. Gold microprojectiles (0.6 μm) were coated with plasmid DNA (tobacco chloroplast expression vector) and biolistic mediated transformation were carried out with the biolistic device PDS1000/He (Bio-Rad) as published. After bombardment, leaves were incubated in dark for 48 hours to recover from damage. After 48 hours in dark, the bombarded leaves of Petit Havana (experimental cultivar) or LAMD and TN90 (commercial cultivar) were cut into 5 mm pieces and placed on plates (bombarded side in contact with medium) containing RMOP with 500, 150 and 200 mg/l of spectinomycin respectively for the first round of selection. After 4-5 weeks, resistant shoots will appear, whereas untransformed cells will die. Resistant shoots will be transferred to new RMOP-Spectinomycin plates and subjected to subsequent rounds of selection. The putative transplastomic shoots were confirmed by PCR and Southern analysis. Expression of cell wall degrading enzymes were confirmed by their respective assays and for those that antibody was available, Western blot analysis was performed.

The commercial cultivars yielded 40 metric tons biomass of fresh leaves as opposed to 2.2 tons in experimental cultivar Petit Havana. The commercial cultivars yield biomass 18 fold more than the experimental cultivar (Cramer et al., 1999). LAMD-609 is a low nicotine hybrid produced by backcrossing a Maryland type variety, MD-609, to a low nicotine-producing burley variety, LA Burley 21 (Collins et al., 1974), Tennessee 90 (TN 90) is a commercial cultivar used by Philip Morris (Lancaster Laboratories, PA). Both experimental cultivars LAMD and TN 90 were transformed with genes encoding biomass degrading enzymes. Although it is more challenging to transform these cultivars than the experimental cultivar, we succeeded in transforming both commercial cultivars with a number of genes encoding biomass degrading enzymes pectate lyases, cellulases, xylanases and endoglucanases. Transplastomic lines of commercial cultivars were homoplasmic, fertile and activities of expressed enzymes were similar to the experimental cultivar except that their biomass yield was much higher than Petit Havana. Table 8 shows enzymes that have been successfully introduced in plants, expressed and assayed for activity in experimental and commercial cultivars.

PCR was done using DNA isolated from leaf material of control and putative transgenic plants in order to distinguish true chloroplast transformants from nuclear transformants or mutants. Two separate PCR reactions was set up, one reaction checked for the integration of selectable marker gene into the chloroplast genome and the second checked integration of the transgene expression cassette. In order to test chloroplast integration of the transgenes, one primer (3M) will land on the aadA gene while another (3P) will land on the native chloroplast genome. No PCR product was obtained with nuclear transgenic plants or mutants using this set of primers. This screening is important for eliminating mutants and nuclear transformants. In order to conduct PCR analysis in transgenic plants, total DNA from unbombarded and transgenic plants was isolated as described by DNeasy plant mini kit (Qiagen). Integration of transgene expression cassette was tested using 5P/2M primer pair. Primer 5P lands in the aadA gene and 2M in the trnA, therefore, the PCR product showed whether the gene of interest had been introduced into the chloroplast genome via the homologous recombination process. A similar strategy has been used successfully by PI lab to confirm chloroplast integration of several foreign genes. The leaf pieces from PCR-positive shoots was further selected for a second round in order to achieve homoplasmy.

Southern blots were done to test homoplasmy. There are several thousand copies of the chloroplast genome present in each plant cell. When foreign genes are inserted into the chloroplast genome, not all chloroplasts will integrate foreign DNA resulting in heteroplasmy. To ensure that only the transformed genome exists in transgenic plants (homoplasmy), the selection process was continued. In order to confirm homoplasmy at the end of the selection cycle, total DNA from transgenic plants was probed with the radiolabeled chloroplast flanking sequences (the trnI-trnA fragment) used for homologous recombination. If wild type genomes are present (heteroplasmy), the native fragment size was observed along with transformed genomes. Presence of a large fragment due to the insertion of foreign genes within the flanking sequences and the absence of the native small fragment should confirm homoplasmy.

Figure 6:
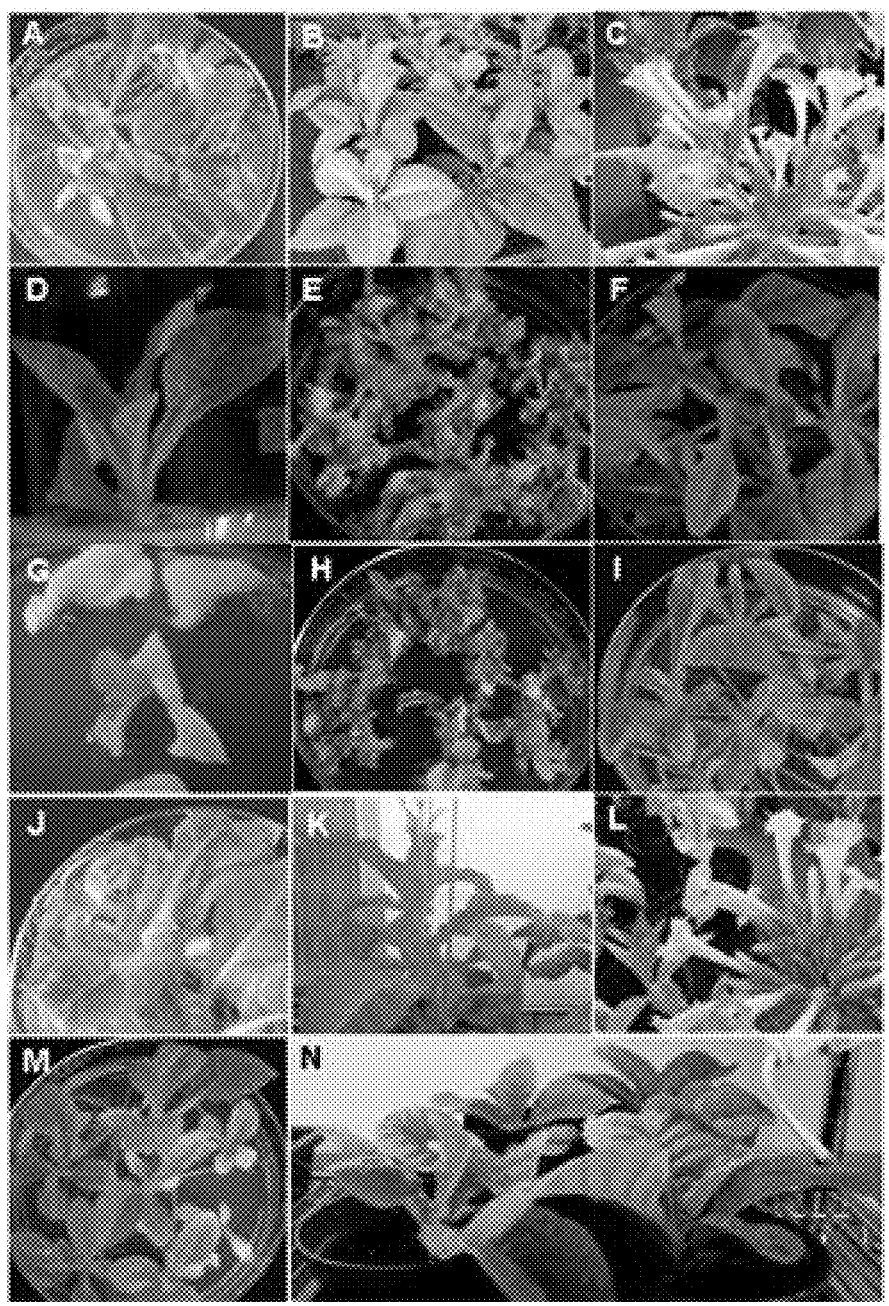
FIG. 6 Generation of transplastomic tobacco commercial cultivars (A) Rooting of CelD LAMD shoot (B) CelD LAMD transplastomic plants growing in the green house (C) CelD LAMD transplastomic plants showing normal flowering (D) CelD TN90 primary transformant (E) Second round of regeneration for CelD TN90 (F) Rooting of PelB TN90 (G-I) First, second and third round of regeneration for PelB LAMD (J) Rooting of PelD LAMD shoot (K) PelD LAMD transplastomic plants growing in green house (L) PelD LAMD transplastomic plant showing normal flowering (M) Rooting of eg1 LAMD shoot (N) eg1 LAMD transplastomic plant growing in pots.

FIG. 6 shows the generation of transplastomic tobacco commercial cultivars (A) Rooting of CelD LAMD shoot (B) CelD LAMD transplastomic plants growing in the green house (C) CelD LAMD transplastomic plants showing normal flowering (D) CelD TN90 primary transformant (E) Second round of regeneration for CelD TN90 (F) Rooting of PelB TN90 (G-I) First, second and third round of regeneration for PelB LAMD (J) Rooting of PelD LAMD shoot (K) PelD LAMD transplastomic plants growing in green house (L) PelD LAMD transplastomic plant showing normal flowering (M) Rooting of eg1LAMD shoot (N) eg1 LAMD transplastomic plant growing in pots.

Figure 7:
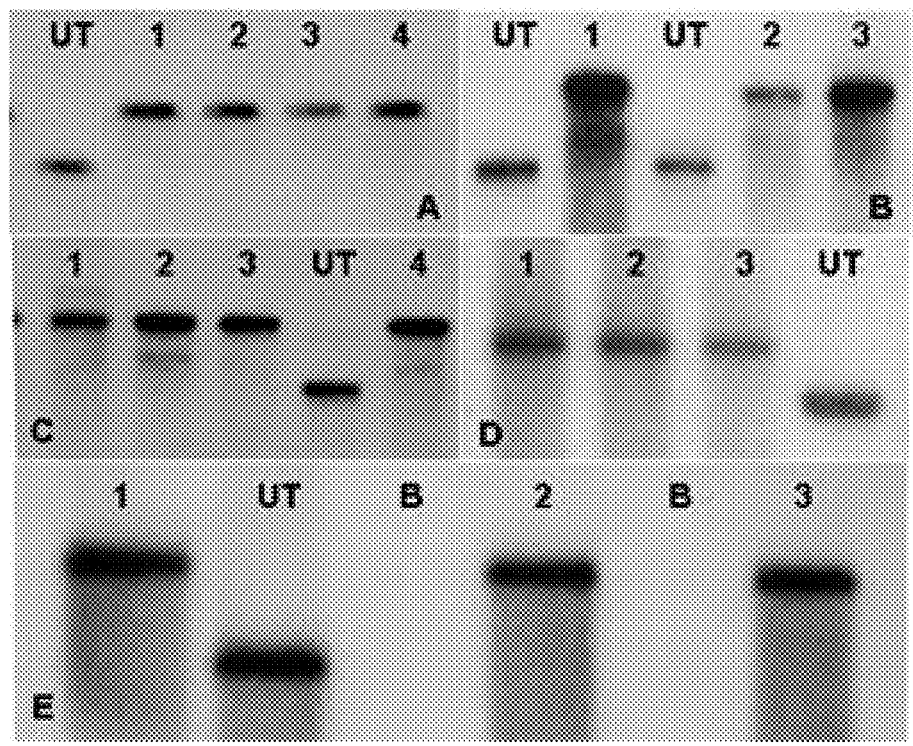
FIG. 7 Confirmation of homoplasmy by southern blots using tobacco flanking probe (A) CelD LAMD (B) PelB LAMD (C) PelB TN90 (D) PelD LAMD and (E) eg1 LAMD (UT: Untransformed plant; Numbers: Transplastomic lines and B: Blank).
Figure 8:
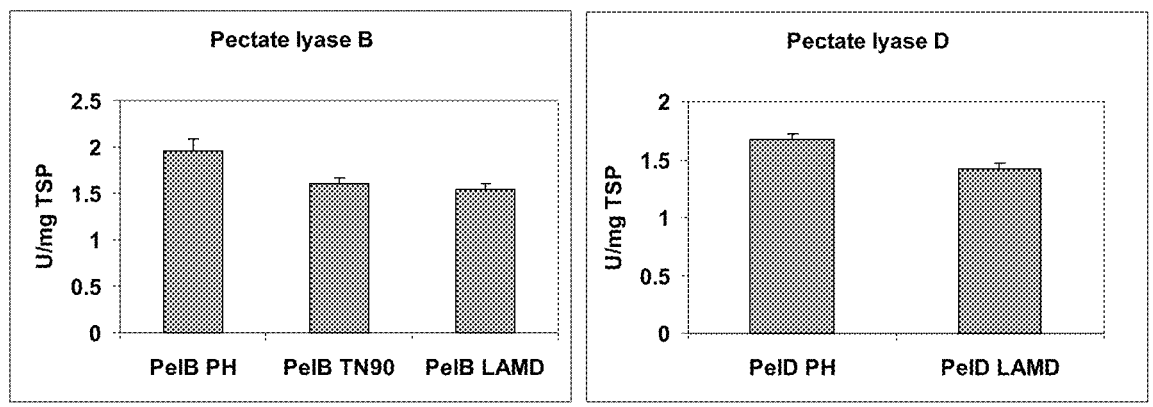
FIG. 8 Enzymatic activity of pectate lyase B and D in Petit Havana, TN90 and LAMD tobacco cultivars (A) PelB (B) PelD Note: The leaf material used for the analysis of enzyme activity for TN90 and LAMD tobacco cultivars were harvested from in vitro plants, whereas the leaf material for Petit Havana is from the green house. Since the transgene is controlled by psbA, with light and developmental regulatory elements, expression levels in commercial cultivars are expected to be higher when transferred to the green house.

FIG. 7 shows confirmation of homoplasmy by southern blots using tobacco flanking probe (A) CelD LAMD (B) PelB LAMD (C) PelB TN90 (D) PelD LAMD and (E) eg1 LAMD (UT: Untransformed plant; Numbers: Transplastomic lines and B: Blank). FIG. 8 shows enzymatic activity of pectate lyase B and D in Petit Havana, TN90 and LAMD tobacco cultivars (A) PelB (B) PelD Note: The leaf material used for the analysis of enzyme activity for TN90 and LAMD tobacco cultivars were harvested from in vitro plants, whereas the leaf material for Petit Havana is from the green house. Since the transgene is controlled by psbA, with light and developmental regulatory elements, expression levels in commercial cultivars are expected to be higher when transferred to the green house.

TABLE 8

Summary of Successful Transformation, Expression and Active Recombinantly Expressed Enzymes

| Gene Name | PCR Positive | Southern Status | At what stage | No. of plants | Frozen material (gms) | Assay with E. coli extract protocols | Assay with plant extract | Plant Health |
|---|---|---|---|---|---|---|---|---|
| celD | Yes, Petit Havana (PH) | Homoplasmy | Collected seeds | T0 seeds germinated | 400 | Yes | Yes | Normal |
|  | Yes (LAMD) | Homoplasmy | Collected seeds | T0 seeds germinated | 250 |  | Yes | Normal |
|  | Yes (TN90) | Not Checked | 2$^{nd}$ Round of selection | 4 clones |  |  | Yes | Normal |
| pelB | Yes (PH) | Homoplasmy | Collected seeds | T0 seeds germinated | 700 | Yes | Yes | Normal |
|  | Yes (LAMD) | Homoplasmy | Rooting | 18 plants |  |  | Yes | Normal |
|  | Yes (TN90) | Homoplasmy | Ready for Green house production | 30 plants |  |  | Yes | Normal |
| pelD | Yes (PH) | Homoplasmy | Collected seeds | T0 seeds germinated | 600 | Yes | Yes | Normal |
|  | Yes (LAMD) | Homoplasmy | Collected seeds | T0 seeds germinated | 340 |  | Yes | Normal |
| pelA | Yes (PH) | Homoplasmy | Ready for Green house production | 9 |  | Yes | Yes | Normal |
| egI | Yes (PH) | Homoplasmy | Ready for Green house production | 9 |  | Yes | Yes | Normal |
|  | Yes (LAMD) | Homoplasmy | Ready for Green house production | 3 |  |  | Yes | Normal |
| Egl1 | Yes (PH) | in progress | Rooting | 20 |  | in progress | in progress | Normal |
|  | Yes (TN90) | in progress | 2$^{nd}$ round of selection | 3 clones |  |  |  | Normal |
| Xyn2 | Yes (PH) | Homoplasmy | Ready for Green house production | 7 |  | Yes | Yes | Normal |
| Swo1 | Yes (PH) | Homoplasmy | Rooting | 20 |  | Yes | Yes | Thin leaves |
| Bgl1 | Yes (PH) | Homoplasmy | Ready for Green house production | 20 |  | Yes | in progress | Normal |
| Cutinase | Yes (PH) | in progress | Rooting | 15 |  | Yes | in progress | Leaves are thin |
| cello | Yes (PH) | Heteroplasmy | Rooting | 20 |  | Yes | in progress | Normal |
|  | Screening (LAMD) | in progress | 2$^{nd}$ round of selection | 5 clones |  | Yes | in progress | Normal |

TABLE 8-continued

Summary of Successful Transformation, Expression and Active Recombinantly Expressed Enzymes

| Gene Name | PCR Positive | Southern Status | At what stage | No. of plants | Frozen material (gms) | Assay with E. coli extract protocols | Assay with plant extract | Plant Health |
|---|---|---|---|---|---|---|---|---|
| Axe1 | Bombarded in all cultivars | — | In RMOP selection medium | | | Yes | | |
| lip Y | Bombarded in all cultivars | — | In RMOP selection medium | | | Yes | | |
| lipJ | Bombarded in all cultivars | — | In RMOP selection medium | | | yes | | |
| Man1 | Bombarded in all cultivars | — | In RMOP selection medium | | | Yes | | |
| Abf1 | Bombarded in all cultivars | — | In RMOP selection medium | | | | | |

The disclosures of the cited patent documents, publications and references, including those referenced in Tables II-VII, are incorporated herein in their entirety to the extent not inconsistent with the teachings herein. It should be understood that the examples and embodiments described herein are for illustrative purposes only and that various modifications or changes in light thereof will be suggested to persons skilled in the art and are to be included within the spirit and purview of this application.

REFERENCE LIST FOR EXAMPLES 1-8

1. Robertson, G. P. et al. AGRICULTURE: Sustainable Biofuels Redux. *Science* 322, 49-50 (2008).
2. Sticklen, M. B. Plant genetic engineering for biofuel production: towards affordable cellulosic ethanol. *Nat Rev Genet.* 9, 433-443 (2008).
3. Merino, S. T. & Cherry, J. Progress and Challenges in Enzyme Development for Biomass Utilization in *Advances in Biochemical Engineering/Biotechnology* 95-120 (Springer Berlin/Heidelberg, 2007).
4. Wyman, C. E. et al. Coordinated development of leading biomass pretreatment technologies. *Bioresour Technol* 96, 1959-1966 (2005).
5. Grohmann, K., Baldwin E. A., Buslig, B. S., & Ingram L. O Fermentation of galacturonic acid and other sugars in orange peel hydrolysates by the ethanologenic strain of *Escherichia coli*. *Biotechnology Letters* 16, 281-286 (1994).
6. Himmel, M. E. et al Advanced bioethanol production technologies: a prospective. In ACS Symposium 666, 2-45. 1997. American Chemical Society Washington, D.C. Ref Type: Conference Proceeding
7. Himmel, M. E., Ruth, M. F., & Wyman, C. E. Cellulase for commodity products from cellulosic biomass. *Current Opinion in Biotechnology* 10, 358-364 (1999).
8. Taylor II, L. E. et al. Heterologous expression of glycosyl hydrolases in planta: a new departure for biofuels. *Trends in Biotechnology* 26, 413-424 (2008).
9. Ziegelhoffer, T., Will, J., & ustin-Phillips, S. Expression of bacterial cellulase genes in transgenic alfalfa (*Medicago sativa* L.), potato (*Solanum tuberosum* L.) and tobacco (*Nicotiana tabacum* L.). *Molecular Breeding* 5, 309-318 (1999).
10. Kawazu, T. et al. Expression of a bacterial endoglucanase gene in tobacco increases digestibility of its cell wall fibers. *Journal of Bioscience and Bioengineering* 88, 421-425 (1999).
11. Dai, Z., Hooker, B. S., Anderson, D. B., & Thomas, S. R. Improved plant-based production of E1 endoglucanase using potato: expression optimization and tissue targeting. *Molecular Breeding* 6, 277-285 (2000).
12. Montalvo-Rodriguez, R. et al. Autohydrolysis of plant polysaccharides using transgenic hyperthermophilic enzymes. *Biotechnology and Bioengineering* 70, 151-159 (2000).
13. Xu, X. et al. Expression of a bacterial Î±-amylase gene in transgenic rice seeds. *Transgenic Research* 17, 645-650 (2008).
14. Martinez, D. et al. Genome sequencing and analysis of the biomass-degrading fungus *Trichoderma reesei* (syn. *Hypocrea jecorina*). *Nat Biotech* 26, 553-560 (2008).
15. Rubin, E. M. Genomics of cellulosic biofuels. *Nature* 454, 841-845 (2008).
16. Verma, D. & Daniell, H. Chloroplast vector systems for biotechnology applications. *Plant Physiol.* 145, 1129-1143 (2007).
17. Daniell, H., Lee, S. B., Panchal, T., & Wiebe, P. O. Expression of the native cholera toxin B subunit gene and assembly as functional oligomers in transgenic tobacco chloroplasts. *Journal of Molecular Biology* 311, 1001-1009 (2001).
18. De Cosa, B., Moar, W., Lee S B., Miller, M., & Daniell, H. Overexpression of the Bt cry2Aa2 operon in chloroplasts leads to formation of insecticidal crystals. *Nat Biotechnol* 19, 71-74 (2001).
19. Lee, S. B. et al. Accumulation of trehalose within transgenic chloroplasts confers drought tolerance. *Molecular Breeding* 11, 1-13 (2003).
20. Singh, N. D., Li, M., Lee, S. B., Schnell, D., & Daniell, H. *Arabidopsis* Tic40 Expression in Tobacco Chloroplasts Results in Massive Proliferation of the Inner Envelope Membrane and Upregulation of Associated Proteins. *Plant Cell* tpc (2008).
21. Daniell, H. Transgene containment by maternal inheritance: Effective or elusive? *Proceedings of the National Academy of Sciences* 104, 6879-6880 (2007).

22. Ruf, S., Karcher, D., & Bock, R. Determining the transgene containment level provided by chloroplast transformation. *Proceedings of the National Academy of Sciences* 104, 6998-7002 (2007).
23. Svab, Z. & Maliga, P. Exceptional transmission of plastids and mitochondria from the transplastomic pollen parent and its impact on transgene containment. *Proceedings of the National Academy of Sciences* 104, 7003-7008 (2007).
24. Gray, B. N., Ahner, B. A., & Hanson, M. R. High-level bacterial cellulase accumulation in chloroplast-transformed tobacco mediated by downstream box fusions. *Biotechnology and Bioengineering* xxx, xxx (2008).
25. Leelavathi, S., Gupta, N., Maiti, S., Ghosh, A., & Siva Reddy, V. Overproduction of an alkali- and thermo-stable xylanase in tobacco chloroplasts and efficient recovery of the enzyme. *Molecular Breeding* 11, 59-67 (2003).
26. Yu, L. X. et al. Expression of thermostable microbial cellulases in the chloroplasts of nicotine-free tobacco. *Journal of Biotechnology* 131, 362-369 (2007).
27. Brixey, P. J., Guda, C., & Daniell, H. The chloroplast psbA promoter is more efficient in *Escherichia coli* than the T7 promoter for hyperexpression of a foreign protein. *Biotechnology Letters* 19, 395-400 (1997).
28. Daniell, H., Ruiz, O. N., & Dhingra, A. Chloroplast Genetic Engineering to Improve Agronomic Traits. *Methods Mol Biol* 286, 111-138 (2005).
29. Verma, D., Samson, N. P., Koya, V., & Daniell, H. A protocol for expression of foreign genes in chloroplasts. *Nat. Protocols* 3, 739-758 (2008).
30. Guo, W., Gonzalez-Candelas, L., & Kolattukudy, P. E. Cloning of a novel constitutively expressed pectate lyase gene pelB from *Fusarium solani* f. sp. pisi (*Nectria haematococca*, mating type VI) and characterization of the gene product expressed in *Pichia pastoris*. *J. Bacteriol.* 177, 7070-7077 (1995).
31. Miller, G. L. Use of Dinitrosalicylic Acid Reagent for Determination of Reducing Sugar. *Analytical Chemistry* 31, 426-428 (1959).
32. Ghose, T. K. Measurement of cellulase activities. *Pure and Applied Chemistry* 59, 257-268 (1987).
33. Arlen P A et al. Field production and functional evaluation of chloroplast-derived interferon-alpha2b. *Plant Biotech J* 5, 511-525 (2007).
33. Cramer, C. L., Boothe, J. G. & Oishi, K. K. Transgenic plants for therapeutic proteins: linking upstream and downstream strategies. *Curr. Top. Microbiol. Immunol.* 240, 95-118 (1999).
34. Ruhlman, T. F., Ahangari, R. F., Devine, A. F., Samsam, M. F., & Daniell, H. Expression of cholera toxin B-proinsulin fusion protein in lettuce and tobacco chloroplasts—oral administration protects against development of insulitis in non-obese diabetic mice. *Plant Biotech J* 5, 495-510 (2007).
35. Bally, J. et al. Both the stroma and thylakoid lumen of tobacco chloroplasts are competent for the formation of disulphide bonds in recombinant proteins. *Plant Biotech J* 6, 46-61 (2008).
36. Chauvaux, S. et al. Calcium-binding affinity and calcium-enhanced activity of *Clostridium thermocellum* endoglucanase D. *Biochem. J.* 265, 261-265 (1990).
37. Zverlov, V. V., Velikodvorskaya, G. A., & Schwarz, W. H. A newly described cellulosomal cellobiohydrolase, CelO, from *Clostridium thermocellum*: investigation of the exo-mode of hydrolysis, and binding capacity to crystalline cellulose. *Microbiology* 148, 247-255 (2002).
38. Irwin D C, Spezio, M., Walker L P, & Wilson, D. B. Activity studies of eight purified cellulases: Specificity, synergism, and binding domain effects. *Biotechnology and Bioengineering* 42, 1002-1013 (1993).
39. Zhou, S. & Ingram, L. O, Synergistic Hydrolysis of Carboxymethyl Cellulose and Acid-Swollen Cellulose by Two Endoglucanases (CelZ and CelY) from *Erwinia chrysanthemi*. *J. Bacteriol.* 182, 5676-5682 (2000).
40. Gusakov A V et al. Design of highly efficient cellulase mixtures for enzymatic hydrolysis of cellulose. *Biotechnology and Bioengineering* 97, 1028-1038 (2007).
41. Yapo, B. M., Lerouge, P., Thibault, J. F., & Ralet, M. C. Pectins from citrus peel cell walls contain homogalacturonans homogenous with respect to molar mass, rhamnogalacturonan I and rhamnogalacturonan II. *Carbohydrate Polymers* 69, 426-435 (2007).
42. Rosgaard, L., Pedersen S, & Meyer, A. S. Comparison of different pretreatment strategies for enzymatic hydrolysis of wheat and barley straw. *Appl. Biochem. Biotechnol.* 143, 284-296 (2007).
43. Selig, M. J., Knoshaug, E. P., Adney, W. S., Himmel, M. E., & Decker, S. R. Synergistic enhancement of cellobiohydrolase performance on pretreated corn stover by addition of xylanase and esterase activities. *Bioresource Technology* 99, 4997-5005 (2008).
44. Rosgaard, L. et al. Evaluation of minimal *Trichoderma reesei* cellulase mixtures on differently pretreated Barley straw substrates. *Biotechnol. Prog* 23, 1270-1276 (2007).
45. Guo, W., González-Candelas, L., & Kolattukudy, P. E. Identification of a NovelpelDGene Expressed Uniquely in Planta by *Fusarium solani*f. sp. pisi (*Nectria haematococca*, Mating Type VI) and Characterization of Its Protein Product as an Endo-Pectate Lyase. *Archives of Biochemistry and Biophysics* 332, 305-312 (1996).
46. Soliday, C. L., Flurkey, W. H., Okita, T. W., & Kolattukudy, P. E. Cloning and structure determination of cDNA for cutinase, an enzyme involved in fungal penetration of plants. *Proceedings of the National Academy of Sciences of the United States of America* 81, 3939-3943 (1984).
47. Daniell, H., Datta, R., Varma, S., Gray, S., & Lee, S. B. Containment of herbicide resistance through genetic engineering of the chloroplast genome. *Nat Biotech* 16, 345-348 (1998).
48. Kumar, S. & Daniell, H. Engineering the Chloroplast Genome for Hyperexpression of Human Therapeutic Proteins and Vaccine Antigens in *Recombinant Gene Expression* 365-383 2004).
49. Crawford, M. S. & Kolattukudy, P. E. Pectate lyase from *Fusarium solani* f. sp. pisi: Purification, characterization, in vitro translation of the mRNA, and involvement in pathogenicity. *Archives of Biochemistry and Biophysics* 258, 196-205 (1987).
50. Gonzalez-Candelas, L. & Kolattukudy, P. E. Isolation and analysis of a novel inducible pectate lyase gene from the phytopathogenic fungus *Fusarium solani* f. sp. pisi (*Nectria haematococca*, mating population VI). *J. Bacteriol.* 174, 6343-6349 (1992).

REFERENCE LIST FOR EXAMPLES 10-11

Reference List

1. Robertson, G. P. et al. AGRICULTURE: Sustainable Biofuels Redux. *Science* 322, 49-50 (2008).

2. Sticklen, M. B. Plant genetic engineering for biofuel production: towards affordable cellulosic ethanol. *Nat. Rev. Genet.* 9, 433-443 (2008).
3. Merino, S. T. & Cherry, J. Progress and Challenges in Enzyme Development for Biomass Utilization in *Advances in Biochemical Engineering/Biotechnology* 95-120 (Springer Berlin/Heidelberg, 2007).
4. Wyman, C. E. et al. Coordinated development of leading biomass pretreatment technologies. *Bioresour. Technol.* 96, 1959-1966 (2005).
5. Grohmann, K., Baldwin, E. A., Buslig, B. S., & Ingram, L. O. Fermentation of galacturonic acid and other sugars in orange peel hydrolysates by the ethanologenic strain of *Escherichia coli*. *Biotechnology Letters* 16, 281-286 (1994).
6. Himmel, M. E. et al. Advanced bioethanol production technologies: a prospective. In ACS Symposium 666, 2-45. 1997. American Chemical Society Washington, D.C. Ref Type: *Conference Proceeding*.
7. Himmel, M. E., Ruth, M. F., & Wyman, C. E. Cellulase for commodity products from cellulosic biomass. *Current Opinion in Biotechnology* 10, 358-364 (1999).
8. Taylor II, L. E. et al. Heterologous expression of glycosyl hydrolases in planta: a new departure for biofuels. *Trends in Biotechnology* 26, 413-424 (2008).
9. Ziegelhoffer, T., Will, J., & ustin-Phillips, S. Expression of bacterial cellulase genes in transgenic alfalfa (*Medicago sativa* L.), potato (*Solanum tuberosum* L.) and tobacco (*Nicotiana tabacum* L.). *Molecular Breeding* 5, 309-318 (1999).
10. Kawazu, T. et al. Expression of a bacterial endoglucanase gene in tobacco increases digestibility of its cell wall fibers. *Journal of Bioscience and Bioengineering* 88, 421-425 (1999).
11. Dai, Z., Hooker, B. S., Anderson, D. B., & Thomas, S. R. Improved plant-based production of E1 endoglucanase using potato: expression optimization and tissue targeting. *Molecular Breeding* 6, 277-285 (2000).
12. Montalvo-Rodriguez, R. et al Autohydrolysis of plant polysaccharides using transgenic hyperthermophilic enzymes. *Biotechnology and Bioengineering* 70, 151-159 (2000).
13. Xu, X. et al. Expression of a bacterial α-amylase gene in transgenic rice seeds. *Transgenic Research* 17, 645-650 (2008).
14. Martinez, D. et al. Genome sequencing and analysis of the biomass-degrading fungus *Trichoderma reesei* (syn. *Hypocrea jecorina*). *Nat. Biotech.* 26, 553-560 (2008).
15. Rubin, E. M. Genomics of cellulosic biofuels. *Nature* 454, 841-845 (2008).
16. Verma, D. & Daniell, H. Chloroplast vector systems for biotechnology applications. *Plant Physiol.* 145, 1129-1143 (2007).
17. Daniell, H., Lee, S. B., Panchal, T., & Wiebe, P. O. Expression of the native cholera toxin B subunit gene and assembly as functional oligomers in transgenic tobacco chloroplasts. *Journal of Molecular Biology* 311, 1001-1009 (2001).
18. De Cosa, B., Moar, W., Lee, S. B., Miller, M., & Daniell, H. Overexpression of the Bt cry2Aa2 operon in chloroplasts leads to formation of insecticidal crystals. *Nat. Biotechnol.* 19, 71-74 (2001).
19. Lee, S. B. et al. Accumulation of trehalose within transgenic chloroplasts confers drought tolerance. *Molecular Breeding* 11, 1-13 (2003).
20. Singh, N. D., Li, M., Lee, S. B., Schnell, D., & Daniell, H. *Arabidopsis* Tic40 Expression in Tobacco Chloroplasts Results in Massive Proliferation of the Inner Envelope Membrane and Upregulation of Associated Proteins. *Plant Cell* 20, 3405-3417 (2008).
21. H. Daniell, S. Kumar and N. Duformantel (2005) Breakthrough in chloroplast genetic engineering of agronomically important crops. *Trends in Biotechnology*, 23: 238-245.
22. Daniell, H. Transgene containment by maternal inheritance: Effective or elusive? *Proceedings of the National Academy of Sciences* 104, 6879-6880 (2007).
23. H. Daniell (2002) Molecular strategies for gene containment in transgenic crops. *Nature Biotechnology* 20: 581-587.
24. Gray, B. N., et al., High-level bacterial cellulase accumulation in chloroplast-transformed tobacco mediated by downstream box fusions. *Biotechnology and Bioengineering* 102, 1045-1054 (2008).
25. Leelavathi, S., Gupta, & Siva Reddy, V. Overproduction of an alkali- and thermo-stable xylanase in tobacco chloroplasts and efficient recovery of the enzyme. *Molecular Breeding* 11, 59-67 (2003).
26. Yu, L. X. et al. Expression of thermostable microbial cellulases in the chloroplasts of nicotine-free tobacco. *Journal of Biotechnology* 131, 362-369 (2007).
27. Brixey, P. J., Guda, C., & Daniell, H. The chloroplast psbA promoter is more efficient in *Escherichia coli* than the T7 promoter for hyperexpression of a foreign protein. *Biotechnology Letters* 19, 395-400 (1997).
28. Daniell, H., Ruiz, O. N., & Dhingra, A. Chloroplast Genetic Engineering to Improve Agronomic Traits. *Methods Mol. Biol.* 286, 111-138 (2005).
29. Verma, D., Samson, N. P., Koya, V., & Daniell, H. A protocol for expression of foreign genes in chloroplasts. *Nat. Protocols* 3, 739-758 (2008).
30. Guo, W., Gonzalez-Candelas, L., & Kolattukudy, P. E. Cloning of a novel constitutively expressed pectate lyase gene pelB from *Fusarium solani* f. sp. pisi (*Nectria haematococca*, mating type VI) and characterization of the gene product expressed in *Pichia pastoris*. *J. Bacteriol.* 177, 7070-7077 (1995).
31. Miller, G. L. Use of Dinitrosalicylic Acid Reagent for Determination of Reducing Sugar. *Analytical Chemistry* 31, 426-428 (1959).
32. Ghose, T. K. Measurement of cellulase activities. *Pure and Applied Chemistry* 59, 257-268 (1987).
33. Cramer, C. L., Boothe, J. G. & Oishi, K. K. Transgenic plants for therapeutic proteins: linking upstream and downstream strategies. *Curr. Top. Microbiol. Immunol.* 240, 95-118 (1999).
34. Collins G B, Legg P D, Kasperbauer M C. Tobacco hybrid LAMD-609. *Crop Sci.* 14, 72-80 (1974).
35. Arlen P A et al. Field production and functional evaluation of chloroplast-derived interferon-alpha2b. *Plant Biotech. J.* 5, 511-525 (2007).
36. Ruhlman, T. F., Ahangari, R. F., Devine, A. F., Samsam, M. F., & Daniell, H. Expression of cholera toxin B-proinsulin fusion protein in lettuce and tobacco chloroplasts—oral administration protects against development of insulitis in non-obese diabetic mice. *Plant Biotech. J.* 5, 495-510 (2007).
37. Bally, J. et al. Both the stroma and thylakoid lumen of tobacco chloroplasts are competent for the formation of disulphide bonds in recombinant proteins. *Plant Biotech. J.* 6, 46-61 (2008).
38. Chauvaux, S. et al. Calcium-binding affinity and calcium-enhanced activity of *Clostridium thermocellum* endoglucanase D. *Biochem. J.* 265, 261-265 (1990).

39. Zverlov, V. V., Velikodvorskaya, G. A., & Schwarz, W. H. A newly described cellulosomal cellobiohydrolase, CelO, from *Clostridium thermocellum*: investigation of the exo-mode of hydrolysis, and binding capacity to crystalline cellulose. *Microbiology* 148, 247-255 (2002).
40. Irwin, D. C., Spezio, M., Walker, L. P., & Wilson, D. B. Activity studies of eight purified cellulases: Specificity, synergism, and binding domain effects. *Biotechnology and Bioengineering* 42, 1002-1013 (1993).
41. Zhou, S. & Ingram, L. O, Synergistic Hydrolysis of Carboxymethyl Cellulose and Acid-Swollen Cellulose by Two Endoglucanases (CelZ and CelY) from *Erwinia chrysanthemi*. *J. Bacteriol.* 182, 5676-5682 (2000).
42. Gusakov, A. V. et al. Design of highly efficient cellulase mixtures for enzymatic hydrolysis of cellulose. *Biotechnology and Bioengineering* 97, 1028-1038 (2007).
43. Yapo, B. M., Lerouge, P., Thibault, J. F., & Ralet, M. C. Pectins from citrus peel cell walls contain homogalacturonans homogenous with respect to molar mass, rhamnogalacturonan I and rhamnogalacturonan II. *Carbohydrate Polymers* 69, 426-435 (2007).
44. Rosgaard, L., Pedersen, S. & Meyer, A. S. Comparison of different pretreatment strategies for enzymatic hydrolysis of wheat and barley straw. *Appl. Biochem. Biotechnol.* 143, 284-296 (2007).
45. Selig, M. J., Knoshaug, E. P., Adney, W. S., Himmel, M. E., & Decker, S. R. Synergistic enhancement of cellobiohydrolase performance on pretreated corn stover by addition of xylanase and esterase activities. *Bioresource Technology* 99, 4997-5005 (2008).
46. Rosgaard, L. et al. Evaluation of minimal *Trichoderma reesei* cellulase mixtures on differently pretreated Barley straw substrates. *Biotechnol. Prog.* 23, 1270-1276 (2007).
47. Crawford, M. S. & Kolattukudy, P. E. Pectate lyase from *Fusarium solani* f. sp. pisi: Purification, characterization, in vitro translation of the mRNA, and involvement in pathogenicity. *Archives of Biochemistry and Biophysics* 258, 196-205 (1987).
48. Gonzalez-Candelas, L. & Kolattukudy, P. E. Isolation and analysis of a novel inducible pectate lyase gene from the phytopathogenic fungus *Fusarium solani* f. sp. pisi (*Nectria haematococca*, mating population VI). *J. Bacteriol.* 174, 6343-6349 (1992).
49. Holtzapple, M. T. Cellulose. In: Macrae R, Robinson R K, Saddler M J, editors. Encyclopedia of food science food technology and nutrition. London: Academic Press; 1993. p. 758-67.
50. Jarvis, M. Cellulose stacks up. *Science* 426, 611-2 (2003).
51. Zhang, Y. H. P. & Lynd, L. R. Toward an aggregated understanding of enzymatic hydrolysis of cellulose: non-complexed cellulase systems. *Biotechnol. Bioeng.* 88, 797-824 (2004).
52. Berner, R. A. The long-term carbon cycle, fossil fuels and atmospheric composition. *Nature* 426, 323-6 (2003).
53. Demain, A. L., Newcomb, M. & Wu, J. H. D. Cellulase, Clostridia, and ethanol. *Microbiol. Mol. Biol. Rev.* 69, 124-54 (2005).
54. O'Sullivan, A. C. Cellulose: the structure slowly unravels. *Cellulose* 4,173-207 (1997).
55. Lynd, L. R., Weimer, P. J. & van Zyl, W. H. Pretorius I S. Microbial cellulose utilization: fundamentals and biotechnology. *Microbiol. Mol. Biol. Rev.* 66, 506-77 (2002).
56. Wyman, C. E. Potential synergies and challenges in refining cellulosic biomass to fuels, chemicals, and power. *Biotechnol. Prog.* 19, 254-262 (2003).
57. Bayer, E. A., Lamed, R. & Himmel, M. E. The potential of cellulases and cellulosomes for cellulosic waste management. *Curr. Opin. Biotechnol.* 18, 237-245 (2007).
58. Knowles, J., Lehtovaara, P. & Teeri, T. Cellulase families and their genes. *Trends Biotechnol.* 5, 255-261 (1987).
59. Himmel, M. E., Adney, W. S., Baker, J. O., Nieves, R. A., Thomas, S. R. Cellulases: structure, function and applications. In: Wyman C E, editor. *Handbook on Bioethanol*. 144-61 (1993).
60. Zhang, Y—H. P., Himmel, M. E. & Mielenz, J. R. Outlook for cellulase improvement: Screening and selection strategies. *Biotechnol. Adv.* 24, 452-481 (2006).
61. Biely, P. Microbial xylanolytic systems, *Trends Biotechnology* 3, 286-290 (1985).
62. Tenkanen, M, Puls, J. & Potanen, K. Two major xylanases of *Trichoderma reesei*, *Enzyme and Microbial Technology* 14:566-574 (1992).
63. Polizeli, M. L. T. M., Rizzatti, A. C. S. & Monti, R. Xylanases from fungi: properties and industrial applications. *Applied Microbiology and Biotechnology*; 67, 577-591 (2005).
64. Baily, M. J. & Poulanen, K. Production of xylanases by strains of *Aspergillus*. Appl. *Microbiol. Biotechnol.* 30, 5-10 (1989).
65. Kolattukudy, P. E. Biopolyester Membranes of Plants: Cutin and Suberin. 208, 990-1000 (1980).
66. Kolattukudy, P. E. Polyesters in higher plants. *Adv. Biochem. Eng. Biotechnol.* 71, 1-49 (2001).
67. Kolattukudy, P. E. Detection of an N-terminal glucuronamide linkage in proteins. *Methods Enzymol.* 106, 210-7 (1984).
68. Egmond, M. R. & De Vlieg, J. *Fusarium solani* pisi cutinase. *Biochimie* 82, 1015-1021 (2000).
69. Sieber, P., Schorderet, M., Ryser, U., Buchala, A., Kolattukudy, P., Métraux, J. P. & Nawrath, C. Transgenic *Arabidopsis* plants expressing a fungal cutinase show alterations in the structure and properties of the cuticle and postgenital organ fusions. *Plant Cell* 12, 721-38 (2000).
70. Dhawan, S & Kaur, J. Microbial Mannanases: An Overview of Production and Applications, *Critical Reviews in Biotechnology*, 27, 197-216 (2007).
71. Moreira, L. R. S. & Filho, E. X. F. An overview of mannan structure and mannan-degrading enzyme systems. *Appl. Microbiol Biotechnol.* 795165-178 (2008).
72. Stalbrand, et al, Purification and characterization of two β-Mannanases from *Trichoderma reesei*, *Journal of Biotechnology*, 29, 229-242 (1993).
73. Mc Cleary, β-D Mannanase. *Methods in enzymology*, 160, 596-610 (1988).
74. Downie et al, A new assay for quantifying endo β-D mannanase activity using congo red dye. *Phytochemistry.* 36, 829-835, (1994).
75. Numan, M. T. Alpha-L-Arabinofuranosidases: the potential applications in biotechnology. *Journal of Industrial Microbiology and Biotechnology* 33, 247-260 (2006).
76. Poutanen, K. An alpha-L-arabinofuranosidase of *Trichoderma Reesei*. *Journal of Biotechnology* 7, 271-282 (1988).
77. Arora, D., et al. Comparison of two assay procedures for lignin peroxidase. *Enzyme and Microbial Technology* 28, 602-605 (2001).
78. Archibald, F. S. A New Assay for Lignin-Type Peroxidases Employing the Dye Azure B. *Applied and Environmental Microbiology*, 58, 3110-3116 (1992).
79. Mishra, K. C. et al., Functional role of the PE domain and immunogenicity of the *Mycobacterium tuberculosis* triacylglycerol hydrolase LipY. *Infect. Immun.* 76, 127-140 (2008).
80. Kouker, G., Jaeger, K. E. "Specific and Sensitive Plate Assay for Bacterial Lipases." *Applied and Environmental Microbiology* 53, 211-213 (1987).
81. Deb, C., Daniel. J. & Kolattukudy, P. E., "A Novel Lipase Belonging to the Hormone-sensitive Lipase Family Induced under Starvation to Utilize Stored Triacylglycerol in *Mycobacterium tuberculosis*." *The Journal of Biological Chemistry* 281, 3866-3875 (2006).

TABLE II

| No. | Source | Gene | Accession No. |
|---|---|---|---|
| 1 | *Aspergillus niger* CBS 513.88 | 1,4-beta-D-arabinoxylan arabinofuranohydrolase axhA | XM_001389961 |
| 2 | *Aspergillus niger* CBS 513.88 | endo-1,4-beta-xylanase A precursor (xynA) | XM_001389959 |
| 3 | *Aspergillus niger* | xylanase B | DQ174549 |
| 4 | *Aspergillus niger* | xylanase (XYNB) | AY536639 |
| 5 | *Aspergillus niger* | xylanase (XYN6) | AY536638 |
| 6 | *Aspergillus niger* | xylanase (XYN4) | U39785 |
| 7 | *Aspergillus niger* | xylanase (XYN5) | U39784 |
| 8 | *Aspergillus fumigatus* | XynC | DQ156555 |
| 9 | *Aspergillus fumigatus* | XynB | DQ156553 |
| 10 | *Bacillus licheniformis* | I5 beta-1,4-endoxylanase (xyn11) | DQ520129 |
| 11 | *Cryptococcus flavus* isolate I-11 | endo-1,4-beta xylanase (XYN1) | EU330207 |
| 12 | *Trichoderma viride* strain AS 3.3711 | endo-1,4-beta-xylanase (xyn2) | EF079061 |
| 13 | *Thermoascus aurantiacus* | xynA | AJ132635 |
| 14 | *Agaricus bisporus* | xlnA | Z83310 |
| 15 | *Thermobifida alba* | xylA | Z81013 |
| 16 | *Bacillus subtilis* | eglS gene for endo-1,4-beta-glucanase | Z29076 |
| 17 | *Chaetomium cupreum* | endo-1,4-beta-xylanase | EF026978 |
| 18 | *Paenibacillus polymyxa* | xyn D and glu B genes for endo-beta-(1,4)-xylanase and endo-beta-(1,3)(1,4)-glucanase | X57094 |
| 19 | *Neocallimastix frontalis* strain k13 | xylanase | DQ517887 |
| 20 | *Penicillium citrinum* | xynA gene for endo-1,4-beta-xylanase | AB198065 |
| 21 | *Agaricus bisporus* | endo-1,4-beta xylanase | Z83199 |
| 22 | *Bacillus* sp. (137) | endo-beta-1,4-xylanase | Z35497 |
| 23 | *Bacillus pumilus* | xynA | X00660 |
| 24 | *Aeromonas punctata* | XynX | AB015980 |
| 25 | *Penicillium canescens* | endo-1,4-beta-xylanase gene | AY756109 |
| 26 | *Cochliobolus carbonum* | endo-beta-1,4 xylanase (XYL4) | AY622513 |
| 27 | *Aspergillus* cf. *niger* BCC14405 | endo-1,4-beta-xylanase B (xylB) | AY551187 |
| 28 | *Bacillus alcalophilus* strain AX2000 | beta-1,4-xylanase (xynT) | AY423561 |
| 29 | *Trichoderma viride* strain YNUCC0183 | endo-1,4-beta-xylanase (XYL1) | AY370020 |
| 30 | *Thermotoga maritima* | endo-1,4-beta-xylanase B | AY339848 |
| 31 | *Trichoderma viride* strain YNUCC0183 | endo-1,4-beta-xylanase | AY320048 |
| 32 | *Gibberella zeae* | endo-1,4-beta-xylanase (xylA) | AY289919 |
| 33 | *Aeromonas caviae* | xynA gene for xylanase I | D32065 |
| 34 | *Bacillus pumilus* strain TX703 | beta-1,4-xylanase (xynK) gene, | AF466829 |
| 35 | *Fusarium oxysporum* f. sp. *lycopersici* | xylanase 4 protein (xyl4) | AF246831 |
| 36 | *Fusarium oxysporum* f. sp. *lycopersici* | xylanase 5 protein (xyl5) gene | AF246830 |
| 37 | *Penicillium purpurogenum* | endo-1,4-beta-D-xylanase A (XynA) | AF249328 |
| 38 | *Streptomyces* sp. S38 | xyl1 gene for endo-1,4-beta-xylanase | X98518 |
| 39 | *Bacillus* sp. NBL420 | endo-xylanase (xylS) | AF441773 |
| 40 | *Bacillus stearothermophilus* | endo-beta-1,4-xylanase (xynA) | U15985 |
| 41 | *Phanerochaete chrysosporium* strain ME446 | endo-1,4-B-xylanase B (xynB) | AF301902 to AF301905 |
| 42 | *Thermoascus aurantiacus* | endo-1,4-beta-xylanase A precursor (xynA) gene | AF127529 |
| 43 | *Neocallimastix patriciarum* | endo-1,4-beta-xylanase (xynC) gene | AF123252 |
| 44 | *Streptomyces avermitilis* | endo-1,4-beta-xylanase (xyl30) gene | AF121865 |
| 45 | *Cochliobolus carbonum* | beta-1,4-xylanase precursor (XYL3) gene | U58916 |
| 46 | *Trichoderma reesei* | beta-xylanase (XYN2) | U24191 |
| 47 | *Aspergillus tubingensis* | xylanase (xlnA) gene | L26988 |
| 48 | *Thermomonospora fusca* YX | endo 1,4-beta-D xylanase gene | U01242 |
| 49 | *Aspergillus fumigatus* Af293 | xylosidase: arabinofuranosidase | XM_750558 |

TABLE II-continued

| No. | Source | Gene | Accession No. |
|---|---|---|---|
| 50 | Aspergillus fumigatus Af293 | beta-xylosidase XylA | XM_747967 |
| 51 | Aspergillus fumigatus Af293 | beta-xylosidase | XM_744780 |
| 52 | Aspergillus fumigatus | Xld | DQ156554 |
| 53 | Vibrio sp. XY-214 | xloA | AB300564 |
| 54 | Aspergillus niger | xlnD | Z84377 |
| 55 | Bacteroides ovatus | xylosidase/arabinosidase gene | U04957 |
| 56 | Aspergillus clavatus NRRL 1 | xylosidase: arabinofuranosidase | XM_001275592 |
| 57 | Aspergillus clavatus NRRL 1 | beta-xylosidase | XM_001268537 |
| 58 | Neosartorya fischeri NRRL 181 | beta-xylosidase | XM_001261557 |
| 59 | Aspergillus niger CBS 513.88 | xylosidase xlnD | XM_001389379 |
| 60 | Aspergillus oryzae | beta-xylosidase A | AB013851 |
| 61 | Aspergillus oryzae | beta-1,4-xylosidase | AB009972 |
| 62 | Vibrio sp. XY-214 | xloA | AB300564 |
| 63 | Thermoanaerobacterium sp. 'JW/SL YS485' | xylosidase | EF193646 |
| 64 | Penicillium herquei | xylosidase | AB093564 |
| 65 | Bifidobacterium adolescentis strain Int57 | beta-xylosidase (bxyL) gene | DQ327717 |
| 66 | Aspergillus awamori | beta-xylosidase | AB154359 |
| 67 | Bacillus pumilus IPO | xynB gene for beta-xylosidase | X05793 |
| 68 | Pyrus pyrifolia PpARF2 | alpha-L-arabinofuranosidase/ beta-D-xylosidase | AB195230 |
| 69 | Clostridium stercorarium | bxlA gene for beta-xylosidase A | AJ508404 |
| 70 | Clostridium stercorarium | bxlB gene for beta-xylosidase B | AJ508405 |
| 71 | Aeromonas punctata | xysB, xyg genes for xylosidase B, alpha-glucuronidase, | AB022788 |
| 72 | Clostridium stercorarium | xynA gene for endo-xylanase | AJ508403 |
| 73 | Clostridium stercorarium | xyl43B gene for beta-xylosidase | AB106866 |
| 74 | Talaromyces emersonii | beta-xylosidase (bxl1) gene | A439746 |
| 75 | Thermoanaerobacterium sp. 'JW/SL YS485' | beta-xylosidase (xylB) and xylan esterase 1 (axe1) genes | AF001926 |
| 76 | Streptomyces thermoviolaceus | beta-xylosidase | AB110645 |
| 77 | Selenomonas ruminantium | xylosidase/arabinosidase (Xsa) gene | AF040720 |
| 78 | Bacillus pumilus | xylan 1,4-beta-xylosidase (xynB) | AF107211 |
| 79 | Bacillus stearothermophilus | b-xylosidase and gene for xylanase | D28121 |
| 80 | Azospirillum irakense | xylosidase/arabinofuranosidase (xynA) gene | AF143228 |
| 81 | Cochliobolus carbonum | major extracellular beta-xylosidase (XYP1) gene | AF095243 |
| 82 | Streptomyces lividans | BxlS (bxlS), BxlR (bxlR), BxlE (bxlE), BxlF (bxlF), BxlG (bxlG), and BxlA (bxlA) genes | AF043654 |
| 83 | Bacillus sp. KK-1 | beta-xylosidase (xylB) gene | AF045479 |
| 84 | Aspergllus nidulans | xlnD | Y13568 |
| 85 | T. reesei | beta-xylosidase | Z69257 |
| 86 | T. reesei | alpha-L-arabinofuranosidase | Z69252 |
| 87 | Clostridium stercorarium | xylA gene encoding xylosidase | D13268 |
| 88 | Butyrivibrio fibrisolvens | beta-D-xylosidase/alpha-L-arabinofuranosidase gene | M55537 |
| 89 | Thermoanaerobacter | beta-xylosidase (xynB) | M97883 |
| 90 | Paenibacillus sp. W-61 | exo-oligoxylanase | AB274730 |
| 91 | Aspergillus niger CBS 513.88 | arabinofuranosidase B abfB | XM_001396732 |
| 92 | Aspergillus niger CBS 513.88 | 1,4-beta-D-arabinoxylan arabinofuranohydrolase axhA | XM_001389961 |
| 93 | Aspergillus niger | alpha-L-arabinofuranosidase (ABF2) | U39942 |
| 94 | Aspergillus niger | alpha-L-arabinofuranosidase (abfA) | L29005 |
| 95 | Synthetic contruct | Alpha-L-arabinofuranosidase gene | BD143577 |
| 96 | Synthetic contruct | Alpha-L-arabinofuranosidase gene | BD143576 |
| 97 | Aureobasidium pullulans | alpha arabinofuranosidase (abfA) gene | AY495375 |

TABLE II-continued

| No. | Source | Gene | Accession No. |
|---|---|---|---|
| 98 | Geobacillus stearothermophilus strain KCTC 3012 | alpha-L-arabinofuranosidase (abf) gene | EF052863 |
| 99 | Hypocrea jecorina strain QM6a | Abf2 | AY281369 |
| 100 | Aspergillus sojae | alpha-L-arabinofuranosidase | AB033289 |
| 101 | Uncultured bacterium clone LCC-1 | arabinofuranosidase (deAFc) gene | DQ284779 |
| 102 | Penicillium purpurogenum | alpha-L-arabinofuranosidase 2 (abf2) gene | EF490448 |
| 103 | Acremonium cellulolyticus | Novel Alpha-L-arabinofuranosidase | DD354226 to DD354230 |
| 104 | Fusarium oxysporum f. sp. dianthi | abfB gene for alpha-L-arabinofuranosidase B | AJ310126 |
| 105 | Clostridium stercorarium | arfA gene for alpha-arabinofuranosidase | AJ508406 |
| 106 | Streptomyces thermoviolaceus | stxIV, stxI genes for alpha-L-arabinofuranosidase, xylanase I | AB110643 |
| 107 | Bifidobacterium longum B667 | arabinofuranosidase (abfB) gene | AY259087 |
| 108 | Aspergillus oryzae | Alpha-L-arabinofuranosidase gene | BD143578 |
| 109 | Aspergillus oryzae | Alpha-L-arabinofuranosidase gene | BD143575 |
| 110 | Clostridium cellulovorans | alpha-L-arabinofuranosidase ArfA, beta-galactosidase/alpha-L-arabinopyranosidase BgaA | AY128945 |
| 111 | Bacillus stearothermophilus | alpha-L-arabinofuranosidase (abfA) gene | AF159625 |
| 112 | Aspergillus oryzae strain: RIB40 | abfB for alpha-L-arabinofuranosidase B | AB073861 |
| 113 | Aspergillus oryzae strain: HL15 | abfB for alpha-L-arabinofuranosidase B | AB073860 |
| 114 | Penicillium purpurogenum | alpha-L-arabinofuranosidase (abf) gene | AF367026 |
| 115 | Cochliobolus carbonum | alpha-L-arabinofuranosidase (ARF2) gene | AF306764 |
| 116 | Cochliobolus carbonum | alpha-L-arabinofuranosidase (ARF1) gene | AF306763 |
| 117 | Cytophaga xylanolytica XM3 | alpha-L-arabinofuranosidase ArfII (arfII) gene | AF028019 |
| 118 | Cytophaga xylanolytica XM3 | alpha-L-arabinofuranosidase ArfI (arfI) gene | AF028018 |
| 119 | Clostridium stercorarium | alpha-L-arabinofuranosidase (arfB) gene | AF002664 |
| 120 | Aspergillus niger | tannase (TanAni) | DQ185610 |
| 121 | Neosartorya fischeri NRRL 181 | tannase and feruloyl esterase family protein (NFIA_029970) | XM_001262461 |
| 122 | Neosartorya fischeri NRRL 181 | tannase and feruloyl esterase family protein (NFIA_027990) | XM_001261621 |
| 123 | Neosartorya fischeri NRRL 181 | tannase and feruloyl esterase family protein (NFIA_047590) | XM_001257320 |
| 124 | Talaromyces stipitatus | faeC gene for ferulic acid esterase | AJ505939 |
| 125 | Aspergillus niger | faeB gene for feruloyl esterase | AJ309807 |
| 126 | Aspergillus awamori | AwfaeA gene for feruloylesterase | AB032760 |
| 127 | Penicillium chrysogenum | fae-1 | AB206474 |
| 128 | Neurospora crassa | ferulic acid esterase, type B | AJ293029 |
| 129 | Volvariella volvacea | acetyl xylan esterase | DQ888226 |
| 130 | Aspergillus fumigatus Af293 | acetyl xylan esterase | XM_750185 |
| 131 | Aspergillus niger CBS 513.88 | acetyl xylan esterase axeA | XM_001395535 |
| 132 | Neosartorya fischeri NRRL 181 | acetyl xylan esterase (Axe1) | XM_001258648 |
| 133 | A. niger | acetyl xylan esterase (axe A) | A22880 |
| 134 | Didymella rabiei | cut gene for cutinase | X65628 |
| 135 | Penicillium purpurogenum | acetyl xylan esterase (axeI) | AF529173 |
| 136 | Aspergillus oryzae | AoaxeA gene for acetyl xylan esterase | AB167976 |
| 137 | Fibrobacter succinogenes subsp. succinogenes S85 | acetyl xylan esterase Axe6A (axe6A) gene | AF180369 |
| 138 | Aspergillus ficuum | acetyl xylan esterase gene | AF331757 |

TABLE II-continued

| No. | Source | Gene | Accession No. |
|---|---|---|---|
| 139 | Bacillus pumilus | axe gene for acetyl xylan esterase | AJ249957 |
| 140 | Trichoderma reesei | acetyl xylan esterase | Z69256 |
| 141 | Thermoanaerobacterium sp. 'JW/SL YS485' | beta-xylosidase (xylB) and xylan esterase 1 (axe1) genes | AF001926 |
| 142 | Streptomyces thermoviolaceus | stxII, stxIII genes for xylanase II, acetyl xylan esterase | AB110644 |
| 143 | Streptomyces thermoviolaceus | stxIV, stxI genes for alpha-L-arabinofuranosidase, xylanase I | AB110643 |
| 144 | Streptomyces lividans | acetyl-xylan esterase (axeA) and xylanase B (xlnB) genes | M64552 |
| 145 | Abiotrophia para-adiacens | XynC gene for acetyl esterase | AB091396 |
| 146 | Orpinomyces sp. PC-2 | acetyl xylan esterase A (AxeA) | AF001178 |
| 147 | Caldocellum saccharolyticum | xylanase A (XynA), beta-xylosidase (XynB) and acetyl esterase (XynC) genes | M34459 |
| 148 | Talaromyces emersonii | alpha-glucuronidase (aGlu) gene | AF439788 |
| 149 | Aspergillus niger | aguA gene for alpha-glucuronidase | AJ290451 |
| 150 | Aspergillus fumigatus Af293 | alpha-glucuronidase | XM_748126 |
| 151 | Aspergillus niger CBS 513.88 | alpha-glucuronidase aguA | XM_001401166 |
| 152 | Aspergillus clavatus NRRL 1 | alpha-glucuronidase | XM_001274705 |
| 153 | Neosartorya fischeri NRRL 181 | alpha-glucuronidase | XM_001259233 |
| 154 | Neosartorya fischeri NRRL 181 | beta-galactosidase | XM_001259223 |
| 155 | Aureobasidium pullulans | alpha glucuronidase (aguA) | AY495374 |
| 156 | Aspergillus tubingensis | aguA gene | Y15405 |
| 157 | Thermotoga maritima | aguA gene | Y09510 |
| 158 | Trichoderma reesei | alpha-glucuronidase | Z68706 |
| 159 | Cellvibrio japonicus | alpha-glucuronidase (glcA67A) gene | AY065638 |
| 160 | Cellvibrio mixtus | alpha-glucuronidase (glcA67A) gene | AY065639 |
| 161 | Bacillus stearothermophilus strain T-1 | alpha-glucuronidase (aguA) gene | AF441188 |
| 162 | Bacillus stearothermophilus | alpha-glucuronidase (aguA) gene | AF221859 |
| 163 | Bacillus sp. TS-3 | abn-ts gene for arabinase-TS | AB061269 |
| 164 | Bacillus subtilis | endo-arabinase | D85132 |
| 165 | Aspergillus niger | endo-1,5-alpha-L-arabinase (abnA) gene | L23430 |
| 166 | Piromyces communis | endo-1,3-1,4-beta-glucanase (licWF3) | EU314936 |
| 167 | Neocallimastix patriciarum | endo-1,3-1,4-beta-glucanase (lic6) | EU314934 |
| 168 | Bacillus subtilis | lichenase(1,3;1,4-B-D-Glucan 4-glucanohydrolase) | E01881 |
| 169 | Clostridium thermocellum | lichenase licB gene for 1,3-(1,3:1,4)-beta-D-glucan 3(4)-glucanohydrolase | X58392 |
| 170 | Streptococcus equinus | beta-(1,3-1,4)-glucanase | Z92911 |
| 171 | Bacillus subtilis | bglS gene for beta-1,3-1,4-glucanase | Z46862 |
| 172 | Bacillus sp. | bgaA gene for lichenase | Z12151 |
| 173 | Clostridium thermocellum | licB gene for beta-1,3-1,4-glucanase | X63355 |
| 174 | Bacillus circulans | BGC gene for lichenase | X52880 |
| 175 | Anaeromyces sp. W-98 | lichenase (licB) | AF529296 |
| 176 | Bacillus licheniformis KCCM41412 | lichenase gene | AY383603 |
| 177 | Orpinomyces sp. PC-2 | lichenase (licA) | U63813 |
| 178 | Phanerochaete chrysosporium | endo-1,4-beta-D-mannanase | DQ779964 |
| 179 | Alicyclobacillus acidocaldarius | endo-beta-1,4-mannanase gene | DQ680160 |
| 180 | Clostridium cellulolyticum H10 GH26 | mannanase (man26A) and GH9 cellulase (cel9P) genes | DQ778334 |
| 181 | Aspergillus sulphureus | beta-mannanase gene | DQ328335 |

TABLE II-continued

| No. | Source | Gene | Accession No. |
|---|---|---|---|
| 182 | *Phanerochaete chrysosporium* strain RP78 | Man5C | DQ779965 |
| 183 | *Armillariella tabescens* | mannanase | DQ286392 |
| 184 | *Agaricus bisporus* | cel4 gene for CEL4a mannanase | AJ271862 |
| 185 | *Bacillus* sp. JAMB750 | man26A gene for mannanase | AB128831 |
| 186 | *Clostridium thermocellum* | man26B gene for mannanase 26B | AB044406 |
| 187 | *Bacillus circulans* isolate Y203 | mannanase gene | AY913796 |
| 188 | *Bacillus subtilis* strain Z-2 | mannose-6-phosphate isomerase and beta-1,4-mannanase genes | AY827489 |
| 189 | *Bacillus subtilis* strain A33 | beta-mannanase (man) gene | DQ269473 |
| 190 | *Bacillus subtilis* | mannanase gene | DQ351940 |
| 191 | *Bacillus circulans* isolate 196 | mannanase (man1) gene | AY907668 |
| 192 | *Bacillus* sp. JAMB-602 | amn5A gene for mannanase | AB119999 |
| 193 | *Agaricus bisporus* | mannanase CEL4b (cel4 gene) | Z50095 |
| 194 | *Piromyces* sp. | endo-b1,4-mannanase | X97520 |
| 195 | *Piromyces* sp. | endo-1,4 beta-mannanase | X97408 |
| 196 | *Piromyces* sp. | mannanase A | X91857 |
| 197 | *Clostridium thermocellum* | manA gene for mannanase A | AJ242666 |
| 198 | *Paecilomyces lilacinus* | beta-1,3-mannanase | AB104400 |
| 199 | *Bacillus circulans* | mannanase gene | AY623903 |
| 200 | *Bacillus circulans* | mannanase gene | AY540747 |
| 201 | *Dictyoglomus thermophilum* | beta-mannanase (manA) gene | AF013989 |
| 202 | *Cellvibrio japonicus* | manA gene | X82179 |
| 203 | *Bacillus circulans* | aman6 gene for alpha-1,6-mannanase | AB024331 |
| 204 | *Bacillus stearothermophilus* | beta-1,4-mannanase (manF), esterase (estA), and alpha-galactosidase (galA) genes | AF038547 |
| 205 | *Orpinomyces* sp. PC-2 | mannanase ManA (manA) | AF177206 |
| 206 | *Bacillus subtilis* | mannose-6-phosphate isomerase and endo-1,4-beta-mannosidase genes | AF324506 |
| 207 | *Rhodothermus marinus* | manA gene | X90947 |
| 208 | *Bacillus subtilis* | gene for beta-mannanase | D37964 |
| 209 | *Thermotoga maritima* | manA gene | Y17982 |
| 210 | *Cellulomonas fimi* | Man26A (man26A) gene | AF126471 |
| 211 | *Streptomyces lividans* | mannanase (manA) gene | M92297 |
| 212 | *Caldicellulosiruptor saccharolyticus* | beta-1,4-mannanase (manA) gene | U39812 |
| 213 | *Bacillus* sp. | beta-mannanase | AB016163 |
| 214 | *Bacillus circulans* | mannanase | AB007123 |
| 215 | *Caldicellulosiruptor saccharolyticus* | beta-D-mannanase (manA) | M36063 |
| 216 | *Caldocellum saccharolyticum* | beta-mannanase/endoglucanase (manA) | L01257 |
| 217 | *Aspergillus aculeatus* | mannanase (man1) | L35487 |
| 218 | *Trichoderma reesei* | beta-mannanase | L25310 |
| 219 | *Bacillus* sp. | beta-mannanase gene | M31797 |
| 220 | *Aspergillus niger* CBS 513.88 | beta-mannosidase mndA | XM_001394595 |
| 221 | *Aspergillus niger* CBS 513.88 | beta-galactosidase lacA | XM_001389585 |
| 222 | *Aspergillus clavatus* NRRL 1 | beta-mannosidase | XM_001268087 |
| 223 | *Neosartorya fischeri* NRRL 181 | beta-galactosidase | XM_001259270 |
| 224 | *Neosartorya fischeri* NRRL 181 | beta-galactosidase | XM_001259223 |
| 225 | *Aspergillus niger* | mndA gene for beta-mannosidase | AJ251874 |
| 226 | *Aspergillus niger* | aglC gene for alpha-galactosidase C | AJ251873 |
| 227 | *Aspergillus terreus* NIH2624 | beta-glucuronidase | XM_001218602 |
| 228 | *Emericella nidulans* | beta-mannosidase | DQ490488 |
| 229 | *Thermotoga neopolitana* | manA gene | Y17983 |
| 230 | *Thermotoga neopolitana* | manB gene | Y17981 |
| 231 | *Thermotoga maritima* | manB gene | Y17980 |

TABLE II-continued

| No. | Source | Gene | Accession No. |
|---|---|---|---|
| 232 | *Thermobifida fusca* | manB gene for beta-D-mannosidase | AJ489440 |
| 233 | *Thermotoga maritima* | manA gene | Y17982 |
| 234 | *Pyrococcus furiosus* | beta-mannosidase (bmnA) gene | U60214 |
| 235 | *Aspergillus aculeatus* | beta-mannosidase | AB015509 |
| 236 | *Bacteroides fragilis* | glaB gene for alpha-galactosidase | AM109955 |
| 237 | *Bacteroides fragilis* | glaA gene for alpha-galactosidase | AM109954 |
| 238 | *Aspergillus fumigatus* Af293 | alpha-galactosidase | XM_744777 |
| 239 | *Aspergillus fumigatus* Af293 | alpha-galactosidase | XM_743036 |
| 240 | *Aspergillus niger* CBS 513.88 | extracellular alpha-glucosidase aglU | XM_001402016 |
| 241 | *Aspergillus niger* CBS 513.88 | alpha-galactosidase aglA *Aspergillus niger* (aglA) | XM_001390808 |
| 242 | *Aspergillus niger* CBS 513.88 | alpha-galactosidase aglB | XM_001400207 |
| 243 | *Bacteroides thetaiotaomicron* | glaB gene for alpha-galactosidase | AM109957 |
| 244 | *Bacteroides thetaiotaomicron* | glaA gene for alpha-galactosidase | AM109956 |
| 245 | *Streptomyces avermitilis* MA-4680 | gla gene for alpha-galactosidase | AM109953 |
| 246 | *Aspergillus clavatus* NRRL 1 | alpha-galactosidase | XM_001276326 |
| 247 | *Bifidobacterium longum* | alpha-galactosidase (aglL) | AF160969 |
| 248 | *Neosartorya fischeri* NRRL 181 | alpha-galactosidase | XM_001266319 |
| 249 | *Aspergillus niger* | aglC gene for alpha-galactosidase C | AJ251873 |
| 250 | *Aspergillus niger* | aglB gene | Y18586 |
| 251 | *Lactobacillus fermentum* strain CRL722 | alpha-galactosidase (melA) gene | AY612895 |
| 252 | *Emericella nidulans* | alpha-galactosidase (AN8138-2) | DQ490515 |
| 253 | *Emericella nidulans* | alpha-galactosidase | DQ490505 |
| 254 | *Pseudoalteromonas* sp. KMM 701 | alpha-galactosidase gene | DQ530422 |
| 255 | *Lactobacillus plantarum* | melA gene for alpha-galactosidase | AJ888516 |
| 256 | *Bifidobacterium bifidum* | alpha-galactosidase (melA) gene | DQ438978 |
| 257 | *Lachancea thermotolerans* | MELth2 gene for alpha-galactosidase | AB257564 |
| 258 | *Lachancea thermotolerans* | MELth1 gene for alpha-galactosidase | AB257563 |
| 259 | *Clostridium stercorarium* | Thermostable ALPHA-galactosidase gene | BD359178 |
| 260 | *Bifidobacterium breve* strain 203 | alpha-galactosidase (aga2) gene | DQ267828 |
| 261 | *Clostridium josui* | agaA gene for alpha-galactosidase | AB025362 |
| 262 | *Trichoderma reesei* | alpha-galactosidase | Z69253 |
| 263 | *Saccharomyces mikatae* | alpha-galactosidase MEL gene | X95506 |
| 264 | *Saccharomyces paradoxus* | alpha-galactosidase MEL gene | X95505 |
| 265 | *Saccharomyces cerevisiae* | alpha-galactosidase | Z37510 |
| 266 | *Saccharomyces cerevisiae* | alpha-galactosidase | Z37511 |
| 267 | *Saccharomyces cerevisiae* | alpha-galactosidase | Z37508 |
| 268 | *Saccharomyces cerevisiae* | MEL1 gene for alpha-galactosidase | X03102 |
| 269 | *Penicillium simplicissimum* | alpha-galactosidase 1 | AJ009956 |
| 270 | *Clostridium stercorarium* | aga36A gene for alpha-galactosidase | AB089353 |
| 271 | *Bifidobacterium breve* | alpha-galactosidase (aga) gene | AF406640 |
| 272 | *Lactobacillus plantarum* | alpha-galactosidase (melA) gene | AF189765 |
| 273 | *Mycocladus corymbiferus* | Thermostable alpha-galactosidase | BD082887 to BD082889 |
| 274 | *Bacillus stearothermophilus* | alpha-galactosidase AgaB (agaB) | AY013287 |

TABLE II-continued

| No. | Source | Gene | Accession No. |
|---|---|---|---|
| 275 | *Bacillus stearothermophilus* | alpha-galactosidase AgaA (agaA) | AY013286 |
| 276 | *Bacillus stearothermophilus* | alpha-galactosidase AgaN (agaN) | AF130985 |
| 277 | *Carnobacterium piscicola* | AgaA (agaA) | AF376480 |
| 278 | *Thermus* sp. T2 | alpha galactosidase | AB018548 |
| 279 | *Phanerochaete chrysosporium* | alpha-galactosidase (agal) gene | AF246263 |
| 280 | *Phanerochaete chrysosporium* | alpha-galactosidase (agal) gene | AF246262 |
| 281 | *Zygosaccharomyces mrakii* | MELr gene for alpha-galactosidase | AB030209 |
| 282 | *Thermus thermophilus* strain TH125 | beta-glycosidase (bglT) gene | AF135400 |
| 283 | *Torulaspora delbrueckii* | MELt gene for alpha-galactosidase | AB027130 |
| 284 | *Penicillium purporogenum* | alpha-galactosidase | AB008367 |
| 285 | *Mortierella vinacea* | alpha-galactosidase | AB018691 |
| 286 | *Thermotoga neapolitana* | alpha-1,6-galactosidase (aglA) gene | AF011400 |
| 287 | *Trichoderma reesei* | alpha-galactosidase | Z69254 |
| 288 | *Trichoderma reesei* | alpha-galactosidase | Z69255 |

TABLE III

| No | Nucleotide ID | Gene name | Enzyme class | Species |
|---|---|---|---|---|
| 1 | AM397952 cDNA | lip3 | EC 1.11.1.14 | *Phlebia tremellosa* |
| 2 | AM397951 cDNA | lip2 | EC 1.11.1.14 | *Phlebia tremellosa* |
| 3 | AJ745879 cDNA | mnp | EC 1.11.1.13 | *Trametes versicolor* |
| 4 | AJ745080 cDNA | mrp | EC 1.11.1.13 | *Trametes versicolor* |
| 5 | AY836676 cDNA | mnp5 | EC 1.11.1.13 | *Pleurotus pulmonarius* |
| 6 | AJ315701 cDNA | mnp2 | EC 1.11.1.13 | *Phlebia radiate* |
| 7 | AJ310930 cDNA | mnp3 | EC 1.11.1.13 | *Phlebia radiate* |
| 8 | AB191466 cDNA | tclip | EC 1.11.1.14 | *Trametes cervina* |
| 9 | M24082 | Lig1 | EC 1.11.1.14 | *Phanerochaete chrysosporium* |
| 10 | J04980 cDNA | mp-1 | EC 1.11.1.13 | *Phanerochaete chrysosporium* |
| 11 | M80213 M36814 cDNA | lip | EC 1.11.1.14 | *Phanerochaete chrysosporium* |
| 12 | AF074951 cDNA | cdh | EC 1.1.99.18 | *Corynascus heterothallicus* |
| 13 | X97832 | cdh | EC 1.1.99.18 | *Phanerochaete chrysosporium* |
| 14 | X88897 cDNA | cdh | EC 1.1.99.18 | *Phanerochaete chrysosporium* |
| 15 | U50409 | Cdh-1 | EC 1.1.99.18 | *Phanerochaete chrysosporium* |
| 16 | U65888 | Cdh-2 | EC 1.1.99.18 | *Phanerochaete chrysosporium* |
| 17 | U46081 | cdh | EC 1.1.99.18 | *Phanerochaete chrysosporium* |
| | D90341 | celCCD | 3.2.1.4 | *Clostridium cellulolyticum* |
| | AY339624 | EglA | | *Bacillus pumilus* |
| | D83704 | celJ, celK | | *Clostridium thermocellum* |
| | EF371844 | egl | | *Ralstonia solanacearum* |
| | EF371842 | egl | | *Ralstonia solanacearum* |
| | L02544 | cenD | EC.3.2.1.4 | *Cellulomonas fimi* |
| | EU055604 | cel9B | | *Fibrobacter succinogenes* |
| | EF093188 | ega | | *Bacillus* sp. AC-1 |
| | EF620915 | endoglucanase | | *Bacillus pumilus* |
| | AB167732 | egl | | *Paenibacillus* sp. KSM-N659 |
| | AB167731 | egl | | *Paenibacillus* sp. KSM-N440 |
| | AB167730 | egl | | *Paenibacillus* sp. |
| | AB167729 | egl | | *Paenibacillus* sp. |
| | EF205153 | endoglucanase | | *Thermomonospora* sp. MTCC 5117 |
| | DQ657652 | egl | | *Ralstonia solanacearum* strain UW486 |
| | AJ616005 | celA | | *Bacillus licheniformis* |
| | DQ294349 | eglA | | *Azoarcus* sp. BH72 |

TABLE III-continued

| No Nucleotide ID | Gene name | Enzyme class | Species |
|---|---|---|---|
| DQ923327 | eg1 | | uncultured Butyrivibrio sp |
| Z12157 | cela1 | | Streptomyces halstedii |
| AJ275974 | celI | | Clostridium thermocellum |
| AB179780 | cel5A | | Eubacterium cellulosolvens |
| DQ176867 | celK | | Pectobacterium carotovorum (Erwinia carotovora) |
| X57858 | cenC | | Cellulomonas fimi |
| AY298814 | cel5B | | Thermobifida fusca |
| X79241 | celV1 | | Pectobacterium carotovorum |
| AY646113 | engO | | Clostridium cellulovorans |
| AB028320 | egV | | Ruminococcus albus |
| AB016777 | egIV | | Ruminococcus albus |
| X76640 | celA | | Myxococcus xanthus |
| Y12512 | celA | | Bacillus sp. BP-23 |
| Z83304 | endA | | Ruminococcus flavefaciens |
| Z86104 | celB, celC | | Anaerocellum thermophilum |
| Z77855 | celD | | Anaerocellum thermophilum |
| X76000 | celV | | Pectobacterium carotovorum (Erwinia carotovora) |
| X73953 | eglS | | Streptomyces rochei |
| X54932 | celB | | Ruminococcus albus |
| X54931 | celA | | Ruminococcus albus |
| X52615 | endoglucanase | | Cellvibrio japonicus |
| X69390 | celG | | Clostridium thermocellum |
| X03592 | celB | | Clostridium thermocellum |
| X17538 | end1 | | Butyrivibrio fibrisolvens |
| AJ308623 | celA | | Alicyclobacillus acidocaldarius |
| AJ304415 | engXCA | | Xanthomonas campestris pv. campestris |
| AJ133614 | celB | | Bacillus sp. BP-23 |
| AY445620 | cel9A | | Bacillus licheniformis |
| AF025769 | celB | | Erwinia carotovora subsp. carotovora |
| L20093 | E4 | | Thermomonospora fusca |
| AJ551527 | celB | | Alicyclobacillus acidocaldarius |
| M64363 | celF | | Clostridium thermocellum |
| AB044407 | celT | | Clostridium thermocellum |
| AB059267 | egl257 | | Bacillus circulans |
| AF363635 | engA | | Bacillus amyloliquefaciens |
| M31311 | eglA | | Clostridium saccharobutylicum |
| AF109242 | celZ | | Erwinia chrysanthemi |
| M31311 | eglA | | Clostridium saccharobutylicum |
| AF033262 | celA | | Pseudomonas sp. YD-15 |
| M84963 | endoglucanase | | Bacillus subtilis |
| AB047845 | celQ | | Clostridium thermocellum |
| AY007311 | celA | | Clavibacter michiganensis subsp. sepedonicus |
| AF132735 | engK | | Clostridium cellulovorans |
| U34793 | engH | | Clostridium cellulovorans |
| AF206716 | endoglucanase | | Bacillus pumilus |
| AF113404 | cel6A | | Cellulomonas pachnodae |
| X04584 | celD | | Clostridium thermocellum |
| U51222 | celA2 | | Streptomyces halstedii |
| U27084 | cel | | Bacillus sp |
| L02868 | celA | | Clostridium longisporum |
| AF067428 | Cel5A | | Bacillus agaradhaerens |
| L01577 | E3, E4, E5 | | Thermobifida fusca |
| M73321 | E2 | | Thermobifida fusca |
| L20094 | E1 | | Thermobifida fusca |
| U94825 | Endoglucanase | | Actinomyces sp. 40 |
| U37056 | engF | | Clostridium cellulovoran |
| U33887 | celG | | Fibrobacter succinogenes |
| U08621 | celB | | Ruminococcus flavefaciens FD-1 |
| Y00540 | celZ | | Erwinia chrysanthemi |
| U16308 | celC | | Caldocellum saccharolyticum |
| K03088 | celA | | Clostridium thermocellum |
| M93096 | celCCA | | Clostridium cellulolyticum |
| L03800 | celE | | Ruminococcus flavefaciens |
| L13461 | celM | | Clostridium thermocellum |
| M74044 | celY | | Erwina chrysanthemi |
| X13602 | celB | | Caldocellum saccharolyticum |
| AB078006 | CBH II | | Streptomyces sp. M23 |
| X80993 | cbhA | | Clostridium thermocellum |
| AJ005783 | cbhA, celK | | Clostridium thermocellum |
| AY494547 | cbhA | | Clostridium thermocellum |
| AF039030 | celK | | Clostridium thermocellum |
| L38827 | cbhB | EC 3.2.1.91 | Cellulomonas fimi |
| L25809 | cbhA | | Cellulomonas fimi |
| EU314939 | cbhYW23-4 | | Piromyces rhizinflatus |
| EU314933 | cbh6 | | Neocallimastix patriciarum |

TABLE III-continued

| No | Nucleotide ID | Gene name | Enzyme class | Species |
|---|---|---|---|---|
| | EF397602 | cbh1 | | *Penicillium decumbens* |
| | AB298323 | cel1, cel2 | | *Polyporus arcularius* |
| | AB298322 | cbh I | | *Polyporus arcularius* |
| | EU038070 | cbh I | | *Fusicoccum* sp. BCC4124 |
| | EF624464 | cbh | | *Thermomyces lanuginosus* |
| | AM262873 | cbhI-2 | | *Pleurotus ostreatus* |
| | AM262872 | cbhI-4 | | *Pleurotus ostreatus* |
| | AM262871 | cbhI-3 | | *Pleurotus ostreatus* |
| | AM262993 | cbhI-1 | | *Pleurotus ostreatus* |
| | XM_745507 | Cbh-celD | | *Aspergillus fumigatus* |
| | AY973993 | exo-(cbhI) | | *Penicillium chrysogenum* |
| | AF421954 | cbh | | *Thermoascus aurantiacus* |
| | XM_001389539 | cbhB | | *Aspergillus niger* |
| | XM_001391971 | cbhA | | *Aspergillus niger* |
| | DQ864992 | CBHII | | *Trichoderma viride* |
| | EF222284 | cbh3 | | *Chaetomium thermophilum* |
| | X69976 | cbh1 | | *Hypocrea koningii/Trichoderma koningii* |
| | Z29653 | exo-cbhI.2 | | *Phanerochaete chrysosporium* |
| | Z22527 | exo-cbhI | | *Phanerochaete chrysosporium* |
| | X53931 | cbh | | *Trichoderma viride* |
| | X54411 | Pccbh1-1 | | *Phanerochaete chrysosporium* |
| | DQ085790 | cbh3 | | *Chaetomium thermophilum* |
| | AY559104 | cbhII-I | | *Volvariella volvacea* |
| | AY559102 | cbhI-I | | *Volvariella volvacea* |
| | D86235 | cbh1 | | *Trichoderma reesei* |
| | DQ504304 | cbhII | | *Hypocrea koningii* strain 3.2774 |
| | E00389 | cbh | | *Hypocrea jecorina/Trichoderma reesei* |
| | AY706933 | cbh-C | | *Gibberella zeae* |
| | AY706932 | cbh-C | | *Fusarium venenatum* |
| | AY706931 | cbh-C | | *Gibberella zeae* |
| | DQ020255 | cbh-6 | | *Chaetomium thermophilum* |
| | AY954039 | cbh | | *Schizophyllum commune* |
| | D63515 | cbh-1 | | *Humicola grisea* var. *thermoidea* |
| | Z50094 | cel2-cbh | | *Agaricus bisporus* |
| | Z50094 | Exocellobiohydrolase | | *Agaricus bisporus* |
| | Z22528 | exo-cbh I | | *Phanerochaete chrysosporium* |
| | AY840982 | cbh | | *Thermoascus aurantiacus* var. *levisporus* |
| | AY761091 | cbhII | | *Trichoderma parceramosum* |
| | AY651786 | cbhII | | *Trichoderma parceramosum* |
| | AY690482 | cbhI | | *Penicillium occitanis* |
| | CQ838174 | cbh | | *Malbranchea cinnamomea* |
| | CQ838172 | cbh | | *Stilbella annulata* |
| | CQ838150 | cbh | | *Chaetomium thermophilum* |
| | AY328465 | celB-cbh | | *Neocallimastix frontalis* |
| | AB177377 | cexI, cbh | | *Irpex lacteus* |
| | AY531611 | cbh-I | | *Trichoderma asperellum* |
| | AY116307 | cbh-7 | | *Cochliobolus heterostrophus* |
| | AB002821 | cbh-I | | *Aspergillus aculeatus* |
| | AF478686 | cbh-1 | | *Thermoascus aurantiacus* |
| | AY368688 | cbh-II | | *Trichoderma viride* strain CICC 13038 |
| | AY368686 | cbhI | | *Trichoderma viride* |
| | AY091597 | Cel6E | | *Piromyces* sp. E2 |
| | AX657625 | cbh | | *Phanerochaete chrysosporium* |
| | AX657629 | cbh | | *Aspergillus* sp. |
| | AX657633 | cbh | | *Pseudoplectania nigrella* |
| | U97154 | celF | | *Orpinomyces* sp. PC-2 |
| | U97152 | celD-cbh | | *Orpinomyces* sp. PC-2 |
| | AF439935 | cbh1A | | *Talaromyces emersonii* |
| | AB021656 | cbhI | | *Trichoderma viride* |
| | AB089343 | cbh | | *Geotrichum* sp. M128 |
| | AB089436 | celC-cbh | | *Aspergillus oryzae* |
| | A35269 | cbh | | *Fusarium oxysporum* |
| | AF439936 | cbhII | | *Talaromyces emersonii* |
| | AY075018 | cbhII | | *Talaromyces emersonii* |
| | AY081766 | cbhI | | *Talaromyces emersonii* |
| | AF378175 | cbh1 | | *Trichoderma koningii* |
| | AF378173 | cbh2 | | *Trichoderma koningii* |
| | AF378174 | cbh2 | | *Trichoderma koningii* |
| | AF244369 | cbhII-1 | | *Lentinula edodes* |
| | L22656 | cbh1-4 | | *Phanerochaete chrysosporium* |
| | L24520 | cel3AC-cbh | | *Agaricus bisporus* |
| | M22220 | cbhI | | *Phanerochaete chrysosporium* |
| | AY050518 | cbh-II | | *Pleurotus sajor-caju* |
| | AF223252 | cbh-1 | | *Trichoderma harzianum* |
| | AF177205 | celI-cbh | | *Orpinomyces* sp. PC-2 |
| | AF177204 | celH-cbh | | *Orpinomyces* sp. PC-2 |
| | AF302657 | cbh-II | | *Hypocrea jecorina* |
| | AF156269 | cbh-2 | | *Aspergillus niger* |

TABLE III-continued

| No | Nucleotide ID | Gene name | Enzyme class | Species |
|---|---|---|---|---|
|  | AF156268 | cbh-2 |  | *Aspergillus niger* |
|  | AF123441 | cbh1.2 |  | *Humicola grisea* var. *thermoidea* |
|  | U50594 | cbh1.2 |  | *Humicola grisea* |
|  | M55080 | cbh-II |  | *Trichoderma reesei* |
|  | M16190 | cbh-II |  | *Trichoderma reesei* |
| 1 | NC_000961 | endoglucanase | EC 3.1.2.4 | *Pyrococcus horikoshii* |
| 2 | NC_000961/U33212/ AX467594 | cel5A | EC 3.1.2.4 | *Acidothermus cellulolyticus* 11B; ATCC 43068 |
| 3 | M32362 | cel5A | EC 3.1.2.4 | *Clostridium cellulolyticum* |
| 4 | M22759 | celE, cel5C | EC 3.2.1.4 | *Clostridium thermocellum* |
| 5 | AJ307315 | celC | EC 3.2.1.4 | *Clostridium thermocellum* |
| 6 | AJ275975 | celO | EC 3.2.1.91 | *Clostridium thermocellum* |
| 7 | X03592 | celB/cel5A | EC 3.2.1.4 | *Clostridium thermocellum* |
| 8 | Z29076 | eglS | EC 3.2.1.4 | *Bacillus subtilis* |
| 9 | M33762 | celB | EC 3.2.1.4 | *Bacillus lautus* (strain PL236) |
| 10 | L25809 | cbhA | EC 3.2.1.91 | *Cellulomonas fimi* |
| 11 | M15823 | cenA/cel6A | EC 3.2.1.4 | *Cellulomonas fimi* |
| 12 | M73321 | cel6A | EC 3.2.1.4 | *Thermobifida fusca* |
| 13 | U18978 | cel6B | EC 3.2.1.91 | *Thermomonospora fusca* |
| 14 | X65527 | cellodextrinase D | EC 3.2.1.74 | *Cellvibrio japonicus* |
| 15 | L06134 | ggh-A | EC 3.2.1.74 | *Thermobispora bispora* |
| 16 | U35425 | cdxA | EC 3.2.1.74 | *Prevotella bryantii* |
| 17 | EU352748 | cel9D | EC 3.2.1.74 | *Fibrobacter succinogenes* |
| 18 | AAL80566 | bglB | EC 3.2.1.21 | *Pyrococcus furiosus* |
| 19 | Z70242 | bglT | EC 3.2.1.21 | *Thermococcus* sp |
| 20 | M96979 | bglA | EC 3.2.1.21 | *Bacillus circulans* |
| 21 | AB009410 | beta-glucosidase | EC 3.2.1.21 | *Bacillus* sp. GL1 |
| 22 | D88311 D84489 | beta-D-glucosidase | EC 3.2.1.21 | *Bifidobacterium breve* |
| 23 | AAQ00997 | BglA | EC 3.2.1.21 | *Clostridium cellulovorans* |
| 24 | X15644 | bglA | EC 3.2.1.21 | *Clostridium thermocellum* |
| 25 | AAA25311 | BglB | EC 3.2.1.21 | *Thermobispora bispora* |
| 26 | AB198338 | bglA | EC 3.2.1.21 | *Paenibacillus* sp. HC1 |
| 27 | AF305688 | Bgl1 | EC 3.2.1.21 | *Sphingomonas paucimobilis* |
| 28 | CAA91220 | beta-glucosidase | EC 3.2.1.21 | *Thermoanaerobacter brockii* |
| 29 | CAA52276 | beta-glucosidase | EC 3.2.1.21 | *Thermotoga maritime* |
| 30 | AAO15361 | beta-glucosidase | EC 3.2.1.21 | *Thermus caldophilus* |
| 31 | Z97212 | beta-glucosidase | EC 3.2.1.21 | *Thermotoga neapolitana* |
| 32 | AB034947 | beta-glucosidase | EC 3.2.1.21 | *Thermus* sp. Z-1 |
| 33 | M31120 | beta-glucosidase | EC 3.2.1.21 | *Butyrivibrio fibrisolvens* |
| 34 | D14068 | beta-glucosidase | EC 3.2.1.21 | *Cellvibrio gilvus* |
| 35 | AF015915 | Bg1 | EC 3.2.1.21 | *Flavobacterium meningosepticum* |
| 36 | U08606 | bgxA | EC 3.2.1.21 | *Erwinia chrysanthemi* |
| 37 | Z94045 | bglZ | EC 3.2.1.21 | *Clostridium stercorarium* |
| 38 | AY923831 | bglY | EC 3.2.1.21 | *Paenibacillus* sp. |
| 38 | Z56279 | xglS | EC 3.2.1.21 | *Thermoanaerobacter brockii* |
| 39 | CQ893499 | bglB | EC 3.2.1.21 | *Thermotoga maritime* |
|  | DQ916114 | beta-glucosidase (RG11) | EC 3.2.1.21 | uncultured bacterium |
|  | DQ182493 | beta-glucosidase | EC 3.2.1.21 | uncultured bacterium |
|  | DQ916117 | beta-glucosidase | EC 3.2.1.21 | uncultured bacterium |
|  | DQ022614 | umbgl3A | EC 3.2.1.21 | uncultured bacterium |
|  | DQ916115 | RG12 beta-glucosidase gene | EC 3.2.1.21 | uncultured bacterium |
|  | DQ182494 | beta-glucosidase (umbgl3C) | EC 3.2.1.21 | uncultured bacterium |
|  | DQ916118 | Uncultured bacterium clone RG25 | EC 3.2.1.21 | uncultured bacterium |
|  | DQ916116 | RG14 beta-glucosidase gene | EC 3.2.1.21 | uncultured bacterium |
|  | U12011 | Bgl | EC 3.2.1.21 | unidentified bacterium |
|  | AB253327 | bgl1B | EC 3.2.1.21 | *Phanerochaete chrysosporium* |
|  | AB253326 | beta-glucosidase | EC 3.2.1.21 | *Phanerochaete chrysosporium* |
|  | AJ276438 | beta-glucosidase | EC 3.2.1.21 | *Piromyces* sp. E2 |
|  | AF439322 | bg1 | EC 3.2.1.21 | *Talaromyces emersonii* |
|  | D64088 cDNA | beta-glucosidase 1 | EC 3.2.1.21 | *Aspergillus aculeatus* |
|  | DQ490467 cDNA | beta-glucosidase 1 | EC 3.2.1.21 | *Emericella nidulans* |
|  | AAB27405 | beta-glucosidase | EC 3.2.1.21 | *Aspergillus niger* |
|  | AX616738 | beta-glucosidase | EC 3.2.1.21 | *Aspergillus oryzae* |
|  | AJ130890 |  | EC 3.2.1.21 | *Botryotinia fuckeliana* |
|  | L21014 | beta-glucosidase | EC 3.2.1.21 | *Dictyostelium discoideum* |
|  | U87805 | bgl1 | EC 3.2.1.21 | *Coccidioides posadasii* |
|  | AM922334 | beta-glucosidase | EC 3.2.1.21 | *Rhizomucor miehei* |
|  | DQ114396 | bgl1 | EC 3.2.1.21 | *Thermoascus aurantiacus* |
|  | CS497644 | beta-glucosidase | EC 3.2.1.21 | *Penicillium brasilianum* |
|  | DD463307 | beta-glucosidase | EC 3.2.1.21 | *Aspergillus oryzae* |

TABLE III-continued

| No Nucleotide ID | Gene name | Enzyme class | Species |
|---|---|---|---|
| DD463306 | beta-glucosidase | EC 3.2.1.21 | *Aspergillus oryzae* |
| DD463305 | beta-glucosidase | EC 3.2.1.21 | *Aspergillus oryzae* |
| DQ926702 | beta-glucosidase | EC 3.2.1.21 | *Rhizoctonia solani* |
| AY281378 | beta-glucosidase cel3D | EC 3.2.1.21 | *Hypocrea jecorina/Trichoderma reesei* |
| EU029950 | beta-glucosidase | EC 3.2.1.21 | *Penicillium occitanis* |
| EF648280 | beta-glucosidase | EC 3.2.1.21 | *Chaetomium thermophilum* |
| EF527403 | bgl1 | EC 3.2.1.21 | *Penicillium brasilianum* |
| DQ114397 | bgl1 | EC 3.2.1.21 | *Thermoascus aurantiacus* |
| XM_001398779 | bgl1 | EC 3.2.1.21 | *Aspergillus niger* |
| XM_001274044 | beta-glucosidase | EC 3.2.1.21 | *Aspergillus clavatus* |
| AF121777 | beta-glucosidase | EC 3.2.1.21 | *Aspergillus niger* |
| AJ566365 | beta-glucosidase | EC 3.2.1.21 | *Aspergillus oryzae* |
| AJ132386 | bgl1 | EC 3.2.1.21 | *Aspergillus niger* |
| AF016864 | beta-glucosidase | EC 3.2.1.21 | *Orpinomyces* sp. PC-2 |
| CS435985 | beta-glucosidase | EC 3.2.1.21 | *Hypocrea jecorina* |
| DQ011524 | bgl2 | EC 3.2.1.21 | *Thermoascus aurantiacus* |
| DQ011523 | bgl2 | EC 3.2.1.21 | *Thermoascus aurantiacus* |
| DD329362 | Bgl6 | EC 3.2.1.21 | *Hypocrea jecorina/Trichoderma reesei* |
| DD329363 | Bgl6 | EC 3.2.1.21 | *Hypocrea jecorina*/Trichoderma reesei |
| DQ888228 | bgl | EC 3.2.1.21 | *Chaetomium thermophilum* |
| DQ655704 | bgl | EC 3.2.1.21 | *Aspergillus niger* |
| DQ010948 | bgl | EC 3.2.1.21 | *Pichia anomala*/Candida beverwijkiae |
| DQ010947 | beta-glucosidase | EC 3.2.1.21 | *Hanseniaspora uvarum* |
| DD146974 | Bgl | EC 3.2.1.21 | *Hypocrea jecorina/Trichoderma reesei* |
| DD146973 | Bgl | EC 3.2.1.21 | *Hypocrea jecorina/Trichoderma reesei* |
| DD182179 | Bgl | EC 3.2.1.21 | *Hypocrea jecorina/Trichoderma reesei* |
| DD182178 | Bgl | EC 3.2.1.21 | *Hypocrea jecorina/Trichoderma reesei* |
| DD181296 | Bgl | EC 3.2.1.21 | *Hypocrea jecorina/Trichoderma reesei* |
| DD181295 | Bgl | EC 3.2.1.21 | *Hypocrea jecorina/Trichoderma reesei* |
| CS103208 | beta-glucosidase | EC 3.2.1.21 | *Aspergillus fumigatus* |
| AJ276438 | bgl1A | EC 3.2.1.21 | *Piromyces* sp. E2 |
| AY943971 | bgl1 | EC 3.2.1.21 | *Aspergillus avenaceus* |
| AY688371 | bgl1 | EC 3.2.1.21 | *Phaeosphaeria avenaria* |
| AY683619 | bgl1 | EC 3.2.1.21 | *Phaeosphaeria nodorum* |
| AB081121 | beta-glucosidase | EC 3.2.1.21 | *Phanerochaete chrysosporium* |
| AY445049 | bgla | EC 3.2.1.21 | *Candida albicans* |
| AF500792 | beta-glucosidase | EC 3.2.1.21 | *Piromyces* sp. E2 |
| AY343988 | beta-glucosidase | EC 3.2.1.21 | *Trichoderma viride* |
| AY072918 | beta-glucosidase | EC 3.2.1.21 | *Talaromyces emersonii* |
| BD185278 | beta-glucosidase | EC 3.2.1.21 | *Debaryomyces hansenii/Candida famata* |
| BD178410 | beta-glucosidase | EC 3.2.1.21 | *Debaryomyces hansenii/Candida famata* |
| BD168028 | beta-glucosidase | EC 3.2.1.21 | *Acremonium cellulolyticus* |
| AB003110 | bgl | EC 3.2.1.21 | *Hypocrea jecorina/Trichoderma reesei* |
| AB003109 | bgl4 | EC 3.2.1.21 | *Humicola grisea* var. *thermoidea* |
| AY049946 | BGL5 | EC 3.2.1.21 | *Coccidioides posadasii* |
| AF338243 | BGL3 | EC 3.2.1.21 | *Coccidioides posadasii* |
| AY081764 | beta-glucosidase | EC 3.2.1.21 | *Talaromyces emersonii* |
| AY049947 | BGL6 | EC 3.2.1.21 | *Coccidioides posadasii* |
| AY049945 | BGL4 | EC 3.2.1.21 | *Coccidioides posadasii* |
| AY049944 | BGL3 | EC 3.2.1.21 | *Coccidioides posadasii* |
| AF022893 | BGL2 | EC 3.2.1.21 | *Coccidioides posadasii* |
| AX011537 | beta-glucosidase | EC 3.2.1.21 | *Aspergillus oryzae* |
| AF268911 | beta-glucosidase | EC 3.2.1.21 | *Aspergillus niger* |
| U31091 | beta-glucosidase | EC 3.2.1.21 | *Candida wickerhamii* |
| U13672 | beta-glucosidase | EC 3.2.1.21 | *Candida wickerhamii* |
| AF036873 | beta-glucosidase | EC 3.2.1.21 | *Phanerochaete chrysosporium* |
| AF036872 | beta-glucosidase | EC 3.2.1.21 | *Phanerochaete chrysosporium* |
| X05918 | beta-glucosidase | EC 3.2.1.21 | *Kluyveromyces marxianus* |
| U16259 | beta-glucosidase (bgln) | EC 3.2.1.21 | *Pichia capsulata* |
| M22476 | BGL2 | | *Saccharomycopsis fibuligera* |
| M22475 | BGL1 | | *Saccharomycopsis fibuligera* |
| M27313 | beta-glucosidase | | *Schizophyllum commune* |

TABLE IV

| No. | Source | Gene | Accession No. |
|---|---|---|---|
| 1 | *Gibberella zeae* | triacylglycerol lipase FGL5 | EU402385 |
| 2 | *Schizosaccharomyces pombe* | 972h-triacylglycerol lipase (SPCC1450.16c) | NM_001023305 |
| 3 | *Schizosaccharomyces pombe* | 972h-esterase/lipase (SPAC8F11.08c) | NM_001019384 |
| 4 | *Schizosaccharomyces pombe* | 972h-triacylglycerol lipase (SPAC1A6.05c) | NM_001018593 |

TABLE IV-continued

| No. | Source | Gene | Accession No. |
|---|---|---|---|
| 5 | Hypocrea lixii | lip1 gene for lipase 1 | AM180877 |
| 6 | Thermomyces lanuginosus | lipase (LGY) gene | EU022703 |
| 7 | Aspergillus niger strain F044 | triacylglycerol lipase precursor | DQ647700 |
| 8 | Antrodia cinnamomea | lipase | EF088667 |
| 9 | Aspergillus oryzae | tglA gene for triacylglycerol lipase | AB039325 |
| 10 | Gibberella zeae | triacylglycerol lipase FGL4 | EU191903 |
| 11 | Gibberella zeae | triacylglycerol lipase FGL2 | EU191902 |
| 12 | Gibberella zeae | triacylglycerol lipase (fgl3) | EU139432 |
| 13 | Aspergillus tamarii isolate FS132 | lipase | EU131679 |
| 14 | Aureobasidium pullulans strain HN2.3 | extracellular lipase gene | EU117184 |
| 15 | Rhizopus microsporus var. chinensis | lipase | EF405962 |
| 16 | Fusarium oxysporum | lipase (lip1) | EF613329 |
| 17 | Aspergillus tamarii isolate FS132 | lipase | EF198417 |
| 18 | Neosartorya fischeri NRRL 181 | Secretory lipase (NFIA_072820) | XM_001259263 |
| 19 | Neosartorya fischeri NRRL 181 | Secretory lipase (NFIA_047420) | XM_001257303 |
| 20 | Nectria haematococca | NhL1 gene for extracellular lipase | AJ271094 |
| 21 | Aspergillus terreus NIH2624 | lipase precursor (ATEG_09822) | XM_001218443 |
| 22 | Galactomyces geotrichum | lipase | DQ841229 |
| 23 | Yarrowia lipolytica | lipase 2 | DQ831123 |
| 24 | Magnaporthe grisea | vacuolar triacylglycerol lipase (VTL1) | DQ787100 |
| 25 | Magnaporthe grisea | triacylglycerol lipase (TGL3-2) | DQ787099 |
| 26 | Magnaporthe grisea | triacylglycerol lipase (TGL3-1) | DQ787098 |
| 27 | Magnaporthe grisea | triacylglycerol lipase (TGL2) | DQ787097 |
| 28 | Magnaporthe grisea | triacylglycerol lipase (TGL1-2) | DQ787096 |
| 29 | Magnaporthe grisea | triacylglycerol lipase (TGL1-1) | DQ787095 |
| 30 | Magnaporthe grisea | hormone-sensitive lipase (HDL2) | DQ787092 |
| 31 | Magnaporthe grisea | hormone-sensitive lipase (HDL1) | DQ787091 |
| 32 | Penicillium expansum | triacylglycerol lipase | DQ677520 |
| 33 | Aspergillus niger | triacylglycerol lipase B (lipB) | DQ680031 |
| 34 | Aspergillus niger | triacylglycerol lipase A (lipA) | DQ680030 |
| 35 | Yarrowia lipolytica | lip2 | AJ012632 |
| 36 | Galactomyces geotrichum | triacylglycerol lipase | X81656 |
| 37 | Candida antarctica | lipase B | Z30645 |
| 38 | Candida cylindracea | LIP1 to LIP5 gene for lipase | X64703 to X64708 |
| 39 | Yarrowia lipolytica | LIPY8p (LIPY8) gene | DQ200800 |
| 40 | Yarrowia lipolytica | LIPY7p (LIPY7) gene | DQ200799 |
| 41 | Rhizopus niveus | prepro thermostable lipase | E12853 |
| 42 | Galactomyces geotrichum | lipase | E02497 |
| 43 | Rhizomucor miehei | lipase | A02536 |
| 44 | | | |
| 45 | Fusarium heterosporum | lipase | S77816 |
| 46 | Candida albicans SC5314 | triglyceride lipase (CaO19_10561) | XM_716177 |
| 47 | Candida albicans SC5314 | triglyceride lipase (CaO19_3043) | XM_716448 |
| 48 | Rhizopus stolonifer | lipase lipRs | DQ139862 |
| 49 | Candida albicans | secretory lipase 3 (LIP3) gene to lipase 10 (LIP10) | AF191316 to AF191323 |
| 50 | Candida albicans | secretory lipase 1 (LIP1) | AF188894 |
| 51 | Candida albicans | secretory lipase (LIP2) gene | AF189152 |
| 52 | Emericella nidulans | triacylglycerol lipase (lipA) gene | AF424740 |
| 53 | Gibberella zeae | extracellular lipase (FGL1) | AY292529 |
| 54 | Kurtzmanomyces sp. I-11 | lipase | AB073866 |
| 55 | Candida deformans | lip1 gene to lip 3 for triacylglycerol lipase | AJ428393 to AJ428395 |
| 56 | Botryotinia fuckeliana | lipase (lip1) | AY738714 |
| 57 | Penicillium allii | lipase (lipPA) | AY303124 |
| 58 | Aspergillus flavus | lipase | AF404489 |
| 59 | Aspergillus parasiticus | lipase | AF404488 |
| 60 | Yarrowia lipolytica | LIP4 gene for lipase | AJ549517 |
| 61 | Candida parapsilosis | lip1 gene for lipase 1 and lip2 gene for lipase 2 | AJ320260 |
| 62 | Penicillium expansum | triacylglycerol lipase precursor | AF288685 |
| 63 | Penicillium cyclopium | alkaline lipase | AF274320 |
| 64 | Pseudomonas sp. | lip35 lipase gene | EU414288 |
| 65 | Bacillus sp. NK13 | lipase gene | EU381317 |
| 66 | Uncultured bacterium | lipase/esterase gene | EF213583 to EF213587 |
| 67 | Shewanella piezotolerans | WP3 lipase gene | EU352804 |
| 68 | Bacillus sp. Tosh | lipase (lipA) gene | AY095262 |
| 69 | Bacillus subtilis strain FS321 | lipase | EF567418 |
| 70 | Pseudomonas fluorescens strain JCM5963 | lipase | EU310372 |
| 71 | Pseudomonas fluorescens | triacylglycerol lipase | D11455 |
| 72 | Burkholderia cepacia | alkaline lipase | EU280313 |
| 73 | Burkholderia sp. HY-10 | lipase (lipA) and lipase foldase (lifA) genes | EF562602 |

TABLE IV-continued

| No. | Source | Gene | Accession No. |
|---|---|---|---|
| 74 | *Pseudomonas aeruginosa* | lip9, lif9 genes for LST-03 lipase, lipase-specific foldase | AB290342 |
| 75 | *Pseudomonas fluorescens* | gene for lipase | AB009011 |
| 76 | *Streptomyces fradiae* | clone k11 lipase gene | EF429087 |
| 77 | *Geobacillus zalihae* strain T1 | thermostable lipase gene | AY260764 |
| 78 | *Pseudomonas* sp. MIS38 | gene for lipase | AB025596 |
| 79 | *Uncultured bacterium* | cold-active lipase (lipCE) gene | DQ925372 |
| 80 | *Burkholderia cepacia* | lipase (lipA) and lipase chaperone (lipB) genes | DQ078752 |
| 81 | *Psychrobacter* sp. | 2-17 lipase gene | EF599123 |
| 82 | *Bacillus subtilis* strain Fs32b | lipase gene | EF541144 |
| 83 | *Bacillus subtilis* strain FS14-3a | lipase gene | EF538417 |
| 84 | *Aeromonas hydrophila* strain J-1 | extracellular lipase gene | EF522105 |
| 85 | *Acinetobacter* sp. MBDD-4 | lipase gene | DQ906143 |
| 86 | *Photorhabdus luminescens* subsp. *akhurstii* strain 1007-2 | lipase 1 (lip1) gene | EF213027 |
| 87 | *Uncultured bacterium* clone h1Lip1 | lipase gene | DQ118648 |
| 88 | *Geobacillus thermoleovorans* | lipase precursor (lipA) gene | EF123044 |
| 89 | *Bacillus pumilus* strain F3 | lipase precursor | EF093106 |
| 90 | *Pseudomonas fluorescens* lipase (lipB68) gene | lipase (lipB68) gene | AY694785 |
| 91 | *Geobacillus stearothermophilus* strain ARM1 | thermostable lipase precursor gene | EF042975 |
| 92 | *Serratia marcescens* strain ECU1010 | extracellular lipase (lipA) gene | DQ884880 |
| 93 | *Bacillus subtilis* | lipase gene | DQ250714 |
| 94 | *Pseudomonas aeruginosa* | gene for lipase modulator protein | D50588 |
| 95 | *Pseudomonas aeruginosa* | gene for lipase | D50587 |
| 96 | *Uncultured bacterium* clone pUE5 | esterase/lipase (estE5) gene | DQ842023 |
| 97 | *Serratia marcescens* strain ES-2 | lipase (esf) gene | DQ841349 |
| 98 | *Pseudomonas fluorescens* strain 26-2 | lipase class 3 gene | DQ789596 |
| 99 | *Stenotrophomonas maltophilia* strain 0450 | lipase gene | DQ647508 |
| 100 | *Listonella anguillarum* | Plp (plp), Vah1 (vah1), LlpA (llpA), and LlpB (llpB) genes | DQ008059 |
| 101 | *Geobacillus* sp. | SF1 lipase gene | DQ009618 |
| 102 | *Uncultured Pseudomonas* sp. | lipase (lipJ03) gene | AY700013 |
| 103 | *Photobacterium* sp. M37 | lipase gene | AY527197 |
| 104 | *Pseudomonas fluorescens* | lipase (lip) gene | DQ305493 |
| 105 | *Pseudomonas aeruginosa* | lipase (lipB) gene | DQ348076 |
| 106 | *Bacillus pumilus* mutant | lipase precursor | DQ345448 |
| 107 | *Bacillus pumilus* strain YZ02 | lipase gene | DQ339137 |
| 108 | *Geobacillus thermoleovorans* YN | thermostable lipase (lipA) gene | DQ298518 |
| 109 | *Pseudomonas* sp. CL-61 | lipase (lipP) gene | DQ309423 |
| 110 | *Burkholderia* sp. 99-2-1 | lipase (lipA) gene | AY772174 |
| 111 | *Burkholderia* sp. MC16-3 | lipase (lipA) gene | AY772173 |
| 112 | *Pseudomonas fluorescens* | lipase (lipB52) gene | AY623009 |
| 113 | *Geobacillus stearothermophilus* | lipase gene | AY786185 |
| 114 | *Burkholderia multivorans* strain Uwc 10 | LifB (lifB) gene | DQ103702 |
| 115 | *Burkholderia multivorans* strain Uwc 10 | LipA (lipA) gene | DQ103701 |
| 116 | *Bacillus pumilus* | lipase precursor gene | AY494714 |
| 117 | *Bacillus* sp. TP10A.1 | triacylglycerol lipase (lip1) gene | AF141874 |
| 118 | *Staphylococcus warneri* | gehWC gene for lipase | AB189474 |
| 119 | *Staphylococcus warneri* | lipWY gene for lipase | AB189473 |
| 120 | *Bacillus* sp. L2 | thermostable lipase gene | AY855077 |
| 121 | *Bacillus megaterium* | lipase/esterase gene | AF514856 |
| 122 | *Pseudomonas aeruginosa* | lip8 gene for lipase | AB126049 |
| 123 | *Bacillus* sp. 42 | thermostable organic solvent tolerant lipase gene | AY787835 |
| 124 | *Pseudomonas fluorescens* | lipase (lipB41) gene | AY721617 |
| 125 | *Burkholderia cepacia* | triacylglycerol lipase (LipA) and lipase chaperone (LipB) genes | AY682925 |
| 126 | *Pseudomonas aeruginosa* | triacylglycerol lipase (LipA) and lipase chaperone (LipB) genes | AY682924 |
| 127 | *Vibrio vulnificus* | lipase and lipase activator protein genes | AF436892 |
| 128 | *Uncultured bacterium* plasmid pAH114 | lipase (lipA) gene | AF223645 |
| 129 | *Thermoanaerobacter tengcongensis* | lipase (lip1) gene | AY268957 |
| 130 | *Pseudomonas aeruginosa* | lip3 gene for lipase | AB125368 |
| 131 | *Staphylococcus epidermidis* | lipase precursor (gehD) gene | AF090142 |
| 132 | *Pseudomonas fluorescens* clone: pLP101-2741 | lipA gene for lipase | AB109036 |

TABLE IV-continued

| No. | Source | Gene | Accession No. |
|---|---|---|---|
| 133 | Pseudomonas fluorescens clone: pLPM101 | lipA gene for lipase | AB109035 |
| 134 | Pseudomonas fluorescens clone: pLPD101 | lipA gene for lipase | AB109034 |
| 135 | Pseudomonas fluorescens clone: pLP101 | lipA gene for lipase | AB109033 |
| 136 | Micrococcus sp. HL-2003 | lipase gene | AY268069 |
| 137 | Pseudomonas sp. JZ-2003 | lipase gene | AY342316 |
| 138 | Vibrio harveyi | vest gene | AF521299 |
| 139 | Pseudomonas fluorescens | lipase gene | AY304500 |
| 140 | Bacillus sphaericus strain 205y | lipase gene | AF453713 |
| 141 | Bacillus subtilis | lipase (lipE) gene | AY261530 |
| 142 | Synthetic construct | triacylglycerol lipase gene | AY238516 |
| 143 | Serratia marcescens | lipA gene for lipase | D13253 |
| 144 | Geobacillus thermoleovorans IHI-91 | thermophilic lipase gene | AY149997 |
| 145 | Streptomyces rimosus | GDSL-lipase gene | AF394224 |
| 146 | Pseudomonas luteola | triacylglycerol lipase precursor gene | AF050153 |
| 147 | Geobacillus thermoleovorans | thermostable lipase (lipA) | AY095260 |
| 148 | Mycoplasma hyopneumoniae | triacylglycerol lipase (lip) gene | AY090779 |
| 149 | Staphylococcus aureus | lipase gene | AY028918 |
| 150 | Bacillus sp. B26 | lipase gene | AF232707 |
| 151 | Pseudomonas aeruginosa | triacylglycerol acylhydrolase (lipA) | AF237723 |
| 156 | Bacillus stearothermophilus | lipase gene | AF429311 |
| 157 | Bacillus stearothermophilus | lipase gene | AF237623 |
| 158 | Bacillus thermoleovorans | lipase (ARA) gene | AF134840 |
| 159 | Bacillus stearothermophilus | lipase gene | U78785 |
| 160 | Pseudomonas fluorescens | lipase (lipB) gene | AF307943 |
| 161 | Pseudomonas sp. KB700A | KB-lip gene for lipase | AB063391 |
| 162 | Moritella marina | super-integron triacylglycerol acyl hydrolase (lip) gene | AF324946 |
| 163 | Staphylococcus xylosus | lipase precursor GehM (gehM) gene | AF208229 |
| 164 | Staphylococcus warneri | lipase precursor (gehA) gene | AF208033 |
| 165 | Pseudomonas sp. UB48 | lipase (lipUB48) gene | AF202538 |
| 166 | Psychrobacter sp. St1 | lipase (lip) gene | AF260707 |
| 167 | Pseudomonas fluorescens | polyurethanase lipase A (pulA) gene | AF144089 |
| 168 | Staphylococcus haemolyticus | lipase gene | AF096928 |
| 169 | Pseudomonas fluorescens | genes for ABC exporter operon | AB015053 |
| 170 | Pseudomonas aeruginosa | lipase (lipC) gene | U75975 |
| 171 | Streptomyces coelicolor | lipase (lipA), and LipR activator (lipR) genes | AF009336 |
| 172 | Petroleum-degrading bacterium HD-1 | gene for esterase HDE | AB029896 |
| 173 | Pseudomonas fragi | lipase precursor gene | M14604 |
| 174 | Acinetobacter calcoaceticus | lipase (lipA) and lipase chaperone (lipB) genes | AF047691 |
| 175 | Streptomyces albus | lipase precursor (lip) and LipR genes | U03114 |
| 176 | Staphylococcus epidermidis | lipase precursor (geh1) gene | AF053006 |
| 177 | Pseudomonas sp. B11-1 | lipase (lipP) gene | AF034088 |
| 178 | Pseudomonas fluorescens | lipase (lipA) gene | AF031226 |
| 179 | Pseudomonas aeruginosa | gene for lipase | AB008452 |
| 180 | Pseudomonas wisconsinensis | extracellular lipase (lpwA) and lipase helper protein (lpwB) genes | U88907 |
| 181 | Aeromonas hydrophila | extracellular lipase (lip) gene | U63543 |
| 182 | Streptomyces sp. | triacylglycerol acylhydrolase (lipA) and lipA transcriptional activator (lipR) genes | M86351 |
| 183 | Proteus vulgaris | alkaline lipase gene | U33845 |
| 184 | Moraxella sp. | lip3 gene for lipase 3 | X53869 |
| 185 | Serratia marcescens SM6 | extracellular lipase (lipA) | U11258 |
| 186 | Staphylococcus aureus | geh gene encoding lipase (glycerol ester hydrolase) | M12715 |
| 187 | Pseudomonas fluorescens | lipase gene | M86350 |
| 188 | Bacillus subtilis | lipase (lipA) | M74010 |
| 189 | Staphylococcus epidermidis | lipase (gehC) gene | M95577 |

TABLE V

| Nucleotide Id | Gene | Enzyme class | Species |
|---|---|---|---|
| EU367969 | alpha-amylase | 3.2.1.1 | Bacillus amyloliquefaciens |
| BD249244 | Alpha-amylase | | Bacillus amyloliquefaciens |
| DD238310 | Alpha-amylase | | Bacillus amyloliquefaciens |
| BD460864 | Alpha-amylase | | Bacillus amyloliquefaciens |
| V00092 | Alpha-amylase | | Bacillus amyloliquefaciens |
| M18424 | Alpha-amylase | | Bacillus amyloliquefaciens |

TABLE V-continued

| Nucleotide Id | Gene | Enzyme class | Species |
|---|---|---|---|
| J01542 | Alpha-amylase | | *Bacillus amyloliquefaciens* |
| EU184860 | amyE | | *Bacillus subtilis* |
| AM409180 | amy | | *Bacillus subtilis* |
| E01643 | alpha-amylase | | *Bacillus subtilis* |
| X07796 | alpha-amylase | | *Bacillus subtilis* 2633 |
| AY594351 | alpha-amylase | | *Bacillus subtilis* strain HA401 |
| AY376455 | amy | | *Bacillus subtilis* |
| V00101 | amyE | | *Bacillus subtilis* |
| AF115340 | maltogenic amylase | EC 3.2.1.133 | *Bacillus subtilis* |
| AF116581 | amy | EC 3.2.1.1 | *Bacillus subtilis* |
| K00563 | alpha-amylase | | *Bacillus subtilis* |
| M79444 | alpha-amylase | | *Bacillus subtilis* |
| DQ852663 | alpha-amylase | | *Geobacillus stearothermophilus* |
| E01181 | alpha-amylase | | *Geobacillus stearothermophilus* |
| E01180 | alpha-amylase | | *Geobacillus stearothermophilus* |
| E01157 | alpha-amylase | | *Geobacillus (Bacillus) stearothermophilus* |
| Y17557 | maltohexaose-producing alpha-amylase | 3.2.1.133 | *Bacillus stearothermophilus* |
| AF032864 | ami | EC 3.2.1.1 | *Bacillus stearothermophilus* |
| U50744 | maltogenic amylase BSMA | 3.2.1.133 | *Bacillus stearothermophilus* |
| M13255 | amyS | EC 3.2.1.1 | *B. stearothermophilus* |
| M11450 | alpha-amylase | | *B. stearothermophilus* |
| M57457 | alpha amylase | | *B. stearothermophilus* |
| X59476 | alpha-amylase | | *B. stearothermophilus* |
| X02769 | alpha-amylase | | *Bacillus stearothermophilus* |
| X67133 | BLMA | | *Bacillus licheniformis* |
| BD249243 | Alpha-amylase | | *Bacillus licheniformis* |
| DQ517496 | alpha-amylase | | *Bacillus licheniformis* strain RH 101 |
| DD238309 | alpha-amylase | | *Bacillus licheniformis* |
| E12201 | ACID-RESISTANT/THERMOSTABLE ALPHA-AMYLASE GENE | | *Bacillus licheniformis* |
| BD460878 | Alpha-amylase | | *Bacillus licheniformis* |
| DQ407266 | amyl thermotolerant | | *Bacillus licheniformis* |
| AF438149 | amy hyperthermostable | | *Bacillus licheniformis* |
| A27772 | amyl thermotolerant | EC 3.2.1.1 | *Bacillus licheniformis* |
| A17930 | Alpha amylase | | *Bacillus licheniformis* |
| M13256 | amyS | | *B. licheniformis* |
| M38570 | alpha-amylase | | *B. licheniformis* |
| AF442961 | alpha-amylase amyA | | *Halothermothrix orenii* |
| AY220756 | alpha amylase | | *Xanthomonas campestris* |
| AY165038 | alpha-amylase | | *Xanthomonas campestris* pv. *campestris* |
| AF482991 | alpha-amylase | | *Xanthomonas campestris* pv. *campestris* str. 8004 |
| M85252 | amy | | *Xanthomonas campestris* |
| AY240946 | amyB | | *Bifidobacterium adolescentis* |
| EU352611 | alpha-amylase | | *Streptomyces lividans* |
| EU414483 | amylase-like gene | | *Microbispora* sp. V2 |
| EU352611 | alpha-amylase (amyA) | | *Streptomyces lividans* |
| D13178 | alpha-amylase | | *Thermoactinomyces vulgaris* |
| EU159580 | amylase gene | | *Bacillus* sp. YX |
| D90112 | raw-starch-digesting amylase | | *Bacillus* sp. B1018 |
| AB274918 | amyI, thermostable amylase | | *Bacillus halodurans* |
| EU029997 | Alpha-amylase | | *Bacillus* sp. WHO |
| AM409179 | maltogenic amylase | 3.2.1.133 | *Bacillus* sp. US149 |
| AB178478 | Alpha-amylase | | *Bacillus* sp. KR-8104 |
| AB029554 | alpha-amylase, glucoamylase | 3.2.1.1, 3.2.1.3 | *Thermoactinomyces vulgaris* |
| DQ341118 | alpha amylase | 3.2.1.1 | *Bifidobacterium thermophilum* strain JCM7027 |
| D12818 | glucoamylase | 3.2.1.3 | *Clostridium* sp. |
| AB115912 | glucoamylase | | *Clostridium thermoamylolyticum* |
| AB047926 | glucoamylase | | *Thermoactinomyces vulgaris* R-47 |
| AF071548 | glucoamylase | | *Thermoanaerobacterium thermosaccharolyticum* |
| DQ104609 | glucoamylase (gla) | | *Chaetomium thermophilum* |
| AB083161 | glucoamylase | | *Aspergillus awamori* GA I |
| EF545003 | glucoamylase (gla) | | *Thermomyces lanuginosus* |
| XM_743288 | glucan 1,4-alpha-glucosidase | | *Aspergillus fumigatus* |
| DQ268532 | glucoamylase A | | *Rhizopus oryzae* |
| DQ219822 | glucoamylase b | | *Rhizopus oryzae* |
| D10460 | glucoamylase | | *Aspergillus shirousami* GLA |

TABLE V-continued

| Nucleotide Id | Gene | Enzyme class | Species |
|---|---|---|---|
| AJ304803 | glucoamylase | | Talaromyces emersonii |
| Z46901 | glucoamylase | | Arxula adeninivorans |
| XM_001215158 | glucoamylase | | Aspergillus terreus NIH2624 |
| AY948384 | glucoamylase | | Thermomyces lanuginosus |
| X00712 | Glucoamylase | 3.2.1.3 | A. niger |
| AB239766 | glucoamylase | | Fomitopsis palustris |
| E15692 | Glucoamylase | | Aspergillus oryzae |
| E01247 | glucoamylase | | Rhizopus oryzae |
| E01175 | glucoamylase | | Saccharomycopsis fibuligera |
| E00315 | glucoamylase | | Aspergillus awamori |
| DQ211971 | gluB | | Aspergillus oryzae |
| AJ890458 | gla66 | | Trichoderma harzianum |
| X58117 | glucoamylase | | Saccharomycopsis fibuligera |
| X67708 | 1,4-alpha-D-glucan glucohydrolase. | | Amorphotheca resinae |
| X00548 | glucoamylase G1 cDNA | | Aspergillus niger |
| AJ311587 | glucoamylase (glu 0111 gene) | | Saccharomycopsis fibuligera |
| AY652617 | gluA-A | | Aspergillus niger strain VanTieghem |
| AY642120 | gluA-G | | Aspergillus ficuum |
| AB091510 | glucoamylase | | Penicillium chrysogenum |
| AY250996 | glucoamylase | | Aspergillus niger |
| AB007825 | glucoamylase | | Aspergillus oryzae |
| BD087401 | Thermostable glucoamylase | | Talaromyces emersonii |
| BD087377 | Thermostable glucoamylase | | Aspergillus niger |
| D00427 | glucoamylase I | | Aspergillus kawachii |
| AF082188 | GCA1 | | Candida albicans |
| AF220541 | glucoamylase | | Lentinula edodes |
| D45356 | aglA | | Aspergillus niger |
| D00049 | glucoamylase | | Rhizopus oryzae |
| D49448 | glucoamylase G2 | | Corticium rolfsii |
| U59303 | glucoamylase | | Aspergillus awamori |
| X13857 | Glucan-1,4-alpha-glucosidase | | Saccharomyces cerevisiae |
| L15383 | glucoamylase | | Aspergillus terreus |
| M60207 | glucoamylase (GAM1) | | Debaryomyces occidentalis |
| M89475 | gla1 | | Humicola grisea thermoidea |
| M90490 | 1,4-alpha-D-glucanglucohydrolase | | Saccharomyces diastaticus |
| D10461 | AMY | 3.2.1.1 | Aspergillus shirousami |
| DQ663472 | alpha-amylase | | Fusicoccum sp. BCC4124 |
| EU014874 | AMY1 | | Cryptococcus flavus |
| AB083162 | amyI III | | Aspergillus awamori |
| AB083160 | amyI III | | Aspergillus awamori |
| AB083159 | amyI I | | Aspergillus awamori |
| XM_001544485 | alpha-amylase A | | Ajellomyces capsulatus |
| EF143986 | alpha-amylase | | Phanerochaete chrysosporium |
| EF682066 | alpha-amylase | | Paracoccidioides brasiliensis |
| XM_750586 | alpha-amylase | 3.2.1.1 | Aspergillus fumigatus Af293 |
| XM_744365 | alpha-amylase AmyA | | Aspergillus fumigatus Af293 |
| XM_742412 | Maltase | 3.2.1.3 | Aspergillus fumigatus Af293 |
| XM_001395712 | amyA/amyB | 3.2.1.1 | Aspergillus niger |
| XM_001394298 | acid alpha-amylase | | Aspergillus nomius strain PT4 |
| DQ467933 | amyI | | Aspergillus nomius strain KS13 |
| DQ467931 | amyI | | Aspergillus nomius strain TK32 |
| DQ467931 | amyI | | Aspergillus nomius |
| DQ467923 | amyI | | Aspergillus pseudotamarii |
| DQ467918 | alpha amylase | | Aspergillus parasiticus |
| DQ467917 | amyI | | Aspergillus sp. BN8 |
| DQ467916 | amyI | | Aspergillus flavus strain UR3 |
| DQ467908 | amyI | | Aspergillus flavus strain AF70 |
| XM_001275450 | alpha-amylase | | Aspergillus clavatus NRRL |
| XM_001275449 | alpha-glucosidase/alpha-amylase | | Aspergillus clavatus |
| XM_001265627 | alpha-amylase | | Neosartorya fischeri NRR |
| | maltase | 3.2.1.3 | Neosartorya fischeri |
| DQ526426 | amy1 | 3.2.1.1 | Ophiostoma floccosum |
| EF067865 | AMY1 | | Ajellomyces capsulatus |
| X12727 | alpha-amylase | | Aspergillus oryzae |
| AY155463 | alpha-amylase | | Lipomyces starkeyi |
| XM_567873 | Alpha-amylase | | Cryptococcus neoformans var. neoformans |
| BD312604 | Alpha-amylase | | Aspergillus oryzae |
| XM_714334 | maltase | 3.2.1.3 | Candida albicans |
| X16040 | amy1 | 3.2.1.1 | Schwanniomyces occidentalis |
| AB024615 | amyR | | Emericella nidulans |

TABLE V-continued

| Nucleotide Id | Gene | Enzyme class | Species |
|---|---|---|---|
| U30376 | alpha-amylase | | *Lipomyces kononenkoae* subsp. *spencermartinsiae* |
| AB008370 | acid-stable alpha-amylase | | *Aspergillus kawachii* |
| K02465 | glucoamylase | 3.2.1.1 | *A. awamori* |
| XM_001276751 | Maltogenic alpha-amylase | 3.2.1.133 | *Aspergillus clavatus* NRRL 1 |
| XM_001273477 | Maltogenic alpha-amylase | | *Aspergillus clavatus* NRRL 1 |
| AB044389 | Maltogenic alpha-amylase | | *Aspergillus oryzae* |
| EU368579 | Maltogenic alpha-amylase | | *Bacillus* sp. ZW2531-1 |
| M36539 | Maltogenic alpha-amylase | | *Geobacillus stearothermophilus* |
| AM409179 | Maltogenic alpha-amylase | | *Bacillus* sp. US149 |
| Z22520 | maltogenic amylase | | *B. acidopullulyticus* |
| X67133 | maltogenic amylase | | *Bacillus licheniformis* |
| AY986797 | maltogenic amylase | | *Bacillus* sp. WPD616 |
| U50744 | maltogenic amylase | | *Bacillus stearothermophilus* |
| M36539 | maltogenic amylase | | *B. stearothermophilus* |
| AF115340 | maltogenic amylase | 3.2.1.133 | *Bacillus subtilis* Bbma |
| AF060204 | maltogenic amylase | | *Thermus* sp. IM6501 |
| Z22520 | maltogenic amylase | | *Bacillus acidopullulyticus* |
| AAF23874 | maltogenic amylase | | *Bacillus subtilis* SUH4-2 |
| AY684812 | maltogenic amylase | | *Bacillus thermoalkalophilus* ET2 |
| U50744 | maltogenic amylase | | *Geobacillus stearothermophilus* ET1 |
| | LACCASE | 1.10.3.2 | |
| EU375894 | laccase | 1.10.3.2 | *Hypsizygus marmoreus* |
| AM773999 | laccase | | *Pleurotus eryngii* |
| EF175934 | laccase (lcc15) | | *Coprinopsis cinerea* strain FA2222 |
| EU031524 | laccase | | *Pleurotus eryngii* var. *ferulae* |
| EU031520 | laccase | | *Pleurotus eryngii* var. *ferulae* |
| EF050079 | laccase 2 | | *Sclerotinia minor* |
| AM176898 | lac gene | | *Crinipellis* sp. RCK-1 |
| EF624350 | laccase | | *Pholiota nameko* strain Ph-5(3) |
| AB212734 | laccase4 | | *Trametes versicolor* |
| Y18012 | laccase | | *Trametes versicolor* |
| D84235 | laccase | | *Coriolus versicolor* |
| AB200322 | laccase | | *Thermus thermophilus* |
| AY228142 | alkaline laccase (lbh1) | | *Bacillus halodurans* |

TABLE VI

EC 3.1.1.74

| No. | Source | Gene | Accession No. |
|---|---|---|---|
| 1 | *Colletotrichum gloeosporioides* | cutinase | M21443 |
| 2 | *Fusarium oxysporum* | cutinase (lip1) gene | EF613272 |
| 3 | *Neosartorya fischeri* NRRL 181 | cutinase family protein (NFIA_102190) | XM_001266631 |
| 4 | *Neosartorya fischeri* NRRL 181 | cutinase family protein (NFIA_089600) | XM_001260899 |
| 5 | *Pyrenopeziza brassicae* | cutinase gene | AJ009953 |
| 6 | *Botryotinia fuckeliana* | cutA gene | Z69264 |
| 7 | *Ascochyta rabiei* | cut gene for cutinase | X65628 |
| 8 | *Aspergillus terreus* NIH2624 | cutinase precursor (ATEG_04791) | XM_001213969 |
| 9 | *Aspergillus terreus* NIH2624 | acetylxylan esterase precursor (ATEG_04709) | XM_001213887 |
| 10 | *Aspergillus terreus* NIH2624 | acetylxylan esterase precursor (ATEG_04056) | XM_001213234 |
| 11 | *Aspergillus terreus* NIH2624 | cutinase precursor (ATEG_03640) | XM_001212818 |
| 12 | *Aspergillus terreus* NIH2624 | cutinase precursor (ATEG_02133) | XM_001211311 |
| 13 | *Emericella nidulans* | cutinase (AN7541-2) | DQ490511 |
| 14 | *Emericella nidulans* | cutinase (AN7180-2) | DQ490506 |
| 15 | *Monilinia fructicola* | cutinase (cut1) gene | DQ173196 |
| 16 | *Nectria haematococca* | cutinase 3 (cut3) gene | AF417005 |
| 17 | *Nectria haematococca* | cutinase 2 (cut2) | AF417004 |
| 18 | *Nectria ipomoeae* | cutinase (cutA) | U63335 |
| 19 | *Phytophthora infestans* clone PH026H6 | cutinase | AY961421 |
| 20 | *Phytophthora infestans* | cutinase (Cut1) | AY954247 |
| 21 | *Phytophthora brassicae* | cutinase (CutB) | AY244553 |

TABLE VI-continued

EC 3.1.1.74

| No. | Source | Gene | Accession No. |
|---|---|---|---|
| 22 | Phytophthora brassicae | cutinase (CutA) | AY244552 |
| 23 | Phytophthora capsici | cutinase | X89452 |
| 24 | Monilinia fructicola | cutinase (cut1) | AF305598 |
| 25 | Blumeria graminis | cutinase (cut1) | AF326784 |
| 26 | Glomerella cingulata | cutinase | AF444194 |
| 27 | Mycobacterium avium | serine esterase cutinase | AF139058 |
| 28 | Aspergillus oryzae | CutL gene for cutinase | D38311 |
| 29 | Fusarium solani | cutinase | M29759 |
| 30 | Fusarium solani pisi | cutinase | K02640 |
| 31 | Colletotrichum capsici | cutinase | M18033 |
| 32 | Alternaria brassicicola | cutinase (cutab1) | U03393 |

TABLE VII

| No. | Source | Gene | Accession No |
|---|---|---|---|
| 1 | Colletotrichum gloeosporioides | pectate lyase (pelA) partial | L41646 |
| 2 | Colletotrichum gloeosporioides | pectin lyase (pnlA) | L22857 |
| 3 | Bacillus subtilis | pectin lyase | D83791 |
| 4 | Aspergillus fumigatus | pectin lyase B | XM_743914 |
| 5 | Aspergillus fumigatus | pectin lyase | XM_748531 |
| 6 | Aspergillus niger | pectin lyase pelD | XM_001402486 |
| 7 | Aspergillus niger | pectin lyase pelA | XM_001401024 |
| 8 | Aspergillus niger | pectin lyase pelB | XM_001389889 |
| 9 | Aspergillus oryzae | pectin lyase 1 precursor (pel1) partial | EF452419 |
| 10 | Pseudoalteromonas haloplanktis | pectin methylesterase/pectate lyase (pelA) | AF278706 |
| 11 | Penicillium griseoroseum | pectin lyase (plg2) | AF502280 |
| 12 | Penicillium griseoroseum | pectin lyase (plg1) | AF502279 |
| 13 | Aspergillus niger | rglA gene for rhamnogalacturonan lyase A | AJ489944 |
| 14 | Aspergillus niger | pelF gene for pectine lyase F, | AJ489943 |
| 15 | Aspergillus niger | plyA gene for pectate lyase A | AJ276331 |
| 16 | Mycosphaerella pinodes | pelA | X87580 |
| 17 | | Artificial pelC gene | A12250 |
| 18 | | Artificial pelB gene | A12248 |
| 19 | Aspergillus niger | pelB gene for pectin lyase B | X65552 |
| 20 | Aspergillus niger | pelA gene for pectin lyase | X60724 |
| 21 | Emericella nidulans | pectin lyase | DQ490480 |
| 22 | Emericella nidulans | pectin lyase | DQ490478 |
| 23 | Erwinia chrysanthemi | kdgF, kduI, kduD, pelW genes | X62073 |
| 24 | Erwinia sp. BTC105 | pectate lyase | DQ486987 |
| 25 | Erwinia chrysanthemi | pelI gene | Y13340 |
| 26 | Erwinia carotovora | pel1, pel2 and pel3 genes | X81847 |
| 27 | Bacillus sp. | pelA gene | AJ237980 |
| 28 | Erwinia chrysanthemi | pelC | AJ132325 |
| 29 | Erwinia chrysanthemi | pelD | AJ132101 |
| 30 | Bacillus halodurans strain ATCC 27557 | pectate lyase | AY836613 |
| 31 | Uncultured bacterium clone BD12273 | pectate lyase gene | AY836652 |
| 32 | Uncultured bacterium clone BD9113 | Pectate lyase | AY836651 |
| 33 | Uncultured bacterium clone BD9318 | Pectate lyase | AY836650 |
| 34 | Uncultured bacterium clone BD8802 | Pectate lyase | AY836649 |
| 35 | Uncultured bacterium clone BD9207 | Pectate lyase | AY836648 |
| 36 | Uncultured bacterium clone BD9208 | Pectate lyase | AY836647 |
| 37 | Uncultured bacterium clone BD9209 | Pectate lyase | AY836646 |
| 38 | Uncultured bacterium clone BD7597 | Pectate lyase | AY836645 |
| 39 | Uncultured bacterium clone BD9561 | Pectate lyase | AY836644 |

TABLE VII-continued

| No. | Source | Gene | Accession No |
|---|---|---|---|
| 40 | Uncultured bacterium clone BD8806 | Pectate lyase | AY836643 |
| 41 | Uncultured bacterium clone BD9837 | Pectate lyase | AY836642 |
| 42 | Uncultured bacterium clone BD7566 | Pectate lyase | AY836641 |
| 43 | Uncultured bacterium clone BD7563 | Pectate lyase | AY836640 |
| 44 | Uncultured bacterium clone BD9170 | Pectate lyase | AY836639 |
| 45 | Uncultured bacterium clone BD8765 | Pectate lyase | AY836638 |
| 46 | Uncultured bacterium clone BD7651 | Pectate lyase | AY836637 |
| 47 | Uncultured bacterium clone BD7842 | Pectate lyase | AY836636 |
| 48 | Uncultured bacterium clone BD7564 | Pectate lyase | AY836635 |
| 49 | Uncultured bacterium clone BD7567 | Pectate lyase | AY836634 |
| 50 | Uncultured bacterium clone BD8804 | Pectate lyase | AY836633 |
| 51 | Uncultured bacterium clone BD8113 | Pectate lyase | AY836632 |
| 52 | Uncultured bacterium clone BD8803 | Pectate lyase | AY836631 |
| 53 | Uncultured bacterium clones | Pectate lyase | AY836611 to AY836630 |
| 54 | *Aspergillus niger* | pelA | X55784 |
| 55 | *Aspergillus niger* | pelC | AY839647 |
| 56 | *Penicillium expansum* | pectin lyase (ple1) | AY545054 |
| 57 | *Blumeria graminis* f. sp. *tritici* | pectin lyase 2-like gene, partial sequence | AY297036 |
| 58 | *Aspergillus oryzae* | pel2 gene for pecyin lyase 2 | AB029323 |
| 59 | *Aspergillus oryzae* | pel1 gene for pecyin lyase 1 | AB029322 |
| 60 | *Colletotrichum gloeosporioides* f. sp. *malvae* | pectin lyase (pnl1) | AF158256 |
| 61 | *Colletotrichum gloeosporioides* f. sp. *malvae* | pectin lyase 2 (pnl-2) | AF156984 |
| 62 | *Bacillus* sp. P-358 | pelP358 gene for pectate lyase P358 | AB062880 |
| 63 | *Aspergillus niger* | pectin lyase D (pelD) | M55657 |
| 64 | *Erwinia carotovora* | pectin lyase (pnl) | M65057 |
| 65 | *Erwinia carotovora* | pectin lyase (pnlA) | M59909 |
| 66 | *Bacillus* sp. YA-14 | pelK gene for pectate lyase | D26349 |
| 67 | *Streptomyces thermocarboxydus* | pl2 gene for pectate lyase | AB375312 |
| 68 | | | |
| 69 | *Pseudomonas viridiflava* strain RMX3.1b | pectate lyase | DQ004278 |
| 70 | *Pseudomonas viridiflava* strain RMX23.1a | pectate lyase | DQ004277 |
| 71 | *Pseudomonas viridiflava* strain PNA3.3a | pectate lyase | DQ004276 |
| 72 | *Pseudomonas viridiflava* strain LP23.1a | pectate lyase | DQ004275 |
| 73 | *Aspergillus fumigatus* Af293 | pectate lyase A | XM_744120 |
| 74 | *Aspergillus niger* CBS 513.88 | pectate lyase plyA | XM_0014402441 |
| 75 | *Emericella nidulans* | pelA | EF452421 |
| 76 | *Bacillus* sp. P-4-N | pel-4B gene for pectate lyase Pel-4B | AB042100 |
| 77 | *Bacillus* sp. P-4-N | pel4A gene for pectate lyase Pel-4A | AB041769 |
| 78 | *Fusarium solani* | pelB | U13051 |
| 79 | *Fusarium solani* | pelC | U13049 |
| 80 | *Fusarium solani* | pelD | U13050 |
| 81 | *Fusarium solani pisi* (*Nectria hematococca*) | pectate lyase (pelA) | M94692 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10676751B2). An electronic copy of the "Sequence Listing" will also be available from the USPTO upon request and payment of the fee set forth in 37 CFR 1.19(b)(3).

What is claimed is:

1. A method of degrading a plant biomass sample so as to release fermentable sugars therein, the method comprising obtaining a plant degrading enzyme cocktail comprising plant cell extracts comprising active plant degrading enzymes recombinantly expressed in chloroplasts of plant cells, and admixing said plant degrading enzyme cocktail with said biomass sample, wherein said cocktail comprises recombinant CelD cellulase encoded by sequences obtained from *Clostridium thermocellum*, ligninase, recombinant beta-glucosidase encoded by sequences obtained from *Trichoderma reesei*, hemicellulase, xylanase encoded by sequences obtained from *Trichoderma reesei*, recombinant alpha amylase encoded by sequences obtained from *Bacillus* ssp., amyloglucosidase, recombinant PelB and PelD pectate lyases encoded by sequences obtained from *Fusarium solani*, lipase encoded by sequences obtained from *Mycobacterium tuberculosis*, maltogenic alpha-amylase encoded by sequences obtained from *Bacillus* ssp., acetyl xylan esterase encoded by sequences obtained from *Trichoderma reesei*, cutinase encoded by sequences obtained from *Fusarium solani*, and swollenin encoded by sequences obtained from *Trichoderma reesei*, wherein said CelD, PelB, and PelD exhibit elevated levels of enzymatic activity at higher temperatures and/or broader pH ranges relative to *E. coli*-expressed CelD, PelB, and PelD enzymes, respectively, said plant degrading enzyme cocktail acting synergistically to release fermentable sugars produced from said biomass sample.

2. The method of claim 1, comprising at least one bacterial cell extract comprising a second plant degrading enzyme.

3. The method of claim 1, wherein said plant degrading enzyme cocktail comprises at least one additional chloroplast-expressed recombinant cellulase selected from the group consisting of CelO exoglucanase encoded by sequences obtained from *Clostridium thermocellum*, egI endoglucanase, egII endoglucanase, each being encoded by sequences obtained from *Trichoderma reesei*.

4. The method of claim 1, wherein said plant biomass sample comprises grain and/or grain residues, sugar beet, sugar cane, grasses, wood-based biomass, fruits and/or fruit waste residues, or a combination thereof.

5. The method of claim 4, wherein said plant biomass is corn, wheat, barley, or citrus, or waste residues obtained therefrom.

6. The method of claim 4, wherein said plant biomass is switchgrass.

7. A method of degrading a plant biomass sample so as to release fermentable sugars therein, the method comprising obtaining a plant degrading enzyme cocktail comprising plant cell extracts comprising active plant degrading enzyme recombinantly expressed in chloroplasts of plant cells, and admixing said plant degrading enzyme cocktail with said biomass sample, wherein said plant biomass is sawdust or a wood-based biomass and said plant degrading enzymes consist of CelD endoglucanase, CelO exoglucanase each being encoded by sequences obtained from *Clostridium thermocellum*; beta-glucosidase, xylanase, acetyl xylan esterase each being encoded by sequences obtained from *Trichoderma reesei*; PelA pectate lyase, PelB pectate lyase, PelD pectate lyase each being encoded by sequences obtained from *Fusarium solani*; and swollenin encoded by sequences obtained from *Trichoderma reesei*, and said plant degrading enzyme cocktail is effective to release 100% fermentable sugars produced from said sawdust or wood-based biomass.

8. The method of claim 4, wherein said plant biomass is sugar cane.

9. A method of degrading a plant biomass sample so as to release fermentable sugars therein, the method comprising obtaining a plant degrading enzyme cocktail comprising plant cell extracts comprising active plant degrading enzyme recombinantly expressed in chloroplasts of plant cells, and admixing said plant degrading enzyme cocktail with said biomass sample, wherein said plant biomass is citrus peel and said plant degrading cocktail contains enzymes consisting of CelD endoglucanase, CelO exoglucanase each being encoded by sequences obtained from *Clostridium thermocellum*; beta-glucosidase, xylanase, acetyl xylan esterase each being encoded by sequences obtained from *Trichoderma reesei*; lipase encoded by sequences obtained from *Mycobacterium tuberculosis*, PelA pectate lysase, PelB pectate lyase, PelD pectate lyase each being encoded by sequences obtained from *Fusarium solani*; cutinase encoded by a sequence obtained from *Fusarium solani*, and swollenin encoded by sequences obtained from *Trichoderma reesei*, and said plant degrading enzyme cocktail is effective to release 100% fermentable sugars from said citrus peel biomass.

10. The method of claim 4, wherein said plant biomass is sugar beet.

11. The method of claim 1, wherein said plant degrading cocktail further comprises rubisco.

12. A plant material useful for degrading a processed wood biomass, said material comprising chloroplast-expressed CelD endoglucanase, CelO exoglucanase each being encoded by sequences obtained from *Clostridium thermocellum*; beta-glucosidase, xylanase, acetyl xylan esterase each being encoded by sequences obtained from *Trichoderma reesei*; PelA pectate lyase, PelB pectate lysase, PelD pectate lyase, each being encoded by sequences obtained from *Fusarium solani*; and swollenin encoded by a sequence obtained from *Trichoderma reesei*, and said plant degrading enzyme cocktail being effective to release 100% fermentable sugars produced from said sawdust or wood-based biomass.

13. A plant material for degrading a citrus peel biomass wherein said plant material comprises chloroplast expressed CelD endoglucanase, CelO exoglucanase each being encoded by sequences obtained from *Clostridium thermocellum*; beta-glucosidase, xylanase, acetyl xylan esterase each being encoded by sequences obtained from *Trichoderma reesei*; lipase encoded by sequences obtained from *Mycobacterium tuberculosis*, PelA pectate lysase, PelB pectate lyase, PelD pectate lyase each being encoded by sequences obtained from *Fusarium solani*; cutinase encoded by sequences obtained from *Fusarium solani*, and swollenin encoded by sequences obtained from *Trichoderma reesei*, and said plant degrading enzyme cocktail is effective to release 100% fermentable sugars from said citrus peel biomass.

14. The homogenized plant material of claim 12, in powdered form.

15. The method of claim 13, wherein said plant material is in powdered form.

\* \* \* \* \*